United States Patent
Marteyn et al.

(10) Patent No.: US 11,472,844 B2
(45) Date of Patent: Oct. 18, 2022

(54) PEPTIDOMIMETICS, METHOD OF SYNTHESIS AND USES THEREOF

(71) Applicants: INSTITUT PASTEUR, Paris (FR); INSTITUT NATIONAL DE LA SANTE ET DE LA RECHERCHE MEDICALE, Paris (FR); CENTRE NATIONAL DE LA RECHERCHE SCIENTIFIQUE, Paris (FR)

(72) Inventors: Benoit Sebastien Marteyn, Paris (FR); Yves-Marie Coic, Meudon (FR); Francoise Baleux, Paris (FR)

(73) Assignees: CENTRE NATIONAL DE LA RECHERCHE SCIENTIFIQUE, Paris (FR); INSERM (INSTITUT NATIONAL DE LA SANTÉ ET DE LA RECHERCHE MÉDICALE), Paris (FR); INSTITUT PASTEUR, Paris (FR)

( * ) Notice: Subject to any disclaimer, the term of this patent is extended or adjusted under 35 U.S.C. 154(b) by 0 days.

(21) Appl. No.: 16/771,114

(22) PCT Filed: Dec. 11, 2018

(86) PCT No.: PCT/EP2018/084363
§ 371 (c)(1),
(2) Date: Jun. 9, 2020

(87) PCT Pub. No.: WO2019/115527
PCT Pub. Date: Jun. 20, 2019

(65) Prior Publication Data
US 2020/0369729 A1    Nov. 26, 2020

(30) Foreign Application Priority Data

Dec. 11, 2017 (EP) .................................... 17306746

(51) Int. Cl.
| | |
|---|---|
| *G01N 33/68* | (2006.01) |
| *C07K 14/00* | (2006.01) |
| *C07K 1/06* | (2006.01) |
| *C07K 1/10* | (2006.01) |
| *G01N 1/30* | (2006.01) |
| *A61K 38/00* | (2006.01) |

(52) U.S. Cl.
CPC ............ *C07K 14/001* (2013.01); *C07K 1/061* (2013.01); *C07K 1/10* (2013.01); *G01N 1/30* (2013.01); *G01N 33/68* (2013.01); *A61K 38/00* (2013.01); *G01N 2001/302* (2013.01); *G01N 2333/4725* (2013.01)

(58) Field of Classification Search
None
See application file for complete search history.

(56) References Cited

U.S. PATENT DOCUMENTS

| | | |
|---|---|---|
| 9,382,299 B2 | 7/2016 | Marteyn et al. |
| 10,138,280 B2 | 11/2018 | Marteyn et al. |

FOREIGN PATENT DOCUMENTS

| | | | |
|---|---|---|---|
| WO | 2013/034749 A1 | 3/2013 | |
| WO | WO-2013034749 A1 * | 3/2013 | ........... C07K 14/335 |

OTHER PUBLICATIONS

Ugonotti, Julian et al; "Structural and functional diversity of neutrophil glycosylation in innate immunity and related disorders." Mol. Asp. Med (2020.*
Antonelli, Elisabetta et al; "Intestinal superinfections in patients with inflammaotry bowel disease." J. Chrohns Colitis (2012) 6 p. 154-159.*
The webpage describing the program PEP2D, Singh et al., https://webs.iiitd.edu.in/raghava/pep2d/, downloaded Aug. 19, 2021.*
The webpage for the program SwissModel, Schwede, https://swissmodel.expasy.org/, downloaded Aug. 19, 2021.*

(Continued)

*Primary Examiner* — Fred H Reynolds
(74) *Attorney, Agent, or Firm* — Arrigo, Lee, Guttman & Mouta-Bellum LLP

(57) ABSTRACT

The invention relates to a peptidomimetic comprising or consisting of a D amino-acid sequence having at least 75% identity with SEQ ID NO: 1 or SEQ ID NO: 2, or variants or fragments thereof, in particular a peptidomimetic having the capability to interact at least with: neutrophils and/or neutrophil granules, and/or lactoferrin, and/or globet-cells and/or Muc2 proteins, and/or mucus and/or airway sputum. The peptidomimetic may have the capacity to adopt a multimeric, especially a trimeric, organization, and can be labelled, or associated with a reporter or a carrier entity, or associated with an active molecule. The invention also relates to a Solid-Phase Synthesis method for synthesizing a peptidomimetic of the invention, compositions comprising the same and use of the peptidomimetics as a medicamentor an inflammation marker or a neutrophilic inflammation marker. The invention also relates to the use of a peptidomimetic as a probe or marker for staining purposes, or to detect mucus production, or neutrophils, or to detect or monitor diseases or conditions, especially neutrophilic inflammation. The invention also relates to the use of a polypeptide comprising or consisting of SEQ ID NO: 3, or variants or fragments thereof, as probe or marker for staining lactoferrin, in particular neutrophil lactoferrin, or a probe or marker for investigating neutrophilic inflammation, especially in an imaging method.

24 Claims, 27 Drawing Sheets

Figure 1A:
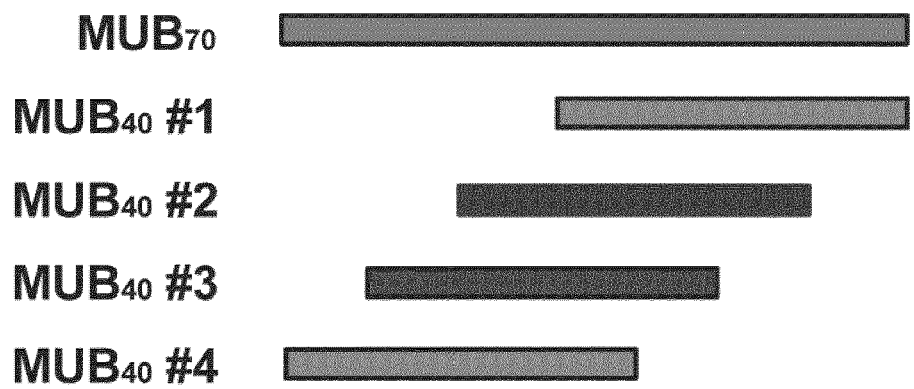

Specification includes a Sequence Listing.

(56) References Cited

OTHER PUBLICATIONS

Rocklin, Gabriel J. et al; "GLobal analysis of protein folding using massively parallel design, synthesis, and testing." Science (2017) 357 p. 168-175.*

Howes, Larua; "Deepmind ai predicts protein structures." C&EN, Dec. 1, 2020.*

Michael Chorev, "A Dozen Years of Retro-Inverso Peptidomimetics," Acc. Chem. Res, 1993, 26, 266-273.

Yves-Marie Coic, et al., "Design of a Specific Colonic Mucus Marker Using a Human Commensal Bacterium Cell Surface Domain," The Journal of Biological Chemistry, vol. 287, No. 19, 2012, pp. 15916-15922.

Matthew David Fletcher, et al., "Partially Modified Retro-lnverso Peptides: Development, Synthesis, and Conformational Behavior," Chem. Rev., 1998, vol. 98, 763-795.

Keita Nishiyama, et al., "Adhesion Properties of Lactic Acid Bacteria on Intestinal Mucin," Microorganisms, vol. 4, No. 4, 2016, p. 34.

International Search Report, PCT/EP2018/084363, dated Dec. 2, 2019.

European Search Report, EP17306746, dated Mar. 22, 2018.

Mark C. Anderson, et al., "The MUB40 Peptide for Use in Detecting Neutrophil-Mediated Inflammation Events," J. Vis. Exp. (143), e58367, doi:10.3791/58367 (2019).

Abiodun Ayo, et al., "Tumor-Targeting Peptides: The Functional Screen of Glioblastoma Homing Peptides to the Target Protein FABP3 (MDGI)," Cancers 2020, 12, 1836.

Chorev and Goodman, "Symmetry transformations at $\alpha$-carbons: reply," Tibtech 1996, vol. 14, pp. 43-44).

Jagdish Rai, "Retroinverso Mimetics of S Peptide," Chem Biol Drug Des 2007; 70: 552-556.

Fuente-Nunez et al., "D-Enantiomeric Peptides that Eradicate Wild-Type and Multidrug-Resistant Biofilms and Protect against Lethal Pseudomonas aeruginosa Infections," 2015, Chemistry & Biology 22, 196-20.

Gilles Guichard, et al., "Structural limitations to antigenic mimicry achievable with retro-inverso (all-D-retro) peptides," Tibtech 1996, vol. 14, pp. 44-45.

L.K. Iwaia, et al., "Retro-inverso peptide analogues of Trypanosoma cruzi B13 protein epitopes fail to be recognized by human sera and peripheral blood mononuclear cells," Peptides 22 (2001) 853-860.

Chong Li, et al., "Limitations of Peptide Retro-inverso Isomerization in Molecular Mimicry," The Journal of Biological Chemistry vol. 285, No. 25, pp. 19572-19581, Jun. 18, 2010.

Ipsita Pal-Bhowmick, et al., "Structural and functional studies on Ribonuclease S, retro S and retro-inverso S peptides," Biochemical and Biophysical Research Communications 364 (2007) 608-613.

* cited by examiner

Human colonic mucus

Human colon goblet cells

| Name | SEQ ID NO: | |
|---|---|---|
| MUB40-1 | 3 | Ac-CTAEGIKKFEGDGYELFKDNFPAGEKFDNDDTNDQFYTVIF-amide |
| MUB40-2 | 4 | Ac-CGYTDETIPYSTAEGIKKFEGDGYELFKDNFPAGEKFDNDD-amide |
| MUB40-3 | 5 | Ac-CDQMLRQDDLDGYTDETIPYSTAEGIKKFEGDGYELFKDNF-amide |
| MUB40-4 | 6 | Ac-CVHVQYIDGETDQMLRQDDLDGYTDETIPYSTAEGIKKFEG-amide |

Fig. 2A

Human Peripheral blood mononuclear cells (PBMCs)

Polymorphonuclear neutrophils

**Guinea pig colon infected with *Shigella flexneri***

Oligomerized human Lactoferrin

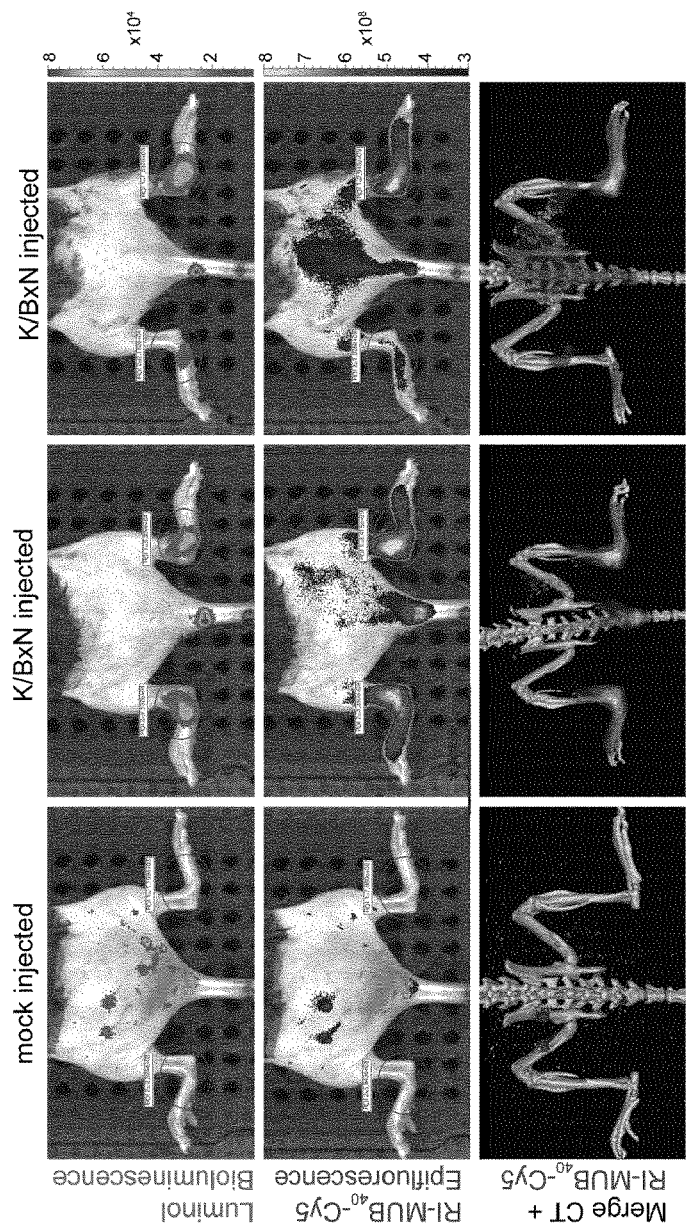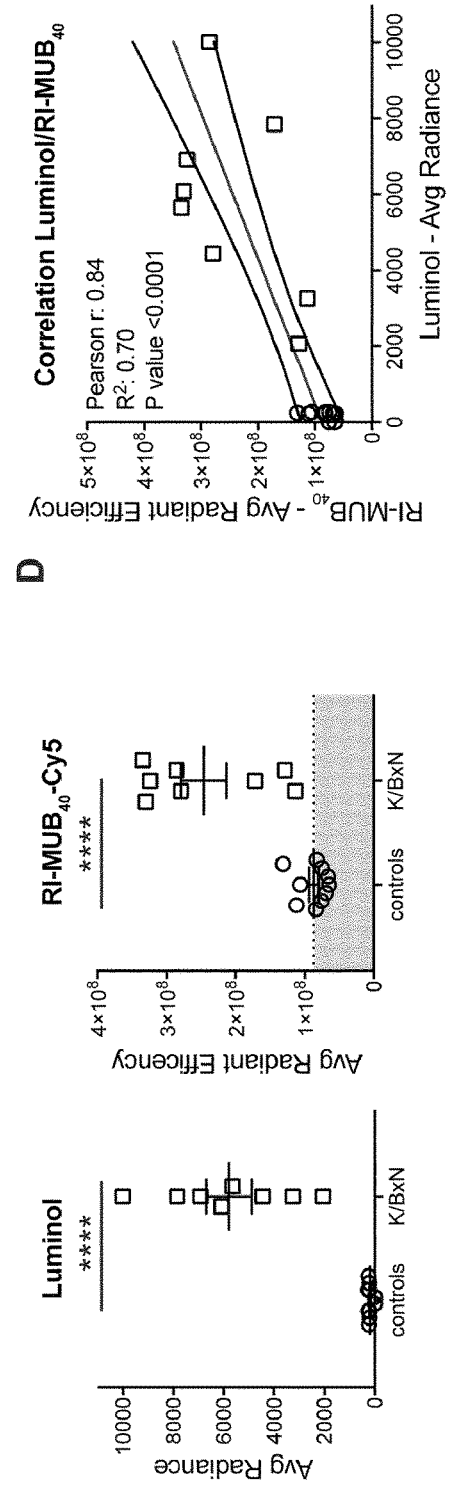
Fig. 16C, D

SEQUENCE LISTING

```
<160> NUMBER OF SEQ ID NOS: 11

<210> SEQ ID NO 1
<211> LENGTH: 40
<212> TYPE: PRT
<213> ORGANISM: artificial
<220> FEATURE:
<223> OTHER INFORMATION: RI-MUB40 synthetic sequence with D amino acids
<220> FEATURE:
<221> NAME/KEY: MISC_FEATURE
<222> LOCATION: (1)..(40)
<223> OTHER INFORMATION: All amino acid residues are D amino acids

<400> SEQUENCE: 1

Phe Ile Val Thr Tyr Phe Gln Asp Asn Thr Asp Asp Asn Asp Phe Lys
1               5                   10                  15

Glu Gly Ala Pro Phe Asn Asp Lys Phe Leu Glu Tyr Gly Asp Gly Glu
            20                  25                  30

Phe Lys Lys Ile Gly Glu Ala Thr
        35                  40

<210> SEQ ID NO 2
<211> LENGTH: 41
<212> TYPE: PRT
```

```
<213> ORGANISM: artificial
<220> FEATURE:
<223> OTHER INFORMATION: RI-MUB40 synthetic sequence with D amino acids,
      with Cysteine at N terminal extremity
<220> FEATURE:
<221> NAME/KEY: MISC_FEATURE
<222> LOCATION: (1)..(40)
<223> OTHER INFORMATION: All amino acid residues are D amino acids

<400> SEQUENCE: 2

Cys Phe Ile Val Thr Tyr Phe Gln Asp Asn Thr Asp Asp Asn Asp Phe
1               5                   10                  15

Lys Glu Gly Ala Pro Phe Asn Asp Lys Phe Leu Glu Tyr Gly Asp Gly
                20                  25                  30

Glu Phe Lys Lys Ile Gly Glu Ala Thr
            35                  40

<210> SEQ ID NO 3
<211> LENGTH: 41
<212> TYPE: PRT
<213> ORGANISM: artificial
<220> FEATURE:
<223> OTHER INFORMATION: MUB40-1 probe with Cysteine at N-terminal
      extremity

<400> SEQUENCE: 3

Cys Thr Ala Glu Gly Ile Lys Lys Phe Glu Gly Asp Gly Tyr Glu Leu
1               5                   10                  15

Phe Lys Asp Asn Phe Pro Ala Gly Glu Lys Phe Asp Asn Asp Asp Thr
                20                  25                  30

Asn Asp Gln Phe Tyr Thr Val Ile Phe
            35                  40

<210> SEQ ID NO 4
<211> LENGTH: 41
<212> TYPE: PRT
<213> ORGANISM: artificial
<220> FEATURE:
<223> OTHER INFORMATION: MUB40-2 probe with Cysteine at N-terminal
      extremity

<400> SEQUENCE: 4

Cys Gly Tyr Thr Asp Glu Thr Ile Pro Tyr Ser Thr Ala Glu Gly Ile
1               5                   10                  15

Lys Lys Phe Glu Gly Asp Gly Tyr Glu Leu Phe Lys Asp Asn Phe Pro
                20                  25                  30

Ala Gly Glu Lys Phe Asp Asn Asp Asp
            35                  40

<210> SEQ ID NO 5
<211> LENGTH: 41
<212> TYPE: PRT
<213> ORGANISM: artificial
<220> FEATURE:
<223> OTHER INFORMATION: MUB40-3 probe with Cysteine at N terminal
      extremity

<400> SEQUENCE: 5

Cys Asp Gln Met Leu Arg Gln Asp Asp Leu Asp Gly Tyr Thr Asp Glu
1               5                   10                  15

Thr Ile Pro Tyr Ser Thr Ala Glu Gly Ile Lys Lys Phe Glu Gly Asp
                20                  25                  30

Gly Tyr Glu Leu Phe Lys Asp Asn Phe
            35                  40
```

<210> SEQ ID NO 6
<211> LENGTH: 41
<212> TYPE: PRT
<213> ORGANISM: artificial
<220> FEATURE:
<223> OTHER INFORMATION: MUB40-4 probe with Cysteine at N terminal
      extremity

<400> SEQUENCE: 6

Cys Val His Val Gln Tyr Ile Asp Gly Glu Thr Asp Gln Met Leu Arg
1               5                   10                  15

Gln Asp Asp Leu Asp Gly Tyr Thr Asp Glu Thr Ile Pro Tyr Ser Thr
            20                  25                  30

Ala Glu Gly Ile Lys Lys Phe Glu Gly
        35                  40

<210> SEQ ID NO 7
<211> LENGTH: 40
<212> TYPE: PRT
<213> ORGANISM: artificial
<220> FEATURE:
<223> OTHER INFORMATION: MUB40-1 probe sequence without Cysteine at N
      terminal extremity

<400> SEQUENCE: 7

Thr Ala Glu Gly Ile Lys Lys Phe Glu Gly Asp Gly Tyr Glu Leu Phe
1               5                   10                  15

Lys Asp Asn Phe Pro Ala Gly Glu Lys Phe Asp Asn Asp Thr Asn
            20                  25                  30

Asp Gln Phe Tyr Thr Val Ile Phe
        35                  40

<210> SEQ ID NO 8
<211> LENGTH: 40
<212> TYPE: PRT
<213> ORGANISM: artificial
<220> FEATURE:
<223> OTHER INFORMATION: MUB40-2 probe without Cysteine at N terminal
      extremity

<400> SEQUENCE: 8

Gly Tyr Thr Asp Glu Thr Ile Pro Tyr Ser Thr Ala Glu Gly Ile Lys
1               5                   10                  15

Lys Phe Glu Gly Asp Gly Tyr Glu Leu Phe Lys Asp Asn Phe Pro Ala
            20                  25                  30

Gly Glu Lys Phe Asp Asn Asp Asp
        35                  40

<210> SEQ ID NO 9
<211> LENGTH: 40
<212> TYPE: PRT
<213> ORGANISM: artificial
<220> FEATURE:
<223> OTHER INFORMATION: MUB40-3 probe without Cysteine at N-terminal
      extremity

<400> SEQUENCE: 9

Asp Gln Met Leu Arg Gln Asp Asp Leu Asp Gly Tyr Thr Asp Glu Thr
1               5                   10                  15

Ile Pro Tyr Ser Thr Ala Glu Gly Ile Lys Lys Phe Glu Gly Asp Gly
            20                  25                  30

Tyr Glu Leu Phe Lys Asp Asn Phe

-continued

```
<210> SEQ ID NO 10
<211> LENGTH: 40
<212> TYPE: PRT
<213> ORGANISM: artificial
<220> FEATURE:
<223> OTHER INFORMATION: MUB40-4 probe without Cysteine at N terminal
      extremity

<400> SEQUENCE: 10

Val His Val Gln Tyr Ile Asp Gly Glu Thr Asp Gln Met Leu Arg Gln
1               5                   10                  15

Asp Asp Leu Asp Gly Tyr Thr Asp Glu Thr Ile Pro Tyr Ser Thr Ala
            20                  25                  30

Glu Gly Ile Lys Lys Phe Glu Gly
        35                  40

<210> SEQ ID NO 11
<211> LENGTH: 70
<212> TYPE: PRT
<213> ORGANISM: Lactobacillus reuteri

<400> SEQUENCE: 11

Val His Val Gln Tyr Ile Asp Gly Glu Thr Asp Gln Met Leu Arg Gln
1               5                   10                  15

Asp Asp Leu Asp Gly Tyr Thr Asp Glu Thr Ile Pro Tyr Ser Thr Ala
            20                  25                  30

Glu Gly Ile Lys Lys Phe Glu Gly Asp Gly Tyr Glu Leu Phe Lys Asp
        35                  40                  45

Asn Phe Pro Ala Gly Glu Lys Phe Asp Asn Asp Thr Asn Asp Gln
    50                  55                  60

Phe Tyr Thr Val Ile Phe
65                  70
```

PEPTIDOMIMETICS, METHOD OF SYNTHESIS AND USES THEREOF

The invention relates to peptidomimetics, more particularly retro-inverso (RI) polypeptides or oligopeptides, designed on the basis of polypeptides that have been shown, on one hand, to interact with the glycosylated moiety of Muc2 proteins, as found in mucus layers of various biological tissues, especially human colonic tissue, and on the other hand, to interact with neutrophil granules, especially human neutrophil granules. According an outstanding aspect of the invention, particular polypeptides, in particular retro-inverso (RI) polypeptides as described herein, have particularly been shown to bind to lactoferrin, which is a protein that can be found, in particular, stored in neutrophile granules.

The invention also relates to a solid phase synthesis method for synthesizing the peptidomimetics of the invention.

The invention also relates to composition(s) comprising the same, in particular to pharmaceutical composition(s) including if necessary carrier(s) or adjuvant(s).

The peptidomimetics of the invention may be used, as markers, for staining cell(s) in in vivo, ex vivo, especially in vitro, experiments, in particular in live microscopy experiments. Cell(s) can accordingly be neutrophil(s). Accordingly, the peptidomimetics of the invention may also be used as exploratory or diagnosis-assisting tools, when neutrophil containing samples and/or mucus samples can be recovered from a patient or a subject susceptible of suffering from a disease.

The peptidomimetics of the invention may also be used, as bio-conjugates, for therapeutic applications in diseases in which neutrophil-mediated inflammation is at stake, and/or in which mucus should be targeted or in which mucus production is problematic, or both.

More particularly, probe(s) of the invention may target mucus potentially containing Muc2 protein(s), especially, but not exclusively, as found in human colonic mucus or respiratory tract mucus, or as produced by eukaryotic cell(s).

According to another aspect, the invention also relates to means for targeting neutrophils, especially human neutrophils, more particularly neutrophil granules and/or means for monitoring degranulation event(s) in said neutrophil, in particular through interaction with lactoferrin and/or glycosylated lactoferrin.

The invention also relates to the use of a polypeptide related to non retro-inverso probes disclosed in the art, or variants thereof as defined herein, as an in vitro probe or marker for staining lactoferrin, in particular neutrophil lactoferrin, especially neutrophil lactoferrin stored in neutrophil specific granules (β1) and/or tertiary granules (β2) and/or secreted by neutrophils.

The so-called MUB70 probe has been described in WO 2013/034749 A1, incorporated by reference in its entirety, and Coïc, Y. M., Baleux, F., Poyraz, O., Thibeaux, R., Labruyere, E., Chretien, F., Sobhani, I., Lazure, T., Wyplosz, B., Schneider, G., Mulard, L., Sansonetti, P. J., and Marteyn, B. S. Design of a specific colonic mucus marker using a human commensal bacterium cell surface domain (2012) The Journal of biological chemistry, 19 15916-15922). The MUB70 probe was the first peptidic marker of human colonic mucus synthesized and characterized (MUB70 sequence (70AAs) was identified in *L. reuteri* MUcus Binding Associated Domains (MUBAD) and was shown to be involved in a direct interaction with the glycosylated moiety of the Muc2 protein. In addition of the labeling of the colonic mucus released by goblet cells, a specific labeling of colonic mucinous carcinoma was also demonstrated (Coïc et al., 2012, supra).

WO 2013/034749 A1 also reports the synthesis of shorter probes aimed at functionally mimicking MUB70 properties. More particularly, 40AAs-overlapping polypeptides spanning the MUB70 peptide sequence, i.e., MUB40 probes, have been synthesized and covalently linked to a Cy5 fluorophore in order to assess their respective mucus-binding property. Amongst the four synthesized MUB40 probes (MUB40 #1, MUB40 #2, MUB40 #3 and MUB40 #4, respectively identified under SEQ ID NO: 3, SEQ ID NO: 4, SEQ ID NO: 5 and SEQ ID NO: 6 herein, wherein said polypeptides encompass an additional cysteine residue at their N-terminal extremity, which can be absent or removed, as shown in SEQ ID NOs: 7, 8, 9 and 10, respectively), only the MUB40 #1-Cy5 probe has proven to be a functional human mucus-binding peptide, additionally possessing globlet-cells binding properties in comparison with MUB70-Cy5.

WO 2013/034749 A1 also reports that MUB70 and MUB40 probes covalently linked to a Cy5 fluorophore have been found to actually label neutrophil granules, although this reason of this labelling specificity remained non-elucidated. These probes have merely been suspected to target components found at the level of neutrophil granules.

It has consequently been proposed in WO 2013/034749 A1 to use these probes as in vitro marker of degranulation event(s) in neutrophils. Neutrophils, strictly speaking termed polymorphonuclear neutrophils, are the most abundant type of granulocytes and the most abundant type of white blood cells in most mammals, and form part of the innate immune system (when the expression neutrophil is used herein, it is intended to designate polymorphonuclear neutrophil, unless indicated otherwise). Neutrophils are normally found un the bloodstream. Early in an inflammation process, including in some cancers, neutrophils are one of the first responders of inflammatory cells to migrate towards the site of inflammation. This recruitment makes them potentially interesting inflammatory markers.

In fact, polymorphonuclear neutrophils are actually the most abundant immune cell population recruited to inflammatory tissues. Once recruited, neutrophils release proteins and cytokines contributing to the overall innate immune response. Proteins secreted by neutrophils upon their stimulation, are stored in pre-formed granules. Neutrophils contain four distinct granule populations named azurophil granules (α), specific granules (β1), tertiary granules (β2) and secretory vesicles (γ), which are sequentially formed during granulopoiesis. When activated, neutrophils sequentially release the protein content of stored granules. Granules formed during the later stage of granulopoiesis are more prone to exocytosis. Neutrophil granule protein content has been first investigated by Borregaard and colleagues and since then extensively studied in vitro and in vivo during inflammation and immune response (Cowland and Borregaard, 2016; Kjeldsen et al., 1999; Sengelov et al., 1995), (Borregaard et al., 2007), (Faurschou and Borregaard, 2003), (Soehnlein et al., 2009). Increased seric concentrations of neutrophil secreted proteins were reported in various inflammatory diseases such as inflammatory bowel disease (IBD) (Gouni-Berthold et al., 1999), or colorectal cancer (Ho et al., 2014). Inflammatory states were also correlated with high concentration of neutrophil secreted proteins in faeces (IBD (Däbritz et al., 2014), (Lehmann et al., 2015)) or in sputum (cystic fibrosis (Sage) et al., 2012)).

There is accordingly a need for the development of proper, suitable and practical inflammatory markers, aimed at assessing or further characterize inflammatory events, and/or their occurrence.

However, neutrophils also produce, in vivo, a wide variety of proteases (elastase, proteinase 3, cathepsin G), stored in granules and potentially released upon stimulation. It therefore remained a concern that the labelling of living neutrophils, even in in vitro experiments, with the prior art MUB70-Cy5 or MUB40-Cy5 probes could be impaired by the potential sensitivity of these probes to proteases. As long as they contain natural L-amino acids, synthetic peptides are potentially susceptible of being cleaved by proteases.

By the same token, considering the still ongoing interest of delivering mucus-targeting probes, possibly conjugated to reporter molecules such as fluorophores or drugs, a need remains to prevent or minimize proteolytic cleavage by active enzymes, notably when such probes are administered in vivo.

Mucus is a colloidal secretion, which naturally protects human epithelium in the respiratory and the gastrointestinal tracts. Mucus production or composition in animal or human body might be modified as a result of physiological events as well as a result of several disease conditions such as neoplasic disease(s), non-limitatively including mucinous carcinoma(s), gastric cancer(s) or colorectal cancer(s), especially colon cancer(s), or diseases such as cystic fibrosis or intestine inflammatory disease(s) such as inflammatory bowel disease (IBD) and ulcerative colitis.

Furthermore, pathological productions of mucus have actually been observed and characterized in various inflammatory diseases, including mucinous carcinomas, arthritis and cystic fibrosis (CF). Until now, mucus clearance using mucolytic molecules has not been widely envisaged as a therapeutical approach although it is already used in clinics, so far with limited benefits, to improve CF patients state, as its pathological accumulation in the respiratory track is a life-threatening factor.

Altogether, this emphasizes the need for agents enabling the targeting of mucus as found in pathological conditions, states or diseases, which are often associated with inflammatory states or manifestations, let it be acute or chronic, for investigation and/or therapeutic purposes.

Amongst recent developments in peptidomimetics, Retro-inverso (RI) peptides, in which only D-amino acids are used and the change in chirality is potentially counteracted by reversing the primary sequence, are well known. RI-peptides contain inter-amino acid bonds that are the most closely related isosteric replacements for the original peptide bond. These modifications are believed to preserve the major structural characteristics of the peptide backbone while substantially changing their native structure. Consequently, RI-peptides generally have increased stability as demonstrated for a number of peptides, including enkephalin, glutathione, Substance P, gastrin, and atrial natriuretic peptide (Chorev et al., 1993, Chorev et al., 1995). More recently, convincing examples of RI-peptides were proven to preserve antimicrobial activity (lorns et al., 2014) or receptor binding properties associated to the reference L peptide (Wang et al., 2014, Wei et al., 2015). The improved metabolic stability of RI-peptides allowed the design of proteolytically stable conjugates for the treatment of CNS diseases, as gene (Wang et al., 2014) or liposome-encapsulated drug (Wei et al., 2015) delivery vector.

In fact, it should nevertheless be emphasized that it has been shown in the art that although retro-inverso (RI) synthetic peptides, which are made of D-amino acids with a reversed amino-acid sequence with respect to their L counterpart, may mimic the side chain conformation of said all L amino-acids counterpart, the provision of the RI corresponding peptide is not necessarily associated with the possibility of keeping the target recognition properties of the departure L counterpart peptide. For instance, it has been reported by Iwai et al., in Peptides 22 (2001) 853-860, that a particular Retro-inverso peptide analogue a of *Trypanosoma cruzi* B13 protein epitope failed to be recognized by human sera and peripheral blood mononuclear cells. The authors did not exclude that a three-dimensional structural difference in the side chain disposition of the peptide could explain the observed lack of recognition. Also, Fuente-Nunez et al., 2015, Chemistry & Biology 22, 196-205, "D-Enantiomeric Peptides that Eradicate Wild-Type and Multidrug-Resistant Biofilms and Protect against Lethal *Pseudomonas aeruginosa* Infections", describes retro-inverso versions of a so-called peptide L1018 that, while retaining antipseudomonal antibiofilm activity, lost activity versus *Klebsiella biofilms*. The authors state that there was substantial variability in activity between the D and RI versions of several peptides, indicating that there is no simple relationship between enantiomeric compositions and activity.

The present invention generally addresses the need to provide, for detection or therapeutic purposes, acceptable biological vehicles targeting moieties of interest, and having a stronger resistance to enzymatic degradation, while retaining their binding specificity with their target(s).

The invention is also concerned with the provision of acceptable biological vehicles having adequate chemical access to their target(s), in light of the particularities surrounding mucus-targeting, or neutrophil granules targeting investigated in the art.

The invention is also concerned with the provision of accessible labelling tools (production, costs) for research in the field of mucinous and/or inflammatory diseases, including inflammatory diseases related to mucinous diseases.

The invention is also concerned with the provision of appropriate tools, especially vehicles, to further design efficient mucolytic conjugates.

The present invention is based on further experiments aimed at assessing the particularities of the probes disclosed in WO 2013/034749 A1, and subsequent findings resulting from the evaluation of a Retro-inverso MUB40 peptide including an additional cysteine at its N-terminus, said peptide being termed RI-MUB40 (SEQ ID NO: 2) in the Experimental Section.

In fact, the present invention relies on experiments demonstrating that de novo designed and synthesized probes, in line with further findings concerning the so-called MUB-40 #1 probe of the prior art, have the capability to interact, in particular bind, especially specifically bind, a newly discovered target, which is lactoferrin, especially lactoferrin as found within specific neutrophil granules, as described herein.

In turn, it happens that among neutrophil secreted proteins, lactoferrin is the most abundant and suitable neutrophil-derived faecal marker of inflammation (Sugi et al., 1996), (Martins et al., 1995) including IBD (Sipponen, 2013), (Stragier and Van Assche, 2013). However, to date, no inflammation-imaging method based on lactoferrin detection is described, although specifically stored in neutrophil granules, and not expressed by other white blood cells. Lactoferrin is an 80 kDa glycoprotein produced by neutrophils and exocrine glands located in respiratory and gastrointestinal tracts (Peen et al., 1996). Lactoferrin antimicrobial activity is associated with its iron sequestration property, limiting pathogens' (bacteria, viruses, fungi) survival and spreading (Orsi, 2004). Neutrophil lactoferrin is locally secreted by neutrophils at bacterial infection sites (Masson et al., 1969).

The experiments reported herein shows that he so-called $MUB_{40}$#1 probe (SEQ ID NO: 3), which has been previously characterized in particular as a marker of neutrophils, does in fact also binds to neutrophil lactoferrin, stored in β1 or β2 granules and released in the extracellular compartment, upon neutrophil activation. Here, $MUB_{40}$#1 probe (SEQ ID NO: 3) has been validated as a new inflammation marker in an infectious inflammatory model in tissues infected with the pathogenic enterobacteria *Shigella flexneri*, but also in sterile inflammatory models. The properties of the $MUB_{40}$#1 probe (SEQ ID NO: 3) are kept for its retro-inverso counterpart.

The invention therefore relates to a peptidomimetic comprising or consisting of:
  a. a D amino-acid sequence having at least 75% identity with FIVTYFQDNTDDNDFKEGAPFNDKF-LEYGDGEFKKIGEAT (SEQ ID NO: 1), or CFIVTYFQDNTDDNDFKEGAPFNDKF-LEYGDGEFKKIGEAT (SEQ ID NO: 2), and/or differing from SEQ ID NO: 1 or 2 by one or several conservative amino acid substitution(s), all amino-acids of SEQ ID NO: 1 or 2 being D amino-acids, or;
  b. SEQ ID NO: 1, or SEQ ID NO: 2, all amino-acids of SEQ ID NO: 1 or 2 being D amino-acids, or
  c. a D amino-acid fragment, especially a fragment of contiguous amino-acid residues of at least 10 amino-acid residues, of any one of the sequences defined in a) or b),
in particular a peptidomimetic having a length of less than 50 amino acid residues.

According to a particular aspect, the peptidomimetics of the invention are D-peptides peptidomimetics, i.e., encompass polypeptides fully constituted by D-amino acids.

By "peptidomimetic", it is meant a chemical compound encompassing a protein-like backbone designed to mimic a peptide, the altered backbone bearing modifications that involve changes to the peptide that would not occur naturally. In this respect, D-peptide peptidomimetics encompass polypeptides comprising or fully constituted by D-amino acids. This might help preventing proteolytic cleavage by active enzymes, especially when the polypeptide is administered or contacted with a sample, including a sample containing living cells, in vivo. Of note, a L-peptide sequence has three D-peptide peptidomimetics analogue counterparts: the D-enantiomer or inverso-peptide with the same sequence from its N-terminus to C-terminus, but composed of D-amino acids instead of L-amino acids; the retro-peptide, encompassing L-amino acids arranged in reverse order with respect to the original peptide; and the retro-inverso or D-retro-enantiomer peptide, consisting of D-amino acids in a reverse sequence with respect to the original peptide. L-peptides and D-retro-inverso-peptides generally share a similar arrangement of side-chains, although their carboxyl and amino groups point in opposing directions. For small peptides that do not depend on a secondary structure for binding, an L-peptide and its D-retro-inverso-peptide are likely to have a similar binding affinity with a target L-protein.

Nonetheless, it is observed that the inventors determined that the glycosylation status of the target proteins of the peptidomimetics of the invention may play a role in the interaction between the peptidomimetics of the invention and said targets. Accordingly, according to particular embodiments as further described herein, the peptidomimetics described herein interact, especially bind, with glycosylated target(s), as defined herein. In particular, said interactions may take place through glycosylated moieties of said targets.

According to a specific aspect, the peptidomimetics of the invention are considered to be Retro-inverso peptides with respect to the MUB40 #1 L-amino acid sequence disclosed in WO 2013/034749 A1 (SEQ ID NO: 3 herein, this sequence encompassing a cysteine N-terminal residue that is additional with respect to the sequence used for defining a retro-inverso polypeptide).

Accordingly, according to a particular embodiment, the peptides of the invention are Retro-Inverso peptidomimetics with respect to the MUB40 #1 L-amino acid sequence (SEQ ID NO: 3, excluding the cysteine N-terminal residue), or variants or fragments thereof.

It is observed that SEQ ID NO: 1 (FIVTYFQDNTDDND-FKEGAPFNDKFLEYGDGEFKKIGEAT) fully encompass, from its N-terminus to its C-terminus, D-amino acids. SEQ ID NO: 1 is 40 D-amino acids long. Similarly, SEQ ID NO: 2 (CFIVTYFQDNTDDNDFKEGAPFNDKF-LEYGDGEFKKIGEAT), which has an additional D-cysteine residue at the N-terminal extremity of SEQ ID NO: 1, fully encompass, from its N-terminus to its C-terminus, D-amino acids. SEQ ID NO: 2 is 41 D-amino acids long By "variant peptidomimetic", it is meant a peptidomimetic resulting from limited variations with respect to its reference sequence. Variant peptidomimetics of the invention, encompass mainly or fully D-amino acid polypeptides having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity with the sequence of reference, preferably at least 85% or at least 90% or at least 95% or 99% identity with the sequence of reference.

According to a particular embodiment, a variant peptidomimetic only encompasses D amino-acids.

For the purpose of the present disclosure, when the sequence of a peptidomimetic of the invention differs from the sequence of reference, said peptidomimetic is defined as a variant peptidomimetic. The modification(s) defining the variant peptidomimetic can independently be deletion(s), including especially point deletion(s) of one or many D-amino acid residue(s) or can be substitution(s), especially conservative substitution(s) of one or many D-amino acid residue(s).

By "one or many", it is meant a number that makes the change consistent with the identity percentages defined above.

By "identity", it is meant that the percentage of conserved amino-acid residues when a variant peptidomimetic is aligned with its reference sequence through conventional alignment algorithms is substantial, meaning that this percentage is at least one of those disclosed above, in particular at least 75%.

Identity percentages can conventionally be calculated through local, preferably global, sequence alignment algorithms and their available computerized implementations. In a most preferred embodiment, identity percentages are calculated over the entire length of the compared sequences. Optimal alignment of amino-acid sequences for comparison can for example be conducted by the local algorithm of Smith & Waterman Adv. Appl. Math. 2: 482 (1981), which is a general local alignment method based on dynamic programming, by the alignment algorithm of Needleman & Wunsch, J. Mol. Biol. 48: 443 (1970), which is also based on dynamic programming, by the search for similarity method of Pearson & Lipman, Proc. Nat'l. Acad. Sci. USA 85: 2444 (1988), or by visual inspection. Computerized implementations of these algorithms are associated with default parameters, which can be used.

A common implementation of a local sequence alignment uses the BLAST analysis, which is described in Altschul et al., J. Mol. Biol. 215: 403-410 (1990). Software for performing BLAST analyses is publicly available. For amino acid sequences, the BLAST program uses as defaults a wordsize (N) of 3, an expectation (E-value cutoff) of 10, and the BLOSUM62 scoring matrix (see Henikoff & Henikoff, Proc. Natl. Acad. Sci. USA 89: 10915 (1989)). Additionally, gap opening may be set at 11, and gap extension at 1. Local alignments are more useful for dissimilar sequences that are suspected to contain regions of similarity or similar sequence motifs within their larger sequence context.

Global alignments, which attempt to align every residue in every sequence, are most useful when the sequences in the query set are similar and of roughly equal size. (This does not mean global alignments cannot start and/or end in gaps.) A general global alignment technique is the Needleman—Wunsch algorithm, which may be used according to default parameters readily accessible to the skilled person.

Another suitable sequence alignment algorithm is, according to a particular embodiment, a string matching algorithm, such as KERR (Dufresne et al., Nature Biotechnology, Vol. 20, December 2002, 1269-1271). KERR computes the minimal number of differences between two sequences, by trying to optimally fit the shorter sequence into the longer one. KERR delivers the percent identity to the whole subject sequence. In this respect, it is preferred that identity percentages are calculated over the entire length of each of the compared sequences, In addition, or independently of any identity percentage with a sequence of reference, a peptidomimetic of the invention also encompasses a peptidomimetic having a sequence differing from the sequence of reference, especially SEQ ID NO: 1 or 2, by one or several conservative amino acid substitution(s), especially D-amino acid substitution(s). However, according to a particular embodiment, substitution(s) with L-amino acids may be contemplated, according to the conservation list provided below. Conservative substitutions encompass a change of residues made in consideration of specific properties of amino acid residues as disclosed in the following groups of amino acid residues and the resulting substituted peptidomimetic should not be modified functionally:

Acidic: Asp, Glu;
Basic: Asn, Gln, His, Lys, Arg;
Aromatic: Trp, Tyr, Phe;
Uncharged Polar Side chains: Asn, Gly, Gln, Cys, Ser, Thr, Tyr;
Nonpolar Side chains: Ala, Val, Leu, Ileu, Pro, Phe, Met, Trp;
Hydrophobic: Ile, Val, Leu, Phe, Cys, Met, Nor;
Neutral Hydrophilic: Cys, Ser, Thr;
Residues impacting chain orientation: Gly, Pro
Small amino acid residues: Gly, Ala, Ser.

By "one or several", it is meant any number consistent with the length of the peptidomimetic, and optionally consistent with the identity percentages defined above. According to a particular embodiment, by "several", it is meant 1, 2, 3, 4, 5, 6, 7, 8, 9, or 10.

In another embodiment, depending on the property(ies) guiding the choice for substitution of amino acid residue(s), modification of residue(s) can alternatively be determined to modify the properties of the resulting peptidomimetic, and said substitution(s) are selected to be non-conservative.

According to a particular embodiment, a peptidomimetic of the invention comprises or consists of SEQ ID NO: 1, or 2.

According to another aspect, the invention encompasses fragments of any one of the peptidomimetic sequences of the invention as defined herein. Accordingly, encompassed fragments are sequences fully constituted of D amino-acid residues.

By fragment, it is meant a fragment of contiguous amino-acid residues of at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or amino-acid residues, of the sequence of reference, The sequence of reference may be SEQ ID NO: 1 or 2 as defined herein, or a variant peptidomimetic as defined herein.

According to a particular embodiment, are encompassed peptidomimetics having a length of less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, or 11 amino acid residues, in particular peptidomimetics having a length between 10 and 50 amino-acid residues, or a length defined using any one of the preceding boundary values, in particular a length between 10 and 39, 40, 41 or 42 amino-acid residues.

Peptidomimetics of short length may be useful to bypass production difficulties, especially by solid phase synthesis. Accordingly, peptidomimetics of the invention encompass peptidomimetics obtained by shortening the amino-acid sequence of the reference sequence. According to a particular aspect, shorter peptidomimetics are encompassed to the extent that they keep the functional properties of the reference sequence, as defined herein. Advantageously, a short peptidomimetic of the invention might be 10, 11, 12, 13, 14, 15, 16, 17, 18, 19, 20 amino-acid long or 21, 22, 23, 24, 25, 26, 27, 28, 29, 30 amino-acid long.

According to a particular embodiment, when fragments or variants of a reference sequence are considered, such fragments or variants keep the functional properties of the reference sequence. For the purpose of the present paragraph discussed the functional properties of the reference sequence, such a reference sequence may be SEQ ID NO: 1 or 2, or the sequence of the prior art probes MUB40 #1 (SEQ ID NO: 3) as discussed in the introductory section and herein, when lactoferrin binding is contemplated.

The following functional properties have been defined as associated with the peptidomimetics of the invention, taken alone or in all combinations thereof:

a. the property to interact with, in particular to bind to, neutrophils and/or neutrophil granules, and/or
b. the property to interact with, in particular to bind to, proteins secreted by stimulated neutrophils, and/or
c. the property to interact with, in particular to bind to, lactoferrin, in particular neutrophil lactoferrin, especially neutrophil lactoferrin stored in neutrophil specific granules ($\beta$1) and/or tertiary granules ($\beta$2) and/or secreted by neutrophils, and/or
d. the property to interact with, in particular to bind to, globlet cells or goblet cell granules and/or
e. the property to interact with, in particular to bind to, Muc2 proteins, and/or
f. the property to interact with, in particular to bind to, mucus and/or airway sputum, in particular through Muc2 proteins, especially glycosylated Muc2 proteins found in mucus layers, for example adhesive mucus layers of a cell or tissue sample such as colonic or intestine tissue sample, and/or through lactoferrin, in particular neutrophil lactoferrin, and/or to interact with, in particular to bind to neutrophil containing secretions and/or fluids, especially through lactoferrin.

According to a particular embodiment, the peptidomimetics of the invention have the property to interact with, in particular to bind to, lactoferrin.

Lactoferrin is a 703-amino acid glycoprotein originally isolated from milk. The size and structure of lactoferrin are closely related to that of another group of iron-binding proteins, the so-called tranferrins. In humans, lactoferrin gene LTF is located on the third chromosome in the locus 3q21-q23. Lactoferrin consists of a single polypeptide chain folded into two homologous globular domains named N- and C-lobes, each with one iron binding site and one glycosylation site. The degree of glycosylation of the protein may be different and therefore the molecular weight of lactoferrin roughly varies between 76 and 83 kDa. Lactoferrin is a basic protein, with an isoelectric point at 8.7. Two forms co-exist: iron-rich hololactoferrin and iron-free apo-lactoferrin. Lactoferrin can exist in different polymeric forms ranging from monomers to tetramers, all of which are encompassed to define lactoferrin as a target, within the present invention. According to the present invention, lactoferrin is a protein having a molecular weight superior or equal to 70 kDa, in particular between 70 kDa and 85 kDa, more particularly between between 70 kDa and 80 kDa. It will be understood that encompassed lactoferrin isoform(s) and/or lactoferrin oligomerization state, according to which the molecular weight of lactoferrin can, possibly largely, exceed 70 kDa, do not limitatively define lactoferrin in the sense of the present disclosure.

Lactoferrin is in particular produced in neutrophils and stored in the so-called specific and tertiary granules. Of note, neutrophils are a major effector cell of innate immunity, acting in particular in the neutrophil-mediated inflammatory response. In response to infection, neutrophils leave the circulation and migrate towards inflammatory foci. This recruitment into inflamed tissues can be followed by a regulated exocytosis of granules and/or secretory vesicles. This exocytosis enables neutrophil to deliver its arsenal of potentially cytotoxic granule proteins in a targeted manner.

In fact, lactoferrin is a glycoprotein mostly found, in the sense it is found at concentrations within the mg/mL value range in animal body secretions (including mammals or humans), such as milk, tear fluid, and in neutrophil granules. Plasmatic concentrations of lactoferrin are much lower, i.e., within the µg/mL value range.

According to a particular embodiment, the peptidomimetics defined herein have the capability to bind to lactoferrin stored within neutrophil specific granules (β1) and/or tertiary granules (β2) as a definition of a protein secreted by stimulated neutrophils.

According to a particular embodiment, the peptidomimetics defined herein have the capability to bind to glycosylated lactoferrin, and/or interact with neutrophil lactoferrin as defined herein through glycosylated moieties.

Given their role in inflammatory responses, it is observed that the capacity to target neutrophils and/or neutrophil granules as disclosed herein, confer to the peptidomimetics of the invention a main interest as probes for investigating inflammation in tissues, and/or investigating through imagery diseases involving neutrophil-mediated inflammatory response, in vivo or in vitro, in this latter case through sampling.

Conversely, MUB70 (SEQ ID NO: 11) and MUB40 #1 (SEQ ID NO: 3) disclosed in WO 2013/034749 A1 have been shown to have the capacity to interact, in particular bind, with human colonic mucus through glycosylated Muc2 proteins. The colonic mucus is composed of two distinct layers; a firmly adherent layer associated to the epithelial surface and a loosely, more fluid, adherent one. The latter is probably the result of bacterial degradation and proteolysis. It is composed of 95% water and 5% mucin glycoprotein molecules, salt, immunoglobulins (IgA and IgG) and trefoil peptides. Among secreted mucins, the main gel forming molecules are Muc2, Muc5ac, Muc5b and Muc6 (expressed from chromosome 11p15.5), Muc2 is the predominant mucin in the colonic mucus layer and is highly glycosylated, allowing its protection from proteolysis in the lumen. Muc2 shows differential glycosylation profiles in the small intestine (ileum) and in the large intestine (colon) respectively enriched in sialylated and sulfated oligosaccharide species. Mucus production and composition modulations are commonly observed in the major inflammatory bowel diseases (IBD) like Crohn disease and ulcerative colitis. Specifically, Muc2 expression is upregulated in malignant tumors of a broad range of organs including lung, stomach, breast, prostate, bile ducts and colon. Detecting the nature and amount of mucus is important to envision the diagnostic and prognosis of various pathological conditions.

In this respect, the inventors demonstrated herein that colonic mucinous carcinoma, which was demonstrated to be specifically labelled with the original MUB70 peptide (SEQ ID NO: 11), was similarly labelled with MUB40 #1 (SEQ ID NO: 3), together with an anti-Muc2 antibody. The accumulation of Muc2 in this pathology was additionally confirmed. The inventors extended their investigations and also demonstrated in vitro that cystic fibrosis (CF) patients sputum was labeled with MUB40 #1-Cy5 (SEQ ID NO: 3), together with anti-Muc2 and anti-Muc5ac monoclonal antibodies, thereby potentially assessing a specificity of the interaction with Muc2 moieties. Since cystic fibrosis (CF) patients sputum is an inflammatory tissue in this context, therefore containing neutrophil, detection of neutrophils or targets detailed herein, which are found within neutrophils, may also be achieved using the peptidomimetics described herein.

Turning now to the functional properties of the peptidomimetics of the present invention, it is appreciated that they have, according to a particular embodiment, the property to interact, or bind, with mucus, especially human mucus, as defined herein.

Given the colloidal nature of mucus, the expression "interacts" used herein means that a peptidomimetic of the invention binds components of the mucus, or enters into close vicinity with such components when present in the mucus. Accordingly, in this context, the expression "interacts" is a synonym for "binds".

When used to define the interaction between peptidomimetic of the invention and neutrophils or proteins secreted by stimulated neutrophils or neutrophil granules, the expression "interacts" used herein means that a peptidomimetic of the invention binds a component found at the surface of neutrophils, or enters into close vicinity with such a component, as found within neutrophil granules as defined herein, in particular binds to such a component. The inventors have shown that such a component can be lactoferrin, as described according to the definitions provided herein.

According to a particular embodiment, peptidomimetics of the invention have the functional property to interact with, in particular to bind to, globlet cells or goblet cell granules.

Goblet cells are simple columnar epithelial cells that secrete gel-forming mucins. Distinct forms of mucin are produced in different organs: while MUC2 is prevalent in the intestine, MUC5AC and MUC5B are the main forms found in the human airway. Goblet cells are typically found in the respiratory, reproductive and gastrointestinal tracts and are surrounded by stratified squamous cells.

According to a particular embodiment, peptidomimetics of the invention have the property of interacting with one or several target(s) selected amongst those defined in points a. to f. above, for example: Muc2 protein-containing mucus, Muc2 protein(s) found in Muc2 protein-containing mucus, glycosylated Muc2 protein(s), especially glycosylated Muc2 protein(s) found in human colonic and/or intestinal mucus, more specifically sulfated moieties of glycosylated Muc2 protein(s), especially as found in human colonic and/or intestinal mucus, neutrophils, neutrophil granules, in particular neutrophil specific granules (β1) and/or tertiary granules (β2), lactoferrin, in particular neutrophil lactoferrin, especially neutrophil lactoferrin stored neutrophil specific granules (β(1) and/or tertiary granules (β2) and/or secreted by neutrophils, globet-cells, mucus, airway sputum, in particular through Muc2 proteins according to the definitions provided herein, and/or through neutrophil or neutrophil content according to the definitions provided herein. According to a particular embodiment, peptidomimetics of the invention can interact with, in particular can bind to, neutrophil containing secretions and/or fluids, especially through lactoferrin, as defined herein.

According to a particular embodiment, the one or several target(s) are glycosylated so that the interaction between said target(s) and the peptidomimetics of the invention occur through said glycosylation.

According to a particular embodiment, mucus is selected amongst: colonic, intestinal, respiratory tract, inflammatory, mucus from a tissue determined to be cancerous, mucus from a cell line.

According to a particular embodiment, mucus is human mucus.

When the mucus is an neutrophil-containing inflammatory mucus, interaction with the peptidomimetics of the invention can occur through Muc2 or glycosylated Muc2 as defined herein, or lactoferrin or glycosylated lactoferrin as defined herein, associated with neutrophils presence.

According to a particular embodiment, recognized Muc2 protein(s) moiety(ies), especially as found in a mucus as defined herein, is/are from human Muc2 protein.

According to a particular embodiment, peptidomimetics of the invention have the property of interacting with secretions, in particular as defined herein, which contain lactoferrin according to the definitions provided herein, and/or neutrophil granules as defined herein. According to a more particular embodiment, these secretions and neutrophil granules contain lactoferrin in a mg/mL value range of concentration (lactoferrin can be dosed, using conventional methods, within such as range in said secretions and/or neutrophil granules content).

According to a particular embodiment, recognized lactoferrin displayed or secreted by neutrophils, especially as found in an assayed or analyzed inflammatory tissue or fluid, is human.

According to a particular embodiment, peptidomimetics of the present invention interact with Muc2 protein(s) of human colonic, i.e. loose mucus layer or firm mucus layer, or intestinal mucus.

According to a particular embodiment, peptidomimetics of the present invention interact with glycosylated Muc2 protein(s) of human colonic or intestinal mucus.

According to a particular embodiment, peptidomimetics of the present invention interact with glycosylated Muc2 protein(s) through sulfated moieties of glycosylated Muc2 protein(s).

According to a particular embodiment, peptidomimetics of the present invention interact with glycosylated human, rabbit and guinea pig Muc2 protein(s) but not with murine glycosylated Muc2 protein(s).

According to a particular embodiment, peptidomimetics of the present invention interact with respiratory tract mucus, especially human respiratory tract mucus.

According to a particular embodiment, peptidomimetics of the present invention interact with Muc2 protein(s) of human respiratory tract mucus.

According to a particular embodiment, the interaction or binding is Muc2 specific.

"Muc2 specific" relates to the fact that the peptidomimetic(s) of the invention do(es) not interact or not significantly interact with other secreted gel-forming mucins, taken alone or according to any combination between them, said other secreted gel-forming mucins including for example Muc5ac, Muc5b or Muc6.

According to another or cumulative particular embodiment, the interaction or binding is lactoferrin specific, in particular glycosylated lactoferrin specific.

According to another aspect, peptidomimetics of the present invention can have, alone or in combination with other functional property(ies) as detailed herein, the property to bind neutrophil granules, especially trough lactoferrin and/or Muc2 binding.

Neutrophil granules can be from fixed or living neutrophils.

Neutrophils can be human.

Neutrophils can be stimulated or not.

Regarding neutrophil assays, reference is made to the functional studies of human neutrophils described in Monceaux et al, Blood, Volume 128, Number 7, 993-1002, 2016, in particular the Material and Methods section, which is incorporated by reference herein. More particularly, the skilled person can refer to this publication for guidance regarding human blood collection, neutrophil isolation protocol, suitable neutrophil condition medium, as made available in this reference.

Since it was found that, according to a particular embodiment, peptidomimetics of the present invention target components found at the level of neutrophil granules, incubation of the peptidomimetics with living neutrophils in particular in vitro, or analysis of fixed neutrophils in particular in vitro, therefore also allows the detection of degranulation events.

According to a preferred embodiment, peptidomimetics of the present invention may have, alone or in combination with other functional property(ies), the property to interact, in particular to bind, with Muc2 containing mucus and/or lactoferrin containing neutrophils.

According to another embodiment, a peptidomimetic of the invention has the capacity to adopt a multimeric, especially a trimeric, organization and/or is found as a trimer, in particular in a phosphate buffer.

Determination of multimeric organization can be made by comparing the peptidomimetic, the multimeric or monomeric status of which has to be determined, to its theoretical molecular weight.

According to a particular embodiment, a peptidomimetic of the invention has an additional Cysteine residue at its N-terminal extremity, which can be, according to a particular embodiment, a D-Cysteine residue, or a L-Cysteine residue. Accordingly, the length of the overall peptidomimetic takes into account this additional amino acid residue, D or L, and is increased by one further amino acid residue. For instance, SEQ ID NO: 2 is 41 D-amino acids long. The presence of a free Cysteine residue may be of interest to enable attachment of additional moieties, especially markers or labels or other active groups.

According to a particular embodiment, a peptidomimetic of the invention is fully constituted of D amino acid residues, including the additional Cysteine residue at its N-terminal extremity, when present.

However, according to another particular embodiment, no specific amino-acid residue is required at the N-terminal extremity of a peptidomimetic of the invention to achieve attachment of additional moieties, since any amino-acid carboxy group or another chemical group of a peptidomimetic of the invention can be used to this end.

According to a particular embodiment, a peptidomimetic of the invention has its N- and/or C-terminal amino-acids modified, for example by amidation, acetylation, acylation or any other modification known in the art. According to a particular embodiment, a peptidomimetic of the invention has an amide group at its C-terminus and/or an acetyl group at its N-terminus. These groups are mostly used in Solid-Phase-Peptide-Synthesis (SPPS) because readily accessible and with minimal steric hindrance effect. The skilled person can however easily adapt and modify the N- and/or C-terminal amino-acids according to a preferred synthesis protocol, following the guidance readily available to him/her and in the literature in the field of SPPS. Nonetheless, it will be understood that any group(s) serving the same purpose as said amide and/or acetyl groups can be used within the present invention.

According to a particular embodiment, a peptidomimetic of the invention has an improved resistance to protease degradation (or stability) with respect to its L-peptide counterpart, as evaluated through a trypsin digestion method, in particular as illustrated in the Examples section herein, with respect to RI-MUB40 (SEQ ID NO: 2). The L-peptide counterpart to RI-MUB40 (SEQ ID NO: 2) is MUB40 #1 (SEQ ID NO: 3) as defined in WO 2013/034749 A1. Accordingly, these two peptides are compared for evaluating resistance to protease degradation. The skilled person knows how to adapt the experimental conditions to retrieve exploitable and comparative data, for example following the guidance and protocol provided in the Examples section herein, in this respect. "Improved" means that within similar detection conditions, less or no enzymatic degradation can be observed for a peptidomimetic of the invention, with respect to a non-peptidomimetic corresponding molecule, such as Mub40 #1, after a certain amount of time, e.g., 3 hours, and up to 24 hours.

For example, in the Example section herein, MUB40 #1 (SEQ ID NO: 3) was almost completely degraded within 3 h, whereas no degradation was observed for the RI-MUB40 D-peptide (SEQ ID NO: 2) until 24 h.

According to a particular embodiment, a peptidomimetic of the invention has an enhanced stability with respect to its L-amino acids counterpart. According to a particular embodiment, a peptidomimetic of the invention is not degraded in the presence of protease(s). The skilled person can readily determine encompassed protease(s), on the basis of his/her knowledge and as documented in the literature available so far. A particular degradation testing example in provided in the Experimental section herein, the experimental conditions of which can be readily adapted by the skilled person to define the resistance to degradation properties of the peptidomimetic of the invention.

According to another aspect, a peptidomimetic of the invention can be:
  labelled, especially by coupling with a fluorophore, such as such as Cy5, Cys5.5 (suffix—Cy5 herein) or a biotin, and/or
  associated with a reporter or a carrier entity, and/or
  associated with an active molecule such as a drug or an enzyme, or fragments thereof.

Coupling procedures with a fluorophore or a biotin can be performed as usual in the field. Particular examples are provided in the Experimental section herein. The skilled person knows how to adapt the procedure to other fluorophores.

Examples of other appropriate tags/labels may be selected among the groups comprising biotin, fluorescent dyes for example rhodopsine, alexa-Fluor, nanogold coated ligands, carbon-black coated ligands, mangradex, fluorescent ligand such as fluorochromes, or radioactive molecules, for example comprising radioactive atoms for scintigraphic studies such as $^{123}$I, $^{124}$I, $^{111}$In, $^{186}$Re, $^{188}$Re.

According to a particular embodiment, an active molecule can be anti-inflammatory molecule(s) or mucolytic molecule(s), such as acetylcysteine, bromalaine, human DNase I or bacterial mucinase(s). Mucolytic molecules are especially relevant in a cystic fibrosis context.

By "associated" it is meant, in particular, grafting, or covalent binding.

According to a particular embodiment, the invention enables the detection or the monitoring of neutrophil production and/or neutrophil composition, and/or neutrophil, especially specific neutrophils which can be marked according to the present invention, degranulation events in human or animal body(ies) or tissues. The invention also enables the monitoring of neutrophil recruitment events.

According to a particular embodiment, the invention enables the detection or the monitoring of mucus production and/or mucus composition in human or animal body(ies), or cell(s), especially the detection or the monitoring of human colonic or intestinal mucus or human respiratory tract mucus, or human inflammatory mucus or inflamed tissue, especially where lactoferrin can be found, or mucinous carcinoma tissue(s) or tissues in which a neutrophilic inflammation is taking place or susceptible of taking place, or associated with the occurrence or possibility of occurrence of a neutrophilic inflammation.

According to a particular embodiment, the invention makes use of labeled peptidomimetics as probe(s), especially as physiological labeled probe(s) for staining the targets identified herein, especially when contained in mucus layer(s) of cell or tissue sample(s), and/or associated with neutrophil activity.

According to a particular embodiment, the invention enables the detection or the monitoring of lactoferrin as found in the secretion(s) and/or neutrophils and/or neutrophil granules as defined herein. Accordingly, the invention enables the detection or the monitoring of neutrophilic inflammation, i.e., inflammation associated with neutrophil recruitment. According to a particular embodiment, the invention makes use of labeled peptidomimetics as probe(s), especially as physiological labeled probe(s) for staining the targets identified herein, especially when contained in secretions and/or neutrophil granules as defined herein.

According to a particular embodiment, the invention makes use of labeled peptidomimetics as probe(s), especially for staining fixed or living neutrophil(s), as defined above. Staining living neutrophil(s) is preferably achieved in vitro. In vivo experiments may be contemplated in animals, as shown in the Experimental Section herein.

According to a particular embodiment, the invention makes use of labeled peptidomimetics as probe(s), especially for staining material secreted by stimulated neutrophils, as defined above, in particular lactoferrin as described herein, in fixed or living experiments. Staining living neutrophil(s) is preferably achieved in vitro. In vivo experiments may be contemplated in animals, as shown in the Experimental Section herein The invention is therefore of particular interest in experiments aimed at highlighting events potentially associated with, or assessing the presence of a neutrophilic inflammation, in particular using imaging methods conventionally used in the art.

Since Muc2 proteins are also expressed in other tissues of the human body than colonic or intestinal mucus, either when said tissues are in a healthy state or to the contrary when they reflect a pathological state, the peptidomimetics of the invention may be used for detection or monitoring of mucus production and/or composition, in other tissues such as lung tissue or epithelial tissue.

Since neutrophils are involved in neutrophil-mediated inflammatory responses, the peptidomimetics of the invention may be used for detection or monitoring of neutrophil-mediated inflammation events in all inflammatory diseases which can be associated with neutrophil recruitment, let it be the result of acute inflammatory events or chronic inflammatory events, in tissue susceptible of being affected by such an inflammation, or tissue actually found affected by such an inflammation, for example on the basis if phenotypic symptoms, or on the basis of the assessment of other biological markers known to be associated with an inflammation state, according to the knowledge of the skilled person.

According to a particular embodiment, such detection or monitoring of neutrophil-mediated inflammation events can be achieved through lactoferrin binding, as discussed herein, especially binding of peptidomimetics of the invention to glycosylated lactoferrin.

According to a particular embodiment, the invention enables the detection or the monitoring of mucus production and/or mucus composition in human or animal body(ies), especially the detection or the monitoring of human colonic or intestinal mucus, or human respiratory tract mucus.

According to a particular embodiment, the invention enables the detection or the monitoring of inflammation events associated with neutrophil recruitment in human or animal body(ies), in particular the detection or the monitoring of human colonic or intestinal mucus inflammation state, or human respiratory tract mucus inflammation state. Such an inflammation state can result from a bacterial or pathogen infection, or from all conditions leading to an acute or chronic neutrophil mediated inflammation in a body or tissue.

According to a particular embodiment, the invention makes use of labeled peptidomimetics as probe(s), especially as physiological labeled probe(s) for staining Muc2 protein(s) contained in mucus layer(s) of cell or tissue sample(s), and/or for staining neutrophils and/or lactoferrin according to the definitions provided herein with respect to the targets of the peptidomimetics of the invention.

The invention accordingly also relates to a peptidomimetic of the invention for use in a method of investigation in vivo of the presence of a neutrophilic inflammation and/or presence of Muc2 protein(s) in secretions and/or tissues, assayed by imaging methods. The skilled person can, upon analysis of the results of the imaging method(s) carried out, investigate whether a neutrophilic inflammation and/or Muc2 protein(s) can be seen, especially detected, according to his/her knowledge.

The invention also relates to a method for in vitro/ex vivo investigating the presence of a neutrophilic inflammation and/or presence of Muc2 protein(s) in secretions and/or tissues, assayed by imaging methods, wherein said secretions and/or tissues are contacted with a peptidomimetic of the invention.

The invention also relates to the use of a peptidomimetic of the invention as agents for imaging secretions and/or tissues as defined herein, especially for investigating the presence of a neutrophilic inflammation and/or presence of Muc2 protein(s), in particular detecting neutrophilic inflammation and/or Muc2 protein(s), or events associated with the same.

Accordingly, the invention also relates to the use of a peptidomimetic of the invention as a neutrophilic inflammation marker, according to any one of the embodiments described herein.

The peptidomimetics and molecules of the invention can be prepared by conventional routes, in particular chemically synthesized by solid phase synthesis, according to conventional practice.

The peptidomimetics of the invention may accordingly be produced by chemical synthesis (e.g., solid-phase peptide synthesis), using conventional methods well known in the art. D-polypeptides can be readily synthesized by manual and automated solid phase procedures well known in the art. Suitable syntheses can be performed for example by utilizing "t-Boc" or "Frnoc" procedures. Techniques and procedures for solid phase synthesis are described in for example Solid Phase Peptide Synthesis: A Practical Approach, by E. Atherton and R. C. Sheppard, published by IRL, Oxford University Press, 1989. Alternatively, the peptides may be prepared by way of segment condensation, as described, for example, in Liu et al., Tetrahedron Lett. 37: 933-936, 1996; Baca et al, J. Am, Chem, Soc. 117: 1881-1887, 1995; Tam et al., Int. J. Peptide Protein Res, 45: 209-216, 1995; Schnolzer and Kent, Science 256: 221-225, 1992; Liu and Tarn, J. Am. Chem. Sα, 116: 4149-4153, 1994; Liu and Tarn, Proc. Natl. Acad. Sci, USA 91; 6584-6588, 1994; and Yamashiro and Li, Int. J, Peptide Protein Res. 31: 322-334, 1988). Other methods useful for synthesizing the peptides are described in Nakagawa et al., J. Am. Chem. Sα, 107: 7087-7092, 1985. Adaptation of such protocols to D-polypeptides synthesis can readily be achieved by the skilled person.

In a particular embodiment, where the synthesized peptidomimetic encompasses the D-amino acid residues found at positions 31 and 32 by reference to the N-terminus of SEQ ID NO: 2, the synthesis method can be performed by a Solid-Phase Synthesis method which includes:
  a step of sequential incorporation of Fmoc-D-Gly-OH and Fmoc-D-Asp(OtBu)-OH aminoacids, or
  a step of coupling with a Fmoc-D-Asp(OtBu)-(Hmb)Gly-OH dipeptide when the synthesis reaches position 31 by reference to the N-terminus of SEQ ID NO: 2.

An exemplary albeit typical synthesis method is illustrated in the examples and can be similarly used for other peptidomimetics having analogous amino-acid composition, in particular peptides shorter than the RI-MUB40 peptidomimetic (SEQ ID NO: 2) and having at least partly an amino-acid composition that is analogous to the MUB40 peptidomimetic (SEQ ID NO: 2).

The invention also relates to composition(s) comprising peptidomimetic(s) of the invention, including under a salt form, in particular pharmaceutical composition(s) when the peptidomimetic(s) is/are associated with an active ingredient having a therapeutic effect, said composition comprising if necessary pharmaceutically acceptable excipient(s), such as carrier(s) and/or adjuvant(s), optionally in an appropriate buffer.

The invention also relates to a peptidomimetic as defined herein, in particular when associated, especially coupled or conjugated, with an active molecule such as a drug or an enzyme as defined herein, or a composition encompassing the same, for use as a medicament or in a method of therapy, especially a method of therapy of a human, or for use as an inflammation marker or a neutrophilic inflammation marker.

Such as medicament may be suitable for administration to a subject in need thereof, in treating a disease selected from the following group, or its symptom(s): disease, condition or health state associated with neutrophil-mediated inflammation or associated with neutrophil recruitment, neutrophilic inflammation, neoplasic disease(s), including mucinous carcinoma(s), gastric cancer(s) or colorectal cancer(s), especially colon cancer(s), cystic fibrosis, intestine inflammatory disease(s) such as inflammatory bowel disease (IBD) and ulcerative colitis, bacterial and/or pathogen infections.

Accordingly, the invention also relates to a method for manufacturing a medicament comprising a step of association, especially coupling, grafting or fusing a peptidomimetic according to the present description with a biologically active molecule such as a drug or an enzyme.

Such a therapeutic peptidomimetic, or composition or medicament resulting from the above can be used in a method of therapy practised on a human or animal body, in particular for use in treating a disease selected from the following group, or its symptom(s): disease, condition or health state associated with neutrophil-mediated inflammation or associated with neutrophil recruitment, neutrophilic inflammation, neoplasic disease(s), including mucinous carcinoma(s), gastric cancer(s) or colorectal cancer(s), especially colon cancer(s) (but also lung, stomach, breast, prostate, or bile ducts cancers), cystic fibrosis, intestine inflammatory disease(s) such as inflammatory bowel disease (IBD) and ulcerative colitis, bacterial and/or pathogen infections.

According to a particular embodiment, the invention also relates to the use of a peptidomimetic as defined herein, as a probe or marker for staining living cell(s), including neutrophils, or tissue(s) or proteins secreted by stimulated neutrophils, especially as defined herein (e.g., lactoferrin), in in vitro experiments, in particular in live microscopy experiments.

According to a particular embodiment, the invention also relates to the use of a peptidomimetic as defined herein, as a probe or marker in the investigation, in particular detection/assessment of neutrophilic inflammation, and/or an inflammatory state or disease, in particular through imagery, in in vitro (or ex vivo or in vivo) experiments on the basis of a sample recovered from a subject in need of such an assessment/evaluation.

Live microscopy encompasses for example the use of widefield microscopy on living cells (for example HT29-MTX cells stained with Cy5-MUB$_{70}$), 2-photons microscopy (for example on human colon ex vivo sample stained with Cy5-MUB$_{70}$), or 3D animal analysis (Xenogen, Ivis, Cy5-MUB$_{70}$), (Fluoptics, Cy5.5-MUB$_{70}$), or spectral imaging (for example: coloscopy).

The invention also relates to the use of a peptidomimetic as defined herein, as a probe or marker for staining mucus, and/or Muc2 protein(s) contained in mucus layer(s), especially in adhesive mucus layers, of a cell or tissue sample, especially colonic or intestine or respiratory tract tissue sample, or neutrophils, especially neutrophil granules, or proteins secreted by stimulated neutrophils, such as lactoferrin. According to a particular embodiment, biological tissue(s) or fluids or the like are provided ex vivo. According to a particular embodiment, staining, especially cell(s) or neutrophil granules, is achieved in vitro.

The invention also relates to the use of peptidomimetics as defined herein, or a composition as defined herein:
as a physiological labelled probe to detect in vitro interaction with human colonic mucus in the adhesive mucus layer of colonic tissue sample, or more generally with mucus as defined herein, and/or to detect in vitro interaction with goblet cells, or
to detect in vitro mucus production or mucus composition in human colon, said use comprising contacting said peptidomimetic with a sample of colonic tissue comprising adhesive mucus layer and goblet cells, and optionally and detecting stained mucus, or
for in vitro detecting or monitoring any one of the following disease conditions: disease, condition or health state associated with neutrophil-mediated inflammation or associated with neutrophil recruitment, neutrophilic inflammation, neoplasic disease(s), including mucinous carcinoma(s), gastric cancer(s) or colorectal cancer(s), especially colon cancer(s), cystic fibrosis, intestine inflammatory disease(s) such as inflammatory bowel disease (IBD) and ulcerative colitis, bacterial and/or pathogen infections.

According to another aspect, it has been ascertained that the peptidomimetics described herein have the following property: they do not cross plasma membranes. This has been shown for the RI-MUB40 peptide (SEQ ID NO: 2) of the Examples section. Accordingly, and according to a particular embodiment, the peptidomimetics of the invention are non-toxic to cells.

According to a particular embodiment, polypeptide(s) of the invention is/are not toxic to cells. Non-limitative examples of cells that might be impervious to the polypeptides of the invention are epithelial cells, especially human epithelial cells, myeloid cells, especially human myeloid cells, Embryonic Stem (ES) cells, especially human Embryonic Stem (ES) cells, dendritic cells.

The invention also relates to a peptidomimetic as defined herein, which is labelled, for use as a probe for in vivo detection of mucus production or mucus composition in human colon or respiratory tract mucus.

In another particular embodiment, the invention relates to a peptidomimetic as defined herein, which is labelled, for use as a probe for in vivo detection of mucus production or mucus composition in human intestine, especially colon or other compartments such as lung tissue, nasal tissue, respiratory tract or stomach tissue.

The invention therefore generally relates to the use of a peptidomimetic or a composition comprising the same, as a probe for staining mucus potentially containing Muc2 protein(s) or exhibiting variations in Muc2 protein(s) expression that could provide information on a change in mucus production or in mucus composition.

According to a particular embodiment, the observed mucus is colonic mucus, for example in human, rabbit or guinea pig samples as well as human cell lines producing a mucus layer samples.

According to a particular embodiment, the observed mucus is human colonic carcinoma mucus.

According to a particular embodiment, the observed mucus is from a patient diagnosed with cystic fibrosis, and is mucus isolated from its respiratory tract.

According to a particular embodiment, stained mucus-producing cells are eukaryotic cell(s), including intestine mucus cells, such as goblet cells.

Detection in vitro of mucus production or mucus composition in human colon or respiratory tract might serve as a basis for comparisons between samples, and therefore might serve to analyse or detect or monitor variations or modulations of mucus production or mucus composition in an human or animal body. With this respect, it has been observed that Muc2 protein is naturally expressed and secreted in intestine mucus as a major component of said mucus in healthy tissue, especially in healthy colonic tissue. It has also been observed that Muc2 protein is not expressed in healthy trachea or lung tissues, and in healthy stomach tissues. A change in Muc2 expression in these tissues may thus provide information on the tissue status.

Muc2 expression modulation is also observed in gastric cancer (increased), in ductal adenocarcinoma, in cystic fibrosis (increased), in cystic fibrosis transmembrane conductance regulator model, especially with respect to lung tissues, nasal tissue, goldbladder tissue, pancreas tissue. Muc2 expression modulation is also observed in Inflammatory Bowel Diseases (IBD) such as ulcerative colitis and Crohn disease.

Also, Muc2 glycosylation profile is modulated in colonic diseases such as ulcerative colitis or colorectal carcinoma.

The invention also relates to peptidomimetic as defined herein, which is labelled, for use as a probe for in vivo detection or the monitoring of lactoferrin as found in the secretion(s) and/or neutrophils and/or neutrophil granules as defined herein. According to a particular aspect, the invention enables the detection or the monitoring of neutrophilic inflammation, i.e., inflammation associated with neutrophil recruitment.

Another object of the invention is the use of a peptidomimetic or of a composition of the invention for in vitro detecting or monitoring any one of the following disease conditions: disease, condition or health state associated with neutrophil-mediated inflammation or associated with neutrophil recruitment, neutrophilic inflammation, neoplasic disease(s), including mucinous carcinoma(s), in particular colonic mucinous carcinoma(s), gastric cancer(s) or colorectal cancer(s), especially colon cancer(s), (but also lung, stomach, breast, prostate, or bile ducts cancers) cystic fibrosis, intestine inflammatory disease(s) such as inflammatory bowel disease (IBD) and ulcerative colitis, bacterial and/or pathogen infections.

However, according to another specific embodiment, the invention is also directed to the use of a peptidomimetic of the invention, in particular RI-MUB40 peptidomimetic (SEQ ID NO: 2) or peptidomimetic sharing identity with RI-MUB40 (SEQ ID NO: 2), or fragments thereof, as marker of neutrophil granules (thereby for neutrophils detection), or a marker of degranulation event(s) in neutrophils, especially an in vitro marker of neutrophil granules or marker of degranulation event(s) in neutrophils, or a marker of neutrophilic inflammation.

According to another specific embodiment, the invention is also directed to the use of a peptidomimetic of the invention, in particular RI-MUB40 peptidomimetic (SEQ ID NO: 2) or peptidomimetic sharing identity with RI-MUB40 (SEQ ID NO: 2), or fragments thereof, as marker of proteins secreted by stimulated neutrophils (thereby for inflammation event detection or monitoring), especially an in vitro marker of proteins secreted by stimulated neutrophils, from fixed or living samples containing such stimulated neutrophils appropriately recovered.

Neutrophilic inflammation can be appreciated by reference to the knowledge of the skilled person in the art. Neutrophils are main actors of inflammation events, and inflammation contributes to the pathophysiology of numerous diseases or symptoms. Increased presence of neutrophils may be associated with occurrence (undesirable) physiologic or pathologic symptoms and manifestations. Means described herein offer to the skilled person relevant tools for investigating the presence of a neutrophilic inflammation by reference to standard(s) in the art, when neutrophils are involved.

It is observed that labelled peptidomimetics of the invention have been shown to advantageously enable revealing neutrophil degranulation for the first time in inflammatory tissues in vivo with a non-invasive method, in a way where the intensity of fluorescent signal correlated with inflammation severity, suggesting that binding of the peptidomimetics of the invention to their target(s) may not only be a marker for inflammation in vivo, but also a marker enabling quantitative assessment of inflammation intensity. Accordingly, the peptidomimetics described herein promise to be outstanding tools in inflammation-imaging methods, especially such methods based on lactoferrin detection.

A method as described herein is deemed non-invasive when the peptidomimetic of the invention is contacted with the tissue to be assayed or administered to the body to be investigated using conventionally used methods that are not harmful to the assayed body. Accordingly, the peptidomimetic of the invention can be administered systemically, such as through oral administration (systemic administration is a route of administration of a substance into the circulatory system so that the entire body is affected), or through conventional intra-vascular or intra-venous administration.

According to a more particular embodiment, the use defined in the above paragraph is achieved through lactoferrin binding, in particular glycosylated lactoferrin binding, according to any one of the embodiments described herein.

The invention also relates to the use of a polypeptide comprising or consisting of:
a. SEQ ID NO: 3, or
b. a fragment of at least 20 contiguous amino-acid residues of SEQ ID NO: 3, or
c. a variant of SEQ ID NO: 3 or a fragment of at least 20 contiguous amino-acid residues of SEQ ID NO: 3, which has at least 75% identity with SEQ ID NO: 3,
d. any one of the sequences defined in a., b., or c., with an additional cysteine residue at its N-terminus, wherein the polypeptide has a length between 20 and 50 amino-acids residues, and optionally is coupled to a labelling moiety, as a probe or marker for staining lactoferrin, in particular neutrophil lactoferrin, especially neutrophil lactoferrin stored in neutrophil specific granules (β1) and/or tertiary granules (β2) and/or secreted by neutrophils.

It is observed that SEQ ID NO: 3 can be defined without its Cysteine residue at its N-terminal extremity.

According to a particular embodiment, said use referred to above relates to the use of a polypeptide as an in vitro or ex vivo probe or marker.

According to a particular embodiment, said use referred to above relates to a polypeptide for use as an in vivo probe or marker.

Through staining, the use referred to above also concerns investigation of neutrophilic inflammation, according to any one of the embodiments described herein, including for peptidomimetics of the invention.

It is observed that SEQ ID NO: 3 contains L amino acid residues. Accordingly, in a particular embodiment, fragments and variants thereof fully encompass L amino acid residues.

According to another particular embodiment however, fragments and variants defined with respect to SEQ ID NO: 3 encompass polypeptides which partly comprises or includes D amino acid residues, in an amount consistent with the identity percentages defined herein, with respect to "variants" or "substitutions". Accordingly, a polypeptide defined by reference of SEQ ID NO:3, the use of which is described above, can contain a mixture of L- and D-amino acids, to the proviso that the functional properties defined herein for the peptidomimetics are kept.

The modification(s) defining the variant polypeptide can independently be deletion(s), including especially point deletion(s) of one or many L-amino acid residue(s) or can be substitution(s), especially conservative substitution(s) of one or many L-amino acid residue(s). Substitutions can be achieved with L amino acids residue(s) or D amino acid residue(s).

Definitions provided herein with respect to peptidomimetics length and/or percentage of identity and/or substitutions possibilities and/or additional moieties coupled or grafted to the main sequence, also apply to polypeptide fragments and variants of SEQ ID NO: 3 discussed in the paragraphs above.

Other examples and features of the invention will be apparent when reading the examples and the figures, which illustrate the experiments conducted by the inventors, in complement to the features and definitions given in the present description.

LEGEND OF THE FIGURES

FIG. 1. $MUB_{40}$, derived from $MUB_{70}$ (SEQ ID NO: 11), binds to the human colonic mucus and neutrophil granules (A) Schematic representation of the four 40-amino acid peptides named $MUB_{40}$#1 (SEQ ID NO: 3), $MUB_{40}$#2 (SEQ ID NO: 4), $MUB_{40}$#3 (SEQ ID NO: 5), $MUB_{40}$#4 (SEQ ID NO: 6), overlapping and covering the $MUB_{70}$ sequence (SEQ ID NO: 11) (Coïc et al., 2012) (from C-terminal to N-terminal, see FIG. 2). (B) Human colonic mucus layer was labelled with the $MUB_{40}$#1 (SEQ ID NO: 3)-Cy5 fluorescent conjugate (1 µg/mL, magenta). Actin (red); bar, 10 µm; not $MUB_{40}$#2-#4 peptides conjugated to Cy5 (shown in FIG. 2B). (C) Colonic goblet cell granules were labelled with $MUB_{40}$#1 (SEQ ID NO: 3)-Cy5 (1 µg/mL, magenta), which was not the case for MUB70 (SEQ ID NO: 11)-Cy5 (Coïc et al., 2012) or $MUB_{40}$#2-#4 peptides (SEQ ID NOS: 4-6) (data not shown). Actin (red); bar, 20 µm. (D) Elution profiles of $MUB_{40}$ peptides (#1-#4) (SEQ ID NOS: 3-6) were obtained by analytical gel filtration (absorbance at 280 nm). Samples were prepared at 10 µg/ml in the elution buffer (20 mM phosphate buffer, 150 mM NaCl, pH7.4). $MUB_{40}$#1 (SEQ ID NO: 3) assembled as a trimer, similarly to MUB70 (SEQ ID NO: 11) (Coïc et al., 2012), not $MUB_{40}$#2 (SEQ ID NO: 4), $MUB_{40}$#3 (SEQ ID NO: 5), and $MUB_{40}$#4 (SEQ ID NO: 6). The relative masses (15.9; 22.0; 20.5 and 20.4 respectively) were estimated from standard proteins' elution volume (as indicated). (E) Far-UV Circular Dichroism spectra of the four $MUB_{40}$ peptides (SEQ ID NOS: 3-6) at 60 µM in 20 mM sodium phosphate buffer (pH 7.4) in the presence of 50 mM NaCl, showing a specific structural signal of $MUB_{40}$#1 (SEQ ID NO: 3), compared to others peptides. (F) A human colonic explant was infected with *Shigella flexneri* pGFP (green) and labelled with $MUB_{40}$#1 (SEQ ID NO: 3)-Cy5 (1 µg/mL, magenta) and Dapi (blue) after fixation and permeabilization. The colonic mucus layer and infiltrated neutrophils (see (G)), were labelled with $MUB_{40}$#1 (SEQ ID NO: 3)-Cy5, as imaged by two-photon microscopy. Bar, 50 µm (G) The labelling of polymorphonuclear neutrophils with $MUB_{40}$#1 (SEQ ID NO: 3)-Cy5 (1 µg/mL, magenta) was confirmed on human purified neutrophils, showing a granular staining. Nucleus was stained with Dapi (blue). Bar, 5 µm.

FIG. 2. $MUB_{40}$ peptides sequence and colonic mucus binding property (a) Operational sequences for the syntheses of $MUB_{40}$#1 (SEQ ID NO: 3), $MUB_{40}$#2 (SEQ ID NO: 4), $MUB_{40}$#3 (SEQ ID NO: 5), $MUB_{40}$#4 (SEQ ID NO: 6), where the where secondary amino acid surrogates are underlined (pseudoproline dipeptides) or in bold (Dmb dipeptides). Prolines are in italic bold. (b) As described in FIG. 1*b* with $MUB_{40}$#1 (SEQ ID NO: 3)-Cy5, Human colonic mucus layer was labelled with the $MUB_{40}$#2 (SEQ ID NO: 4)-Cy5, $MUB_{40}$#3 (SEQ ID NO: 5)-Cy5, and $MUB_{40}$#4 (SEQ ID NO: 6)-Cy5 fluorescent conjugate (1 µg/mL, magenta). Actin (red); bar, 10 µm.

Figure 3:
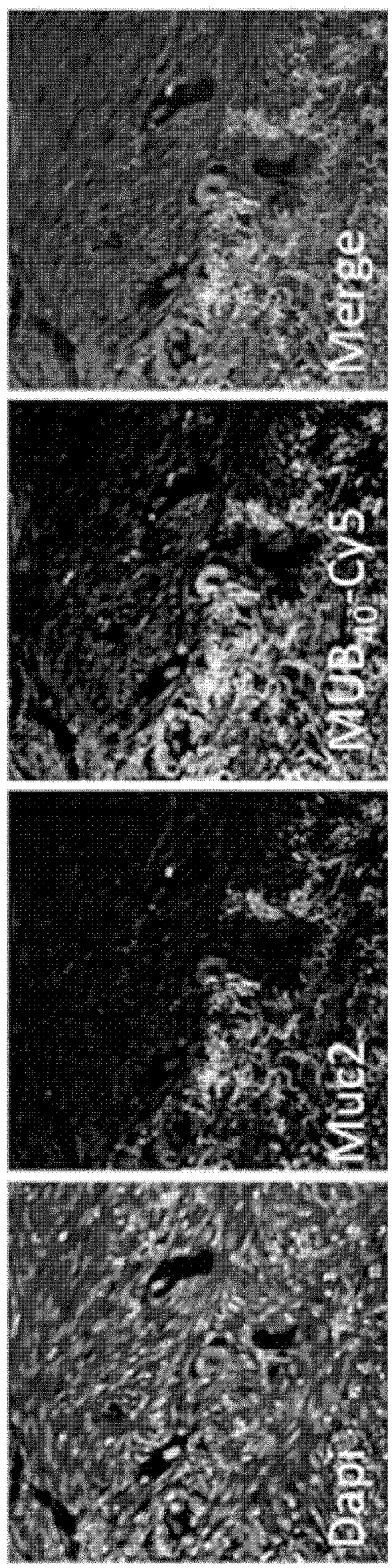

FIG. 3. Mucinous carcinoma immunofluorescent staining with MUB40 #1 (SEQ ID NO: 3)-Cy5 (MUB40-Cy5) and anti-Muc2 antibody (with a secondary antibody conjugated with FITC).

Muc2 was stained with an anti-Mucin2 antibody (green). Tissue was additionally stained with $MUB_{40}$-Cy5 (1 µg/mL, magenta). DNA was stained with Dapi (blue).

Figure 4:
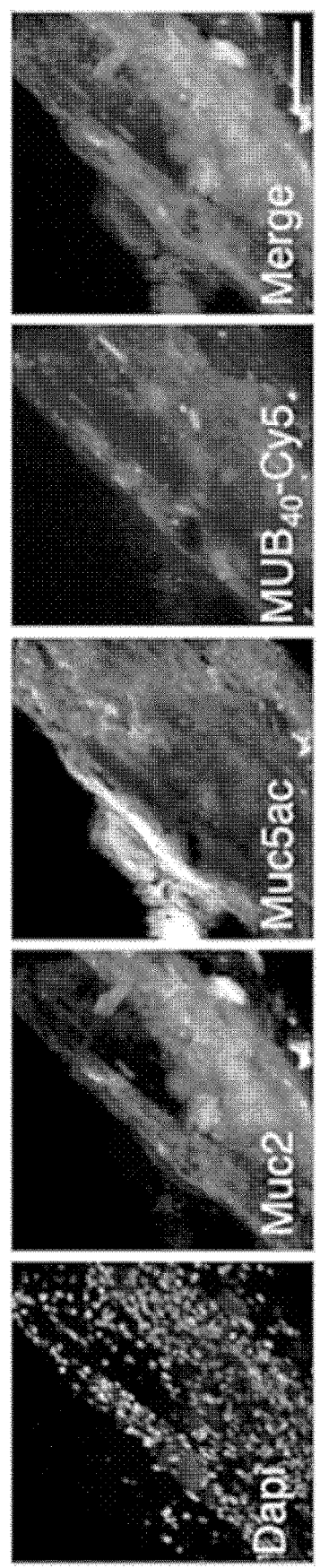

FIG. 4. CF patient sputum immunofluorescent staining with MUB40-Cy5 (SEQ ID NO: 3), anti-Muc2 and anti-Muc5ac antibodies (with secondary antibodies conjugated with FITC and Rhodamin respectively).

Muc2 was stained with an anti-Mucin2 antibody (green). Muc5ac was stained with an anti-Mucin5ac antibody (red). Tissue was additionally stained with $MUB_{40}$-Cy5 (1 µg/mL, magenta). DNA was stained with Dapi (blue).

FIG. 5. Mature myeloid cells were specifically labelled with $MUB_{40}$#1 (SEQ ID NO: 3)-Cy5 (hereafter named $MUB_{40}$-Cy5)

(A) Human polymorphonuclear neutrophils were similarly labelled with $MUB_{40}$ (SEQ ID NO: 3) conjugated with Cy5 (magenta) or Alexa405 (blue) and with a retro-inverso (RI) $MUB_{40}$ peptide, designed with non-natural D-amino acids (SEQ ID NO: 2), conjugated with Cy5 (magenta). Nuclei were stained with Dapi (blue or white). Bars, 20 µm. (B) Human hematopoietic stem cells (CD34+) were not labelled by $MUB_{40}$ (SEQ ID NO: 3)-Cy5 during their proliferation, when a positive staining (magenta) was obtained upon their differentiation in polymorphonuclear neutrophils in the presence of G-CSF, IL-3, and IL-6 (2 weeks). Nuclei were stained with Dapi (blue). Bars, 50 µm. (C-D) RI-$MUB_{40}$ peptide (SEQ ID NO: 2) was not degraded by trypsin. (C) $MUB_{40}$ (SEQ ID NO: 3) and RI-$MUB_{40}$ (SEQ ID NO: 2) final peptide concentration was 0.25 mg/mL and trypsin to protein ratio was 1:20 (w/w). HPLC profiles of purified $MUB_{40}$ (SEQ ID NO: 3) and RI-$MUB_{40}$ (SEQ ID NO: 2) peptides incubated with Trypsin during the 0, 1, 3, and 24 h at 37° C. The percentage of peptide stability over the time are shown in (D). Results are expressed with Mean±S.D. (n=3).

Figure 6:
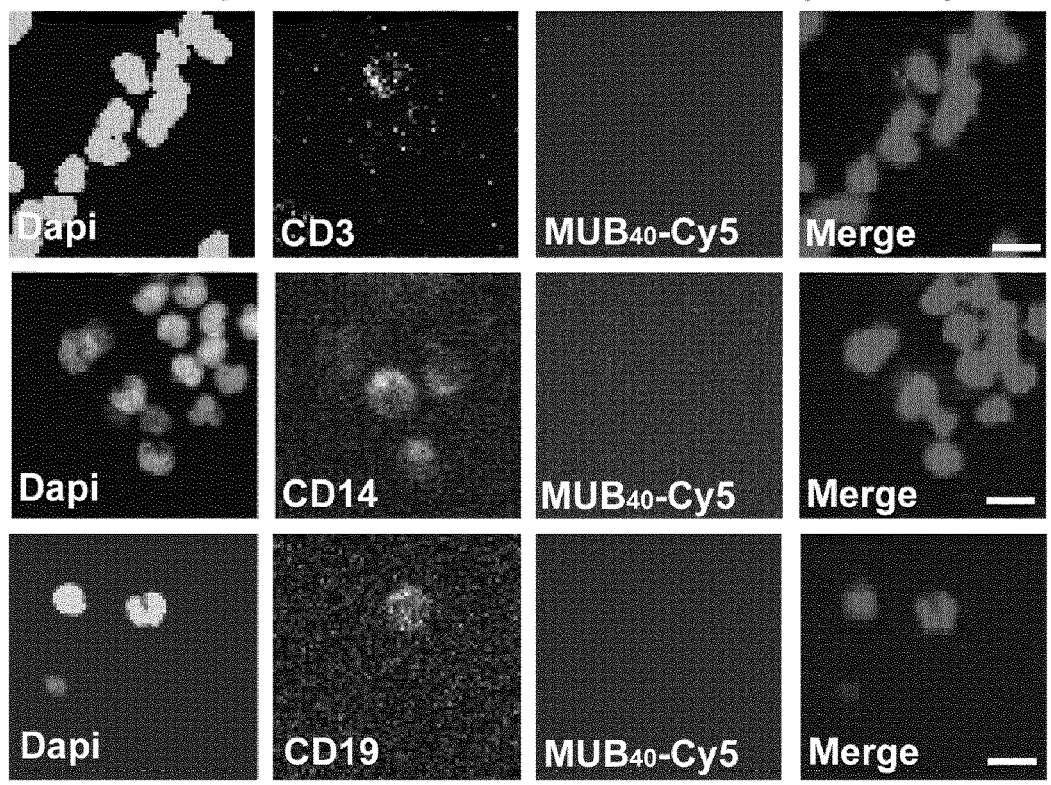

FIG. 6. Peripheral blood mononuclear cells (PBMC) were not labeled by $MUB_{40}$ (SEQ ID NO: 3)-Cy5

PBMC were purified from human blood samples and fixed in PFA 3%. CD3+ (T lymphocyte), CD14+ (monocytes, macrophage), and CD19+ (B lymphocyte) cells (red) were not stained with MUB$_{40}$-Cy5 (magenta), using the same protocol as in FIG. 5a (neutrophils). Bars are 10 µm.

FIG. 7. Detection of infiltrated neutrophils with MUB$_{40}$ (SEQ ID NO: 3)-Cy5 in guinea pig and mouse models of shigellosis.

(A) Guinea pig and mouse neutrophils were fixed and labelled with MUB$_{40}$ (SEQ ID NO: 3)-Cy5 (magenta). Nuclei were stained with Dapi (blue). Bars, 10 µm. (B) Upon Shigella flexneri 5a pGFP (green) infection of the guinea pig colonic mucosa, infiltrated neutrophils were labelled with MUB40 (SEQ ID NO: 3)-Cy5 (magenta) or MUB40 (SEQ ID NO: 3)-Alexa405 (blue). Bars, 100 µm. (C) Upon Shigella sonnei pMW211 (pDsRed) (red) oral challenge of mice, a local colonization of the colonic mucosa was observed, associated with a recruitment of neutrophils labelled with MUB$_{40}$ (SEQ ID NO: 3)-Cy5 (magenta). Actin was stained with Phalloidin-FITC (green), bar, 100 µm.

Figure 8:
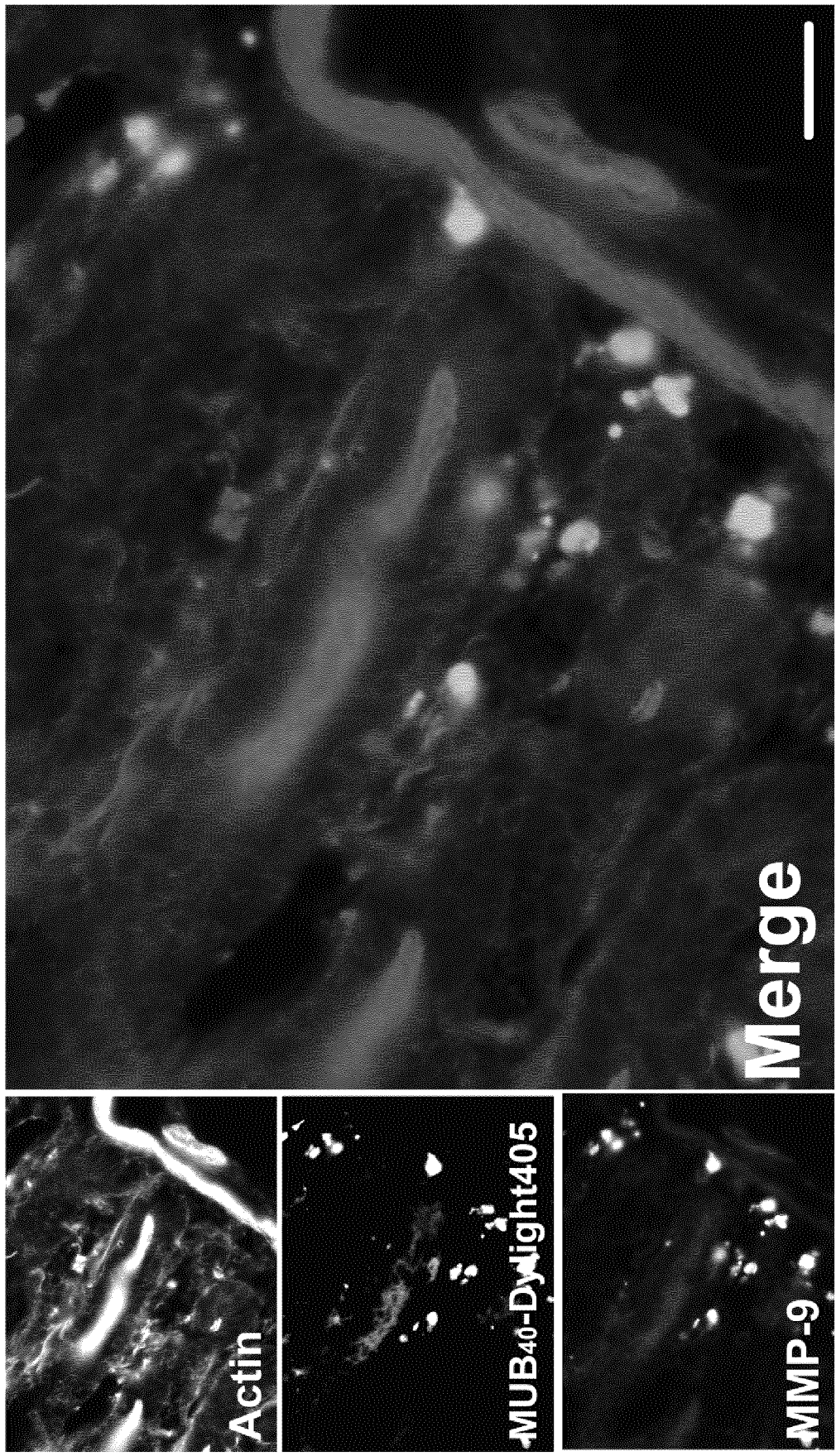

FIG. 8. Infiltrated neutrophil detection in the rabbit intestinal mucosa

Immunofluorescence detection of neutrophils (MMP-9, green) in a rabbit ileum section. Actin was stained with RRX-phalloidin (red), and neutrophils were labeled with MUB$_{40}$ (SEQ ID NO: 3)-Dylight405 (blue) at a final concentration of 1 µg/mL and a anti-gelatinase (MMP-9) antibody (green). Bar is 30 µm.

Figure 9:
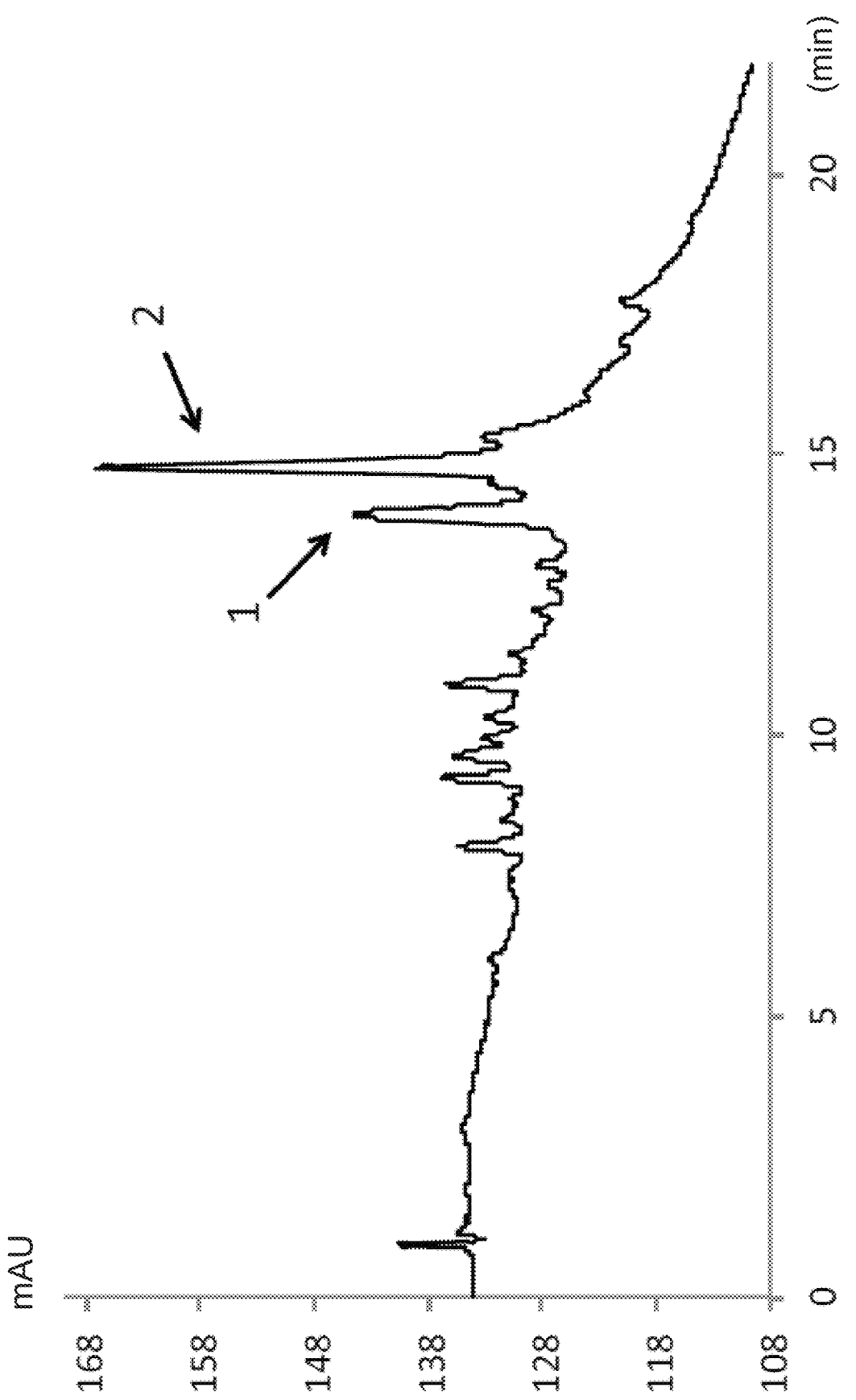

FIG. 9. RP-HPLC chromatogram of crude RI-MUB40.

Figure 10:
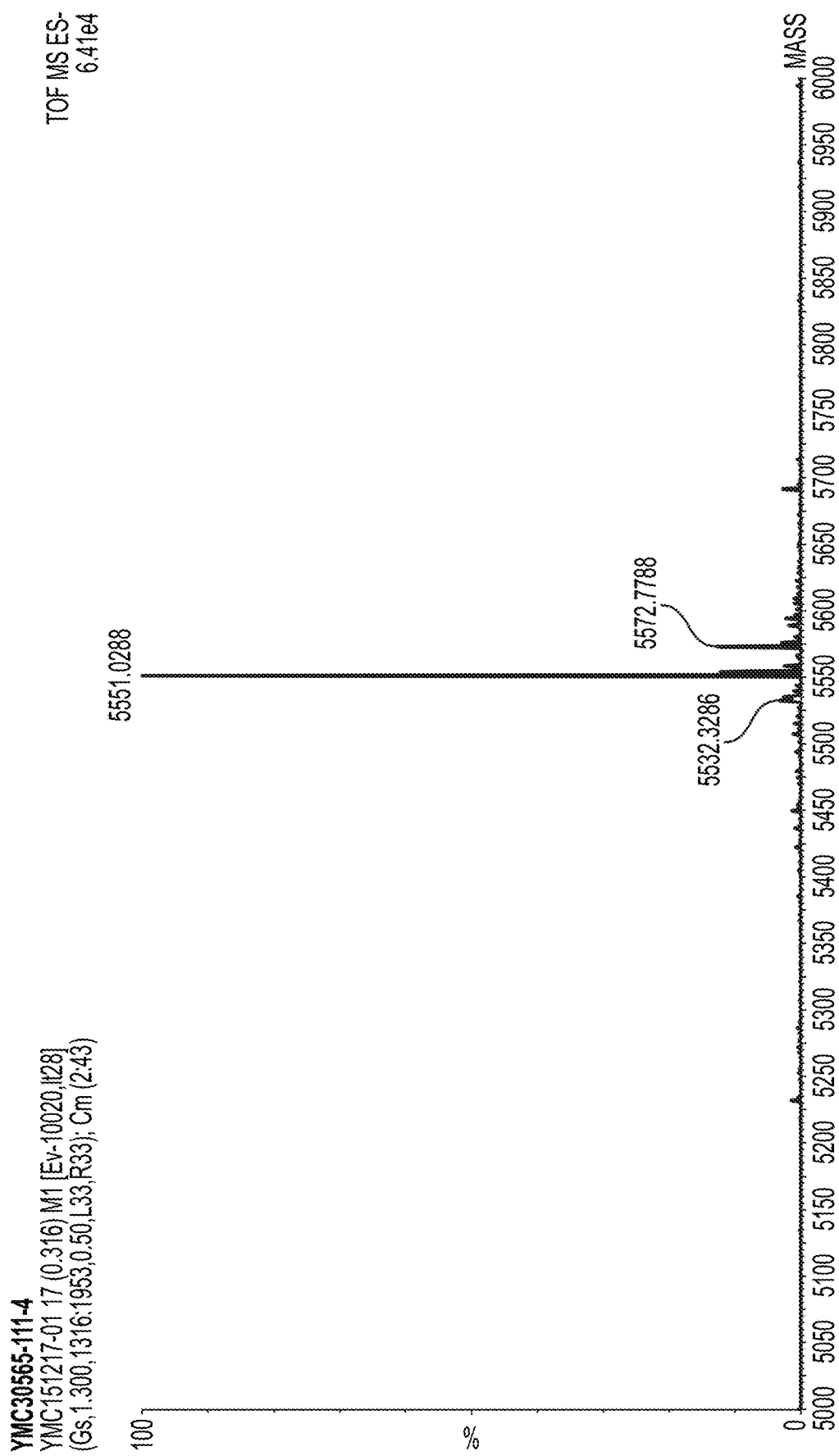

HPLC analysis was performed on a symmetry 300C18 column (Waters) by applying a 15%-40% B gradient in 20 min at a 0.35 mL/min flow rate, where A=ammonium acetate 50 mM pH6.5 and B=CH$_3$CN. Arrow (1): target peptide, Arrow (2): Asp-Gly deletion FIG. 10. Cy5-RI-MUB40 mass The experimental mass of Cy5-RI-MUB40 (SEQ ID NO: 2) was checked by negative electrospray mass spectroscopy on a quadrupole-TOF Micro mass spectrometer (Waters) equipped with a Z-spray API source, giving 5551.265 Da after MaxEnt1 (Masslynx, Waters) deconvolution (expected 5550,115)

Figure 11:
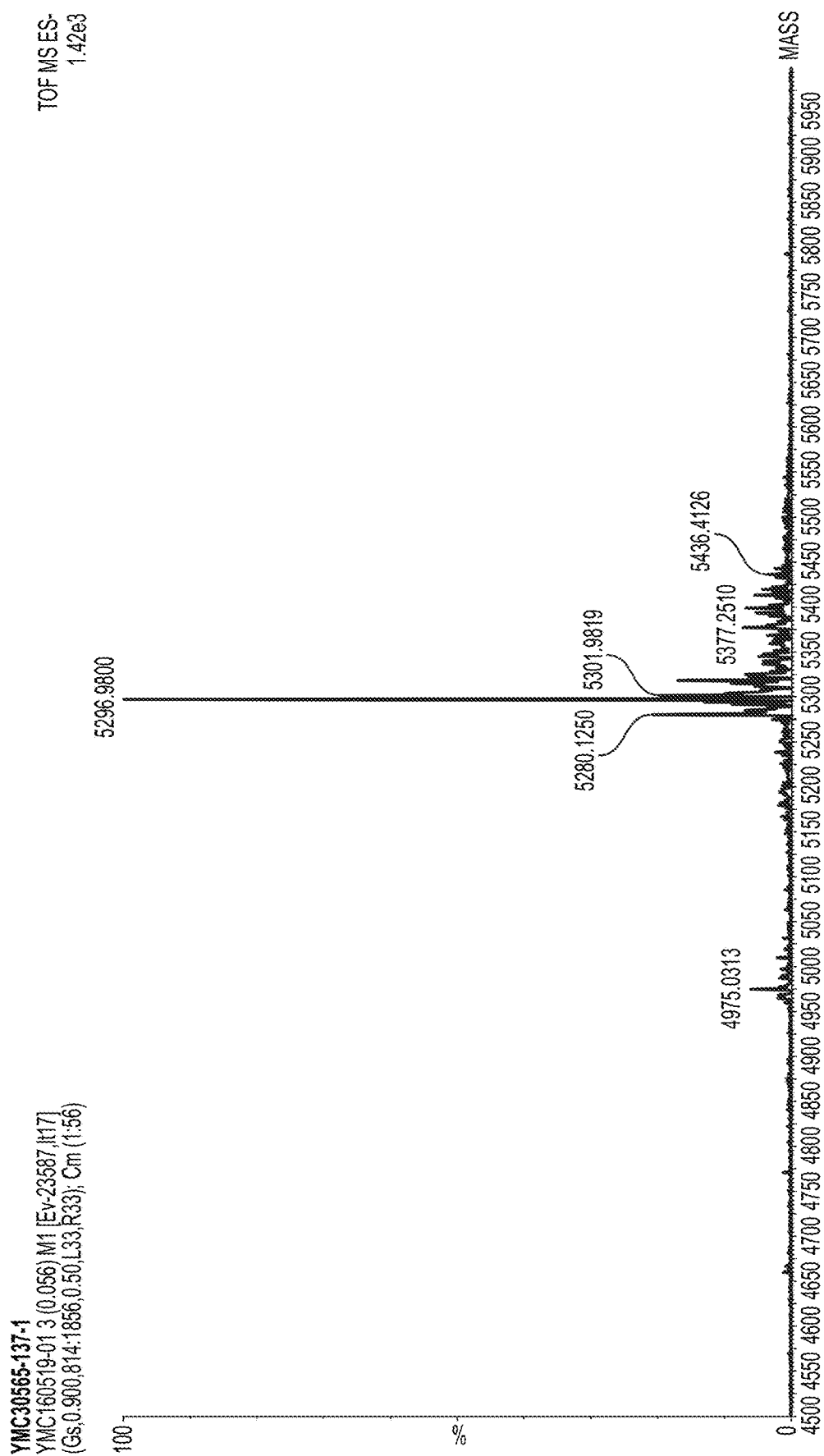

FIG. 11. Biot-RI-MUB40 mass

The experimental mass of Biot-RI-MUB40 was checked by negative electrospray mass spectroscopy on a quadrupole-TOF Micro mass spectrometer (Waters) equipped with a Z-spray API source, giving 5296.994 Da after MaxEnt1 (Masslynx, Waters) deconvolution (expected 5296.792)

Figure 12:
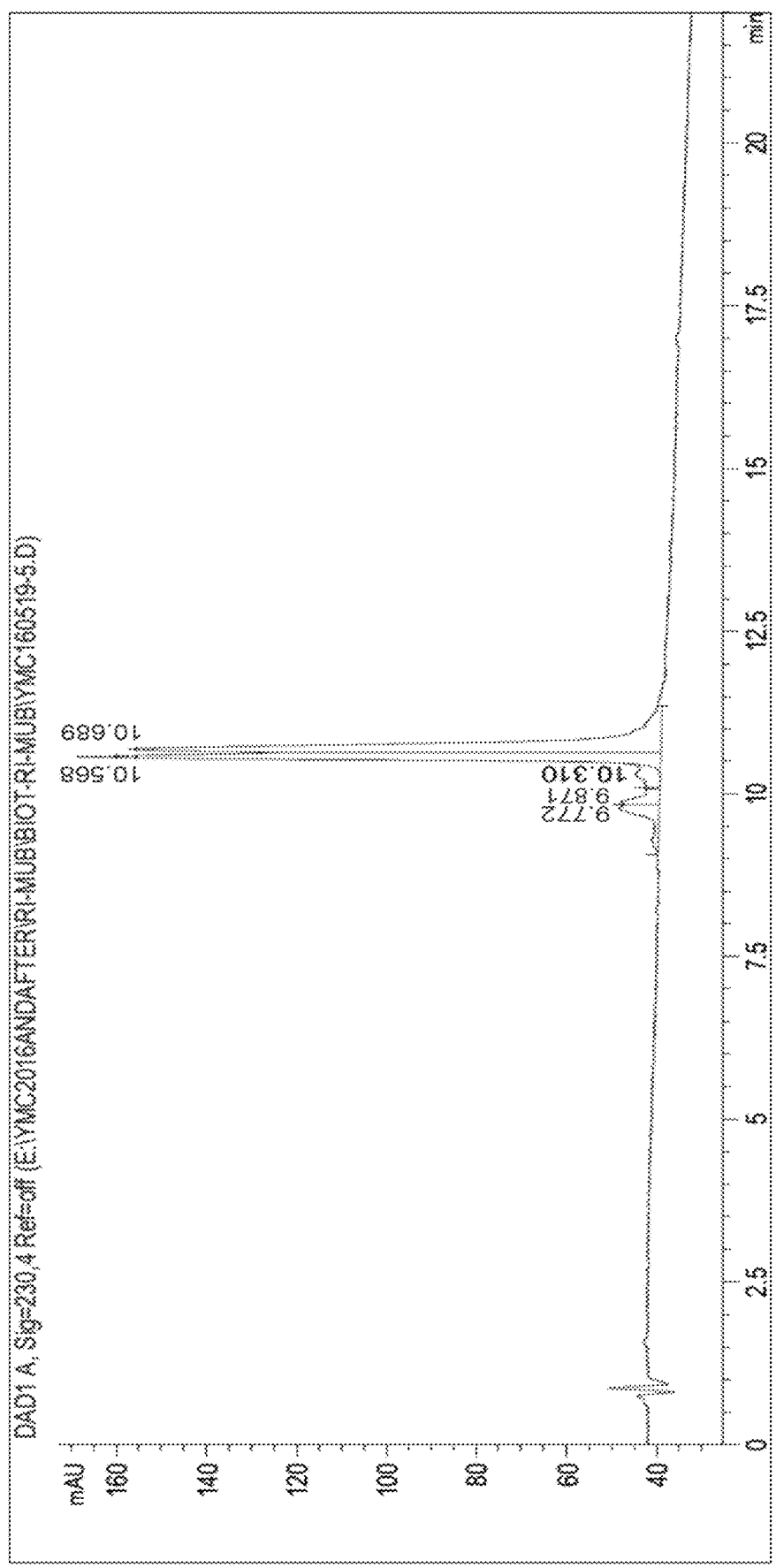

FIG. 12. Biot-RI-MUB40 HPLC

Figure 13:
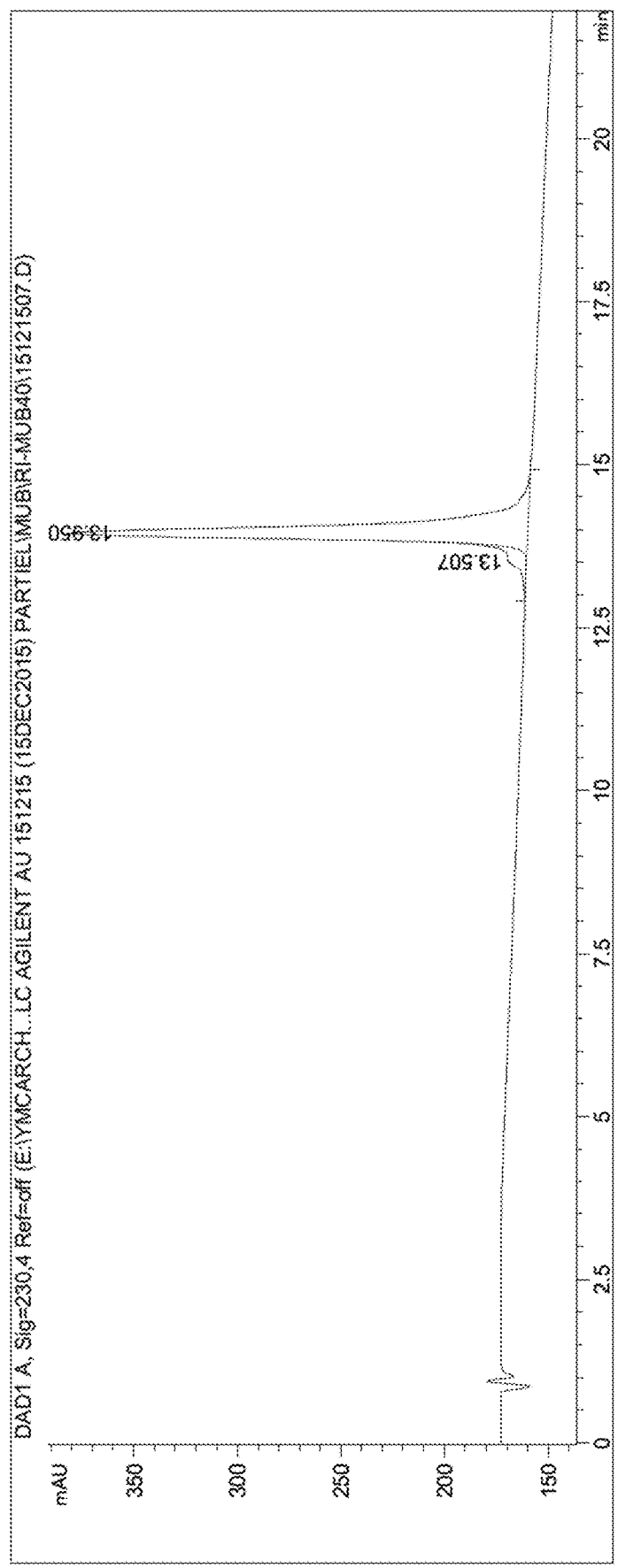

HPLC analysis of purified biot-RI-MUB40 was performed on an Aeris C18 column (Phenomenex) by applying a 25%-50% B gradient in 20 min at a 0.35 mL/min flow rate, where A=0.08% aqueous TFA and B=CH$_3$CN FIG. 13. Cy5-RI-MUB40 HPLC HPLC analysis of purified Cy5-RI-MUB40 (SEQ ID NO: 2) was performed on a symmetry 300C18 column (Waters) by applying a 15%-40% B gradient in 20 min at a 0.35 mL/min flow rate, where A=ammonium acetate 50 mM pH6.5 and B=CH$_3$CN FIG. 14. MUB$_{40}$ (SEQ ID NO: 3) binds specifically to lactoferrin, stored in neutrophil specific (β1) and tertiary granules (32)

(A) Human neutrophil granules were purified and fractionated on a 3-layers Percoll gradient (Kjeldsen et al., 1999). Total granule, α (azurophil granules), β1 (specific granules), β2 (tertiary granules), and γ (secretory vesicles) fractions were separated on a 10% SDS Page gel and stained with Coomassie. Most abundant proteins in each fraction was identified by mass spectrometry (right panel) (raw data presented in FIG. 15). The preferential labelling of the β1 and β2 fractions with RI-MUB$_{40}$ (SEQ ID NO: 2)-Biotin (1 µg/mL) together with a α-lactoferrin antibody was observed by western blot using Streptavidin-HRP (bottom). Legend MS analysis: (1) Lactoferrin, (2) Lactoferrin, (3) Gelastinase (MMP-9) Cathespin G Elastase Myeloblastin, (4,5) NGAL Cathelicidin (LL-37), (6) Lyzozyme C, (7) Protein S100-A9 (B) Granule fractions (α, β1, β2 and γ) were additionally separated on an Ag-Page gel (allowing the identification of high molecular-weight complexes) prior to transferring proteins onto a nitrocellulose membrane. The preferential labelling of the β1 and β2 fractions with RI-MUB$_{40}$ (SEQ ID NO: 2)-Biotin (1 µg/mL) was confirmed by western blot using Streptavidin-HRP. (C) Purified neutrophil granules were incubated with RI-MUB$_{40}$ (SEQ ID NO: 2)-Biotin to identify its target. The most abundant protein present in the output was identified by mass spectrometry as lactoferrin (78 kDa). (D) The labelling of lactoferrin by MUB$_{40}$ was confirmed by immunofluorescence on fixed human neutrophils, showing a α-localization of the fluorescent signals using RI-MUB$_{40}$ (SEQ ID NO: 2)-Cy5 (magenta) and a α-lactoferrin antibody (green). DNA was stained with Dapi, bar, 20 µm. (E) In order to confirm the labelling of human lactoferrin by MUB$_{40}$, commercial purified lactoferrin was allowed to polymerize in RPMI 1640 culture medium (0.35 µg/mL and 3.5 µg/mL) at 37° C. (adapted from (Bennett et al., 1981), (Mantel et al., 1994)). Polymerized lactoferrin was fixed and immunolabeled with MUB$_{40}$ (SEQ ID NO: 3)-Cy5 (magenta) and an α-lactoferrin antibody (green). bar, 20 µm. Deglycosylated lactoferrin (PNGase treatment) was no longer labelled by MUB$_{40}$ (SEQ ID NO: 3)-Cy5. (F) Lactoferrin (naïve and deglycosylated) polymers (5 µg) were separated on an Ag-Page gel prior to transfer onto a nitrocellulose membrane. The interaction between lactoferrin and MUB$_{40}$ was confirmed by western blot with RI-MUB40-Biotin (1 µg/mL) and streptavidin-HRP.

Figure 15:
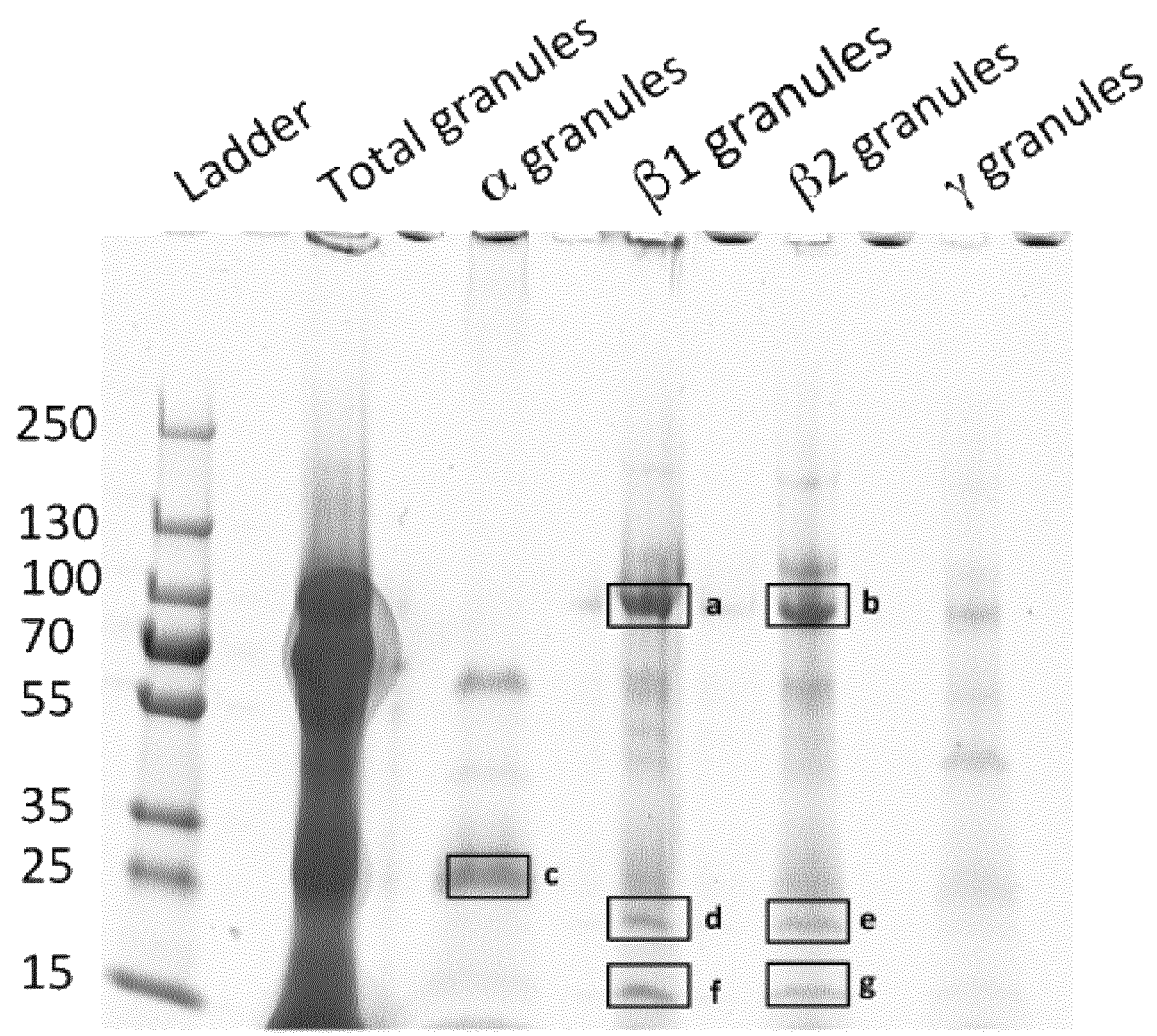

FIG. 15. Neutrophil granule fractionation and protein content separation by electrophoresis Neutrophil granules were purified as described in Methods and fractionated on a three-layer Percoll gradient, as described previously[1]. =10 µg of each sample (α, β1, β2 and γ granule fractions) were separated on a 12% SDS-PAGE gel and stained with InstantBlue Protein Stain (Sigma-Aldrich). Indicated bands (a-g) were cut and further analysed by Mass Spectrometry for protein identification.

FIG. 16. Neutrophil lactoferrin degranulation assessment with RI-MUB$_{40}$-Cy5 in vitro and in vivo in infectious and sterile inflammation models (A) The kinetics of the lactoferrin degranulation (cell surface exposure, white arrows) was assessed by live microscopy on neutrophils infected by Shigella flexneri pGFP (green) (at MOI 20) in the presence of RI-MUB$_{40}$ (SEQ ID NO: 2)-Cy5 (1 µg/mL, magenta) (RPMI 1640 medium supplemented with 10 mM Hepes at 37° C.). Images were acquired every 60 s for 9 min (see Movie S1), bar 10 µm. RI-MUB$_{40}$ (SEQ ID NO: 2)-Cy5 did not cross the plasma membrane of living cells (data not shown), similarly to MUB$_{70}$ (SEQ ID NO: 11) (Coïc et al., 2012). (B) Neutrophil lactoferrin degranulation is detected in Shigella flexneri 5a pGFP (green) foci of infection in the guinea pig mucosa with MUB$_{40}$ (SEQ ID NO: 3)-Cy5 (1 µg/mL, magenta) (white arrow) DNA was stained with Dapi (blue). Bar, 20 µm. (C-D) RI-MUB$_{40}$ (SEQ ID NO: 2)-Cy5 accumulates at sites of inflammation in vivo. C5761/6J mice were injected i.v. with serum from K/B×N mice (K/B×N, n=4) or saline (saline, n=5) (day 0). (C) Photon emission corresponding to luminol degradation by myeloperoxidase activity present in the joints was measured 6 days post arthritis induction (top panels). Bioluminescence in regions of interest (red circles) is expressed as average radiance (p/s/cm$^2$/sr; left scatter plot). Accumulation of RI-MUB$_{40}$-Cy5 fluorescent signal (640 nm/700 nm) in the joints of arthritic mice but not in control mice (middle panels and lower panels as merged picture with CT). Epifluorescence in regions of interest (red circles) is expressed as average radiant efficiency (p/s/cm$^2$/sr/[uW/cm$^2$]; right scatter plot). (D) Correlation of bioluminescent signal and RI-MUB$_{40}$-Cy5 fluorescent signal in indicated regions of interest (hind ankle joints). Data in (C) are representative of two independent experiments. Error bars correspond to the SEM, **** p≤0.0001 (unpaired t-test).

FIG. 17. Inflammatory tissues labelling with MUB$_{40}$-Cy5

Tissue inflammation is characterized by neutrophil recruitment and potentially associated with lactoferrin degranulation. The validation of MUB$_{40}$ peptides (here MUB$_{40}$ (SEQ ID NO: 3)-Cy5) as markers of inflammation was confirmed on human biopsies, here (A) a malignant fibrous hysticocytoma (sterile inflammation) and (B) a streptococcal skin abscess (infectious inflammation). Lactoferrin was stained with an anti-lactoferrin antibody (green) and MUB$_{40}$ (SEQ ID NO: 3)-Cy5 (1 µg/mL, magenta), DNA was stained with Dapi (blue). Bars, 150 µm. Surface plots and correlation of fluorescent signals were obtained with the Fiji software.

Figure 18A:
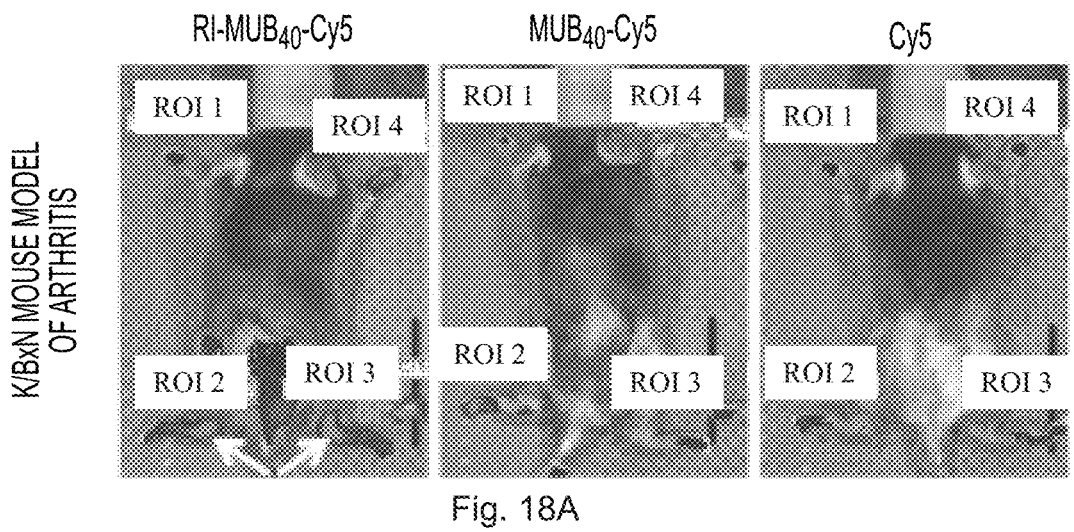
Figure 18B:
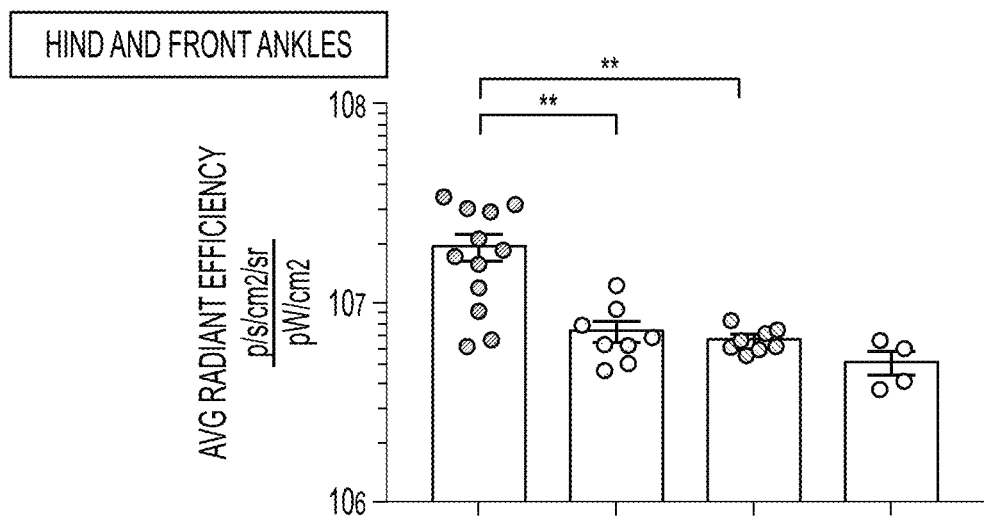
Figure 18B:
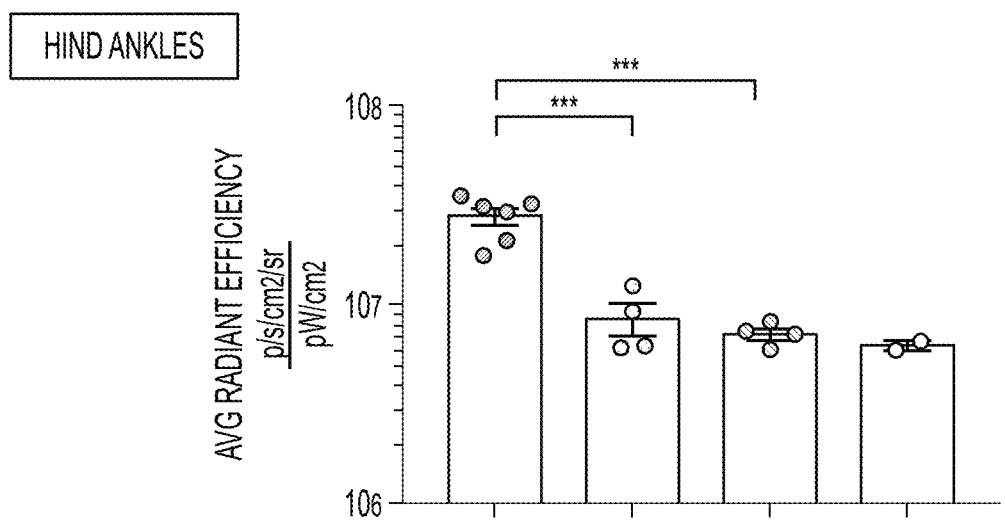

FIG. 18. Improved detection of inflamed tissues in vivo with RI-MUB40-Cy5 compared to MUB40

K/B×N mice were injected intravenously with RI-MUB40-Cy5 (SEQ ID NO: 2), MUB40-Cy5 (SEQ ID NO: 3) or Cy5 only. The inventors demonstrated that 2 days post-injection, the fluorescent signal associated with RI-MUB40-Cy5 (SEQ ID NO: 2) accumulation at hind and front inflamed ankles was significantly higher compared to MUB40-Cy5 (SEQ ID NO: 3) (p<0.01) or Cy5 only (p<0.001). This result confirms the increased stability of RI-MUB40-Cy5 (SEQ ID NO: 2) compared to MUB40-Cy5 (SEQ ID NO: 3) in vivo.

(A) Ankles of K×B/N mice were imaged 2 Days after intravenous injection of 0.9 nmoles of RI-MUB40-Cy5 (SEQ ID NO: 2), MUB40-Cy5 (SEQ ID NO: 3) or Cy5 only. Fluorescence was quantified at the level of front or hind ankles (in ROI, as indicated).

(B) Quantification of the fluorescent signal associated with RI-MUB40 (SEQ ID NO: 2)-Cy5, MUB40 (SEQ ID NO: 3)-Cy5 or Cy5 accumulation at hind and front ankles (top) or hind ankles only (bottom). Results are average from at least three animals.  indicates p<0.01 and * indicates p<0.001 (Student's T-test).

EXAMPLES

A. MATERIALS AND METHODS

MUB$_{40}$ Peptides Series Synthesis

The synthesis were carried out on a 100 µmoles scale on an ABI 433 synthesizer (Applied Biosystems, Foster City, Calif.) from a polystyrene AM-RAM resin and using conventional FMOC chemistry. N-terminal acetylation was achieved by treating the peptide resins at the end of the synthesis with acetic anhydride for 30 minutes. As a result, all peptides were N-terminal amide and C-terminal acetylated. For the purpose of structural analysis (CD and gel filtration), MUB$_{40}$ peptides were submitted to a N-ethyl maleimide treatment in order to prevent covalent dimer formation. Fluorophore labeling and biotin derivatization were performed through the conjugation of their maleimide derivatives to the free sulfhydryle peptides. All purification steps and HPLC analysis were done by C18 Reverse Phase columns. Final characterization by electro-spray mass analysis were consistent with the expected masses (between brackets): Cy5-labeled MUB$_{40}$#1 (SEQ ID NO: 3): 5549.740 (5550.115); Cy5-labeled MUB$_{40}$#2 (SEQ ID NO: 4): 5447.472 (5447.933); Cy5-labeled MUB$_{40}$#3 (SEQ ID NO: 5): 5588.273 (5589.170); Cy5-labeled MUB$_{40}$#4 (SEQ ID NO: 6): 5501.778 (5502.093); Cy5-labeled RI-MUB$_{40}$#1 (SEQ ID NO: 2) (RI-MUB40): 5551.265 (5550.115); Dylight 405-labeled MUB$_{40}$#1 (SEQ ID NO: 3) (MUB$_{40}$-D405): 5519,849 (5518, 9 . . . —restricted proprietary information); RI-MUB$_{40}$#1 (SEQ ID NO: 3)-Biotin (RI-MUB$_{40}$-Biotin): 5296.994 (5296.792). Detailed synthesis and derivatization steps and the biophysical analysis of MUB$_{40}$ peptides are described below.

Synthesis and cleavage. The synthesis were carried out on a 100 µmoles scale on an ABI 433 synthesizer (Applied Biosystems, Foster City, Calif.) equipped with a conductivity flow cell to monitor Fmoc deprotection from a polystyrene AM-RAM resin (capacity 0.41 mmol/g for MUB$_{40}$ peptides and 0.62 mmol/g for retro-inverso RI-MUB$_{40}$#1, Rapp Polymere GmbH, Tuebingen, Germany). Standard Fmoc amino acids, Dmb, and pseudoproline dipeptides were activated with HCTU (2-(6-Chloro-1H-benzotriazole-1-yl)-1,1,3,3-tetramethylaminium hexafluorophosphate) DIPEA (N,N-diisopropylethylamine). Fmoc-D-amino acids and Hmb dipeptide were activated with HATU (1-[bis(dimethylamino)methylene]-1H-1,2,3-triazolo-[4,5-13]pyridinium hexafluorophosphate 3-oxide)/DIPEA). All Fmoc-AAs and surrogates were single-coupled with eight-fold molar excess regarding the resin. Both coupling reagents, N-methyl pyrrolidone (NMP) and standard Fmoc amino acids were obtained from Applied Biosystems. Fmoc D-amino acids were obtained from Eurogentec (Eurogentec, Seraing, Belgium). Fmoc L and D-amino acids were side-protected as follows: tBu for aspartic acid, glutamic acid, serine, threonine, and tyrosine; Trt for cysteine and histidine: Boc for lysine; and Pbf (2,2,4,6,7-pentamethyl-dihydrobenzofuran-5-sulfonyl) for arginine. Fmoc-Asp(OtBu)-(Dmb)Gly-OH dipeptides and pseudoproline (oxazolidine) dipeptides were purchased from Merck-Novabiochem. Fmoc-D-Asp(OtBu)-(Hmb)Gly-OH was purchased from Bachem (Bubendorf, Switzerland). Piperidine was purchased from Sigma-Aldrich (St Louis, Mo., USA).

N-terminal acetylation was achieved by treating the peptide resin at the end of the synthesis with acetic anhydride for 30 minutes. As a result, all peptides were N-terminal amide and C-terminal acetylated. Cleavage from the solid support and deprotection of the amino acid side chains were accomplished in one step by 3 h treatment at room temperature with a mixture of TFA/ethanedithiol/triisopropylsilane/water (92.5/2.5/2.5/2.5) for MUB$_{40}$ peptides or TFA/ethanedithiol/triisopropylsilane/water/phenol (92/2.5/2/2.5/1) for 4 h for RI-MUB$_{40}$. After filtration of the resin, the cleavage mixtures were poured into ice-cold diethyl ether. The precipitates were recovered by centrifugation, washed three times with cold diethyl ether, dried, resuspended in a mixture of water and acetonitrile, and freeze dried.

HPLC analysis of synthesized peptides. Analysis of crude mixtures and purity control of the final peptides were performed by RP-HPLC on an Agilent (Santa Clara, Calif., USA) 1100 Series liquid chromatograph and monitored with a photodiode array detector by absorbance at 230 nm, according to the following methods. A linear gradient from 15% to 40% of acetonitrile in aqueous solvent A (50 mM ammonium acetate, pH 6.5) over 20 min was applied at a 0.35 ml/min flow rate on a Symmetry 300 C18 3.5 µm 2.1×100 mm column (Waters, Manchester, UK). To check the purity of RI-MUB$_{40}$ derivatives, supplementary analyses were done in 0.08% aqueous TFA by applying a 25%-50% acetonitrile gradient on an *Aeris* Peptide 3.6µ XB-C18 column.

Peptides purification. The free sulfhydryl crude peptides MUB$_{40}$#1, #2, & #3 (SEQ ID NOS: 3-5) were solubilized at a final concentration of 20 mg/ml in a mixture of solvent A and acetonitrile, 8:2 v/v. Crude MUB$_{40}$#4 was solubilized at the same concentration in water with aqueous ammonia (pH8) and 10 equivalent of DTT (1,4-Dithio-DL-threitol). Crude RI-MUB$_{40}$ was solubilized at a final concentration of 3.5 mg/ml in solvent A. Those materials were purified by RP-MPLC (AP-100/200 flash, Armen Instrument, Saint Ave, France) on a preparative column (26×313 mm) packed with 100 Å 20 µm C18 Nucleoprep packing (Macherey & Nagel GmbH & Co, Düren, Germany), by applying a linear gradient of 15-70% (MUB$_{40}$ peptides) or 15-50% (RI-MUB$_{40}$) solvent B (mixture of acetonitrile and solvent A, 8/2 v/v) in solvent A over 60 min at a 20 ml/min flow rate. The purification was monitored at 214 nm (UV detector K2501, Knauer, Berlin, Germany). The suitable fractions were pooled and freeze dried. The overall isolated yields (from 20% to 30%) were in concordance with the observed synthesis yields deducted from the crude's HPLC analysis.

MUB$_{40}$ peptides conjugation. Cy5 and Dylight 405 (Thermofisher Scientific) conjugations were operated in a 0.1 M Phosphate buffer pH=6 (MUB$_{40}$ peptides) or pH=7.2 (RI-MUB$_{40}$), using 1.2 equivalent of the correspondent maleimide derivative (InvitroGen) in the presence of 1.5 equivalent of TCEP (Tris (2-carboxyethyl)phosphine) per mole of cysteine residue. Repeating one time, this 30 minute coupling protocol was necessary to achieve completion of RI-MUB$_{40}$ labeling. The labeled peptides were purified by RP-HPLC using a linear gradient of 15-40% acetonitrile over 20 min at a 6 ml/min flow rate, either on a Nucleosil 5 µm C18 300 Å semi-preparative column equilibrated in solvent A (MUB$_{40}$ peptides) or on a Kromasil 5 µm C18 300 Å semi-preparative column (AIT, Houilles) equilibrated in 50 mM Triethyl ammonium acetate (RI-MUB$_{40}$). The purity was checked according to the formerly-described HPLC analytical method. The exact concentration was determined by quantitative amino acid analysis (Hitachi, L-8800 analyzer), giving a 50% to 60% conjugation yield.

Biotinylated RI-MUB$_{40}$ was obtained by adding the free sulfhydrile peptide to 5 equivalents of the maleimide derivative (EZ-linked maleimide-PEG2-biotin, Thermoscience) in 0.1M phosphate buffer (pH6). The biotinylated peptide was purified by HPLC in 50 mM ammonium acetate on a Kromasil 5 µm C18 300 Å semi-preparative column, using a linear gradient of 15-40% acetonitrile over 20 min at a 6 ml/min flow rate. A double peak was observed in the analytical HPLC profile, which was attributed to the resolution of the two isomers resulting from the addition of the sulfhydryl peptide on the maleimide double bond.

Electrospray ionisation mass spectrometry. Mass spectrometry was carried out on a quadrupole-TOF Micro mass spectrometer (Waters) equipped with a Z-spray API source. Capillary, sample cone, and extraction cone voltages were set at 3 kV, 40V, and 10V, respectively. Source and desolvation temperatures were set at 80 and 250° C., respectively. Data were acquired by scanning over the m/z range 150-2000 at a scan rate of 1 s and an interscan delay of 0.1 s. Peptides were dissolved in a mixture of water/methanol/ acetic acid (49.5/49.5/1, v/v/v) at a concentration of 1 µg/µl and analyzed in positive-ion mode by infusion at a flaw rate of 5 µl/min. Around fifty spectra were combined and the resultant raw multi-charged spectra were processed using the MaxEnt1 deconvolution algorithm embedded in the Masslynx software. Given the deconvolution process of MaxEnt1, applied to the charged molecules (the Cy5 moiety is positively charged), final characterization was consistent with the expected masses (between brackets): Cy5-labeled MUB$_{40}$#1 (SEQ ID NO: 3): 5549.740 (5550.115); Cy5-labeled MUB$_{40}$#2 (SEQ ID NO: 4): 5447.472 (5447.933); Cy5-labeled MUB$_{40}$#3 (SEQ ID NO: 5): 5588.273 (5589.170); Cy5-labeled MUB$_{40}$#4 (SEQ ID NO: 6): 5501.778 (5502.093); Cy5-labeled RI-MUB$_{40}$#1 (SEQ ID NO: 3) (RI-MUB$_{40}$): 5551.265 (5550.115); Dylight 405-labeled MUB$_{40}$#1 (SEQ ID NO: 3) (MUB$_{40}$-D405): 5519, 849 (5518.9.); RI-MUB$_{40}$#1 (SEQ ID NO: 3)-Biotin (RI-MUB$_{40}$-Biotin): 5296.994 (5296.792).

Neutrophil Granules Purification and Fractionation.

Neutrophil granules were collected from purified polymorphonuclear neutrophils, following the procedure described previously (Kjeldsen et al., 1999). Neutrophils were resuspended in PBS (2.7. 10$^6$ cell/mL) with 0.5 µL/mL DFP (Sigma-Aldrich) and incubated on ice for 15 min prior centrifugation (1300 rpm; 10 min). Cells were resuspended (20.10$^6$ cell/mL) in a relaxation buffer (KCl 100 mM, NaCl 3 mM, MgCl$_2$ 3.5 mM, PIPES 10 mM, adjusted at pH 6.8) with a cocktail of protease inhibitors (400 mM leupeptin, 400 mM pepstatin, 3 mM PMSF, 1 mM orthovanadate) and supplemented with 1 mM ATP, 1 mM EDTA, and 1.25 mM EGTA. Cells were lysed by nitrogen cavitation (350 psi, 20 min). Cell lysates were centrifuged at 3000 rpm for 15 min to remove remaining cells and nuclei. For total granule recovery, lysates were centrifuged at 16000 rpm for 45 min; granules were resuspended in protease inhibitor-containing relaxation buffer (described above) and stored at −80° C. For granule fractionation, lysates were centrifuged onto a 3-layers Percoll gradient (densities 1.120 g/mL-1.090 g/mL-1.050 g/mL) at 37.000×g for 30 min at 4° C., as described in (Kjeldsen et al. 1999). From the top to the bottom, γ (secretory vesicles), β2 (tertiary granules), β1 (specific granules), and α (azurophil granules) fractions were collected. Remaining Percoll solution was removed by ultracentrifugation (100.000×g for 90 min at 4° C.); purified granules were collected in inhibitor-containing relaxation buffer and stored at −80° C.

Human and Mouse Models of Inflammation

Colon explant surgical collection. In summary, human colon segments (ascending, descending, and sigmoid colon) were obtained from fully informed patients undergoing surgery for colon carcinoma and were analyzed anonymously. Patient written consent was obtained, according to the French bioethics law. None of the patients had undergone radiotherapy or chemotherapy. According to the pathologist's examination rules for the longitudinally bisected colon, a healthy segment of tissue, which was distant from the tumor region and devoid of metastatic cells, was removed. Tissues were processed according to the French Government guidelines for research on human tissues and the French Bioethics Act with the authorization no RBM 2009-50.

Human inflammatory tissues. Human biopsies from patients diagnosed for malignant fibrous histiocytoma and for a streptococcal skin abscess were collected and processed at the Kremlin Bicêtre Hospital, Anatomy and Pathological Histology Department. Tissue samples were fixed in formaldehyde and further embedded in paraffin. 10 µm sections were obtained using a microtome (Leica Biosystem). Tissues were labeled with a mouse anti-lactoferrin primary monoclonal antibody (Hycult biotech, clone 265-

1K1, 1:50 dilution), MUB40-Cy5 (SEQ ID NO: 3) (1 µg/mL), and Dapi (1:1000 dilution) as described below.

Ex vivo infection of human colonic tissue. Human colon explants were infected with *S. flexneri* 5a (M90T) pGFP, as described in (Nothelfer et al. 2014) and adapted from (Coron et al. 2009). Briefly, colonic tissues were cut into ~5 cm² segments and pinned flat, with the submucosa facing down, onto a 4% agarose layer in tissue culture Petri dishes containing DMEM/F12 culture medium (Invitrogen) supplemented with 10% FBS, glutamine, and 2.1 g/L NaHCO₃ (Sigma-Aldrich). *S. flexneri* (M90T) 5a pGFP was added at ~2×10⁸ bacteria per cm² of tissue. Bacteria were allowed to settle for 15 min at room temperature before incubation at 37° C., 5% $CO_2$ for 6 h on a slowly rocking tray. Tissue was fixed by overnight incubation with 4% PFA (Euromedex) and 0.1 M Hepes (Gibco) in PBS. For whole-mount staining, tissues were fixed on a 40×11-mm tissue culture dish (TPP) with Histoacryl tissue glue (Braun). To obtain 150-µm-thick sections, the tissue was embedded in low-melting agarose according to (Snippert et al. 2011) and cut with a vibratome (VT1000E; Leica).

Mouse arthritis model. 6-7 weeks old female C57BL/6J mice were purchased from Charles River France, housed under specific pathogen-free (SPF) conditions and handled in accordance with French and European directives. Mouse protocols were approved by the Animal Ethics committee CETEA number 89 (Institut Pasteur, Paris, France) and registered under #2013-0103, and by the French Ministry of Research under agreement #00513.02. Arthritis was induced by i.v. injection of 120 µL K/B×N serum and arthritis scored as described previously (Bruhns et al. 2003). Mice injected with physiological saline were used as controls. On day 6 after serum transfer, mice were anesthetized, shaved, depilated and injected i.p. with luminol (10 mg/mouse) and i.v. with 5 µg/mouse MUB-40 Cy5. Epifluorescence, bioluminescence and CT images were acquired 10-90 min after injection using an IVIS SpectrumCT (Perkin Elmer).

Flow Cytometry

Human. Neutrophils and PBMCs were separated as described below. Naïve cells were resuspended in PBS+ EDTA 2 mM. Fixed and permealized were were obtained by incubation in PFA 3.2% for 30 min and resuspention in PBS+Triton 0.1% for 30 min. Naïve and fixed/permeabilized cells were incubated with CD45-FITC and $MUB_{40}$-Alexa405 peptide (1 µL/mL) for 15 min at room temperature. Cells were analyzed with a FACSCANTO II (BD) and data were analyzed using Flowjo software.

Mouse. Blood leucocytes were purified by dextran, washed in PBS EDTA and kept on ice. For hematopoietic populations staining, 2 to 3 million cells were resuspended in PBS EDTA, blocked with 16/32 for 15 minutes and stained with antibodies for 30 minutes at 4° C. (CD45 PE-CF594, CD3e FITC, B220 PE-CY7, NKP46 FITC, CD11b PE from BD biosciences, and Ly6G APC-H7, Ly6C APC from Biolegend). Cells were washed with PBS EDTA and fixed in PFA 3.3% at room temperature during 15 minutes. Cells were washed and resuspended in PBS-0.1% Triton for 5 minutes. Cells were then incubated with MUB40-Alexa405 peptide (1 µL/mL) for 15 minutes at RT and washed. Not fixed cells incubated with peptide or fixed cells not incubated with peptide were used as negative control. Cell fluorescence was determined using a Fortessa (BD biosciences) and analyzed with Kaluza Software (Beckman Coulter). The fluorescence intensity was quantified.

Fluorescent Markers and Cell Labeling

Fixation and staining procedures. For microscopy studies, purified or cultured cells and polymerized lactoferrin were resuspended onto 24-well plates containing 12 mm coverslips in RMPI 1640+10 mM Hepes (when cultured in the autologous plasma) and centrifuged at 300×g for 10 min. Culture media were removed and cells were fixed in 4% Paraformaldehyde (PFA) for two hours. Fixed cells were washed three times in PBS+0.1% saponin (Sigma-Aldrich), prior immunolabeling with primary antibodies in the same buffer for 1 hour (Triton 0.1% can alternatively be used for cell permeabilization). After three additional washes in PBS+0.1% saponin, secondary antibodies and fluorescent markers were incubated for one hour. Coverslips were washed three time in PBS+0.1% saponin, three times in PBS, and three times in deionized $H_2O$ and mounted with prolong gold$^{tm}$ mounting media.

Antibodies, fluorescent markers. For immunofluorescence assay, lactoferrin was detected with a mouse anti-lactoferrin primary monoclonal antibody (Hycult biotech, clone 265-1K1, 1:50 dilution) and an anti-mouse-FITC conjugated secondary antibody (1:1000). Nuclei were detected with DAPI (Life Technologies), Lyophilized $MUB_{40}$ peptides ($MUB_{40}$#1 (SEQ ID NO: 3)-Cy5, $MUB_{40}$#2 (SEQ ID NO: 4)-Cy5, $MUB_{40}$#3 (SEQ ID NO: 5)-Cy5, $MUB_{40}$#4 (SEQ ID NO: 6)-Cy5, $MUB_{40}$#1 (SEQ ID NO: 3)-Dylight, RI-$MUB_{40}$ (SEQ ID NO: 2)-Cy5, and RI-$MUB_{40}$ (SEQ ID NO: 2)-Biotin) were solubilized in a phosphate buffer pH8 at a 1 mg/mL concentration and used at a 1:1000 dilution. For PBMC staining CD19-APC (B lymphocytes), CD3-APC (T lymphocytes), and CD14-PercP (monocytes, macrophages) (BD Bioscience) were used at a 1:1000 dilution together with Dapi (1:1000) and $MUB_{40}$-Cy5 (1 mg/mL). Actin was stained with Phalloidin-Rhodamine red X (RRX) (Jackson Immunoresearch Antibodies) used at a 1:1000 final dilution.

Biochemistry

Electrophororesis. Proteins were separated by either SDS Page (4-12% gradient, at 150 volts for 90 min) or Ag-Page (0.7% (w/v) agarose gels in 1×TAE (40 mM Tris-acetate, 1 mM EDTA pH 8), containing 0.1% (w/v) SDS at 65 volts for 3 hours).

Transfer. Protein samples separated by SDS Page were transferred to nitrocellulose membrane performing electrophoretic protein transfer. Protein samples separated by Ag-Page were transferred to nitrocellulose membrane using a vacuum blotter (GE HealthCare); 40 mbar pressure in 4×SSC (0.6 M sodium chloride, 60 mM tri-sodium citrate).

RI-$MUB_{40}$-Biotin immunoblotting. Transferred nitrocellulose membranes were blotted in PBS with RI-$MUB_{40}$-Biotin (SEQ ID NO: 2) (1 µg/mL) for 3 hours, washed three times (15 min) in PBS, incubated with HRP-conjugated Streptavidin (Thermo Scientific ref. N100, 1:1000 dilution) for one hour, and washed three times (15 min) in PBS. RI-$MUB_{40}$ (SEQ ID NO: 2)-Biotin binding was detected with chemiluminescence (ECL kit, GE Healthcare) using a an imaging system (B:Box, Syngene).

RI-$MUB_{40}$-Biotin Pulldown assay. Lyophilized, biotinylated retro-inverso $MUB_{40}$ (RI-$MUB_{40}$-Biotin) was solubilized in 1 mL (185 µg/ml final concentration) of binding buffer (20 mM $NaH_2PO_4$, 0.15 M NaCl, pH 7.5). 150 µL (277 ng) of solubilized RI-MUB40-Biotin was loaded onto 200 µL of washed/packed Streptavidin Sepharose High Performance beads (GE HealthCare). The loaded beads were incubated with gentle rocking for 1 hour at room temperature with 1 mg of purified neutrophil granule fractions. Pulldown fractions were transferred to columns and washed with 10 mL fresh binding buffer. Bound RI-$MUB_{40}$-Biotin and α-purified proteins were eluted with 500 µL 8M Guanidine-HCl, pH 1.5. Eluted proteins were mixed 1:1 with 2× Laemmli buffer (4% SDS, 20% Glycerol, 10% 2-mercaptoethanol, 0.004% bromophenol blue, and 0.125 M Tris HCl, pH 6.8). Samples were run on 4-20% SDS-Page gels and stained with InstantBlue™ (Expedeon, ref. ISB1L) for 1 hour before destaining in deionized $H_2O$. Stained gels were imaged and =80 kDa α-purified band was cut out and sent for mass spectrometry identification.

Lactoferrin polymerization. Human purified lactoferrin (ref: L1294, Sigma-Aldrich) was resuspended in deionized $H_2O$ (35 μg/mL). Lactoferrin was incubated in RPMI+10 mM Hepes supplemented with 10 mM $FeCl_3$, at indicated concentrations (0.35 or 3.5 μg/mL) onto 24-well plates containing 12 mm coverslips overnight at 37° C., adapted from similar lactoferrin polymerization experiments performed in iron saturated phosphate buffer (Mantel et al. 1994).

Lactoferrin deglycolysation. About 10 μg of human purified lactoferrin (ref: L1294, Sigma-Aldrich) was treated by Peptide-N-Glycosidase F (PNGaseF, New England Biolabs, Ipswich Mass., USA) for N-deglycosylation. Protein was treated exactly as described in manufacturer protocol. Twelve unit of PNGase F were added for 4 h at 37° C. for the removal of N-glycosylation.

Lactoferrin polymers interaction with $MUB_{40}$-Cy5. Lactoferrin polymers were centrifuged at 2000 rpm for 10 min and fixed in Paraformaldehyde (PFA) 4% for one hour. Lactoferrin polymers were immunolabeled in PBS+0.1% saponin (Sigma-Aldrich) with a mouse anti-lactoferrin primary monoclonal antibody (Hycult biotech, clone 265-1K1, 1:50 dilution) and an anti-mouse-FITC conjugated secondary antibody (1:1000), together with $MUB_{40}$-Cy5 (SEQ ID NO: 3) (1 μg/mL). Slides were washed three times in PBS and three times in deionized $H_2O$ and mounted with prolong gold$^{tm}$ mounting media.

Lactoferrin polymers interaction with RI-$MUB_{40}$-Biotin. 5 μg lactoferrin polymers pre-formed in RPMI 1640+10 mM Hepes (see above) were separated by Ag-Page, transferred to nitrocellulose membrane and blotted with RI-$MUB_{40}$ (SEQ ID NO: 2)-Biotin (1 μg/mL) in PBS, as described above.

$MUB_{40}$ Peptides Biochemical and Biophysical Characterization

Size Exclusion Chromatography. Gel filtration was performed using an Agilent 1100 system (Agilent Technologies; Palo Alto, Calif., USA) and monitored by absorbance at 280 nm. $MUB_{40}$ peptides were solubilized in the gel filtration buffer (20 mM phosphate buffer, 150 mM NaCl, pH7.4) at a concentration of 10 μg/ml, 100 μg/ml, or 1 mg/ml), separately injected on a Yarra™ 3μ SEC-2000 300×7.8 mm column (Phenomenex, Le Pecq, France), and eluted at a 0.5 ml/min flow rate. The column was calibrated with a mixture of standards proteins (ribonuclease A, 13.7 kDa; carbonic anhydrase 29 kDa; ovalbumin 44 kDa; GE Healthcare) complemented with a custom synthetic peptide of our own library (peptide x, 5.1 kDa; Institut Pasteur). The logarithm of the molecular weights were plotted versus the corresponding partition coefficients (Kay=(Ve−Vo)/(Vc−Vo); Ve, elution volume; Vo, void volume; Vc, geometric column volume), giving log(Mr)=2,3108−2,2361Kav as a calibration curve equation.

Circular dichroism. Far-UV Circular Dichroism (CD) spectra were recorded on an Aviv215 spectropolarimeter (Aviv Biomedical) between 190 and 260 nm using a cylindrical cell with a 0.02 cm path length and an averaging time of 1 s per step. Prior analysis, $MUB_{40}$ peptides were solubilized at a 60 μM final concentration in 20 mM sodium phosphate buffer (pH 7.4) in the presence of 50 mM NaCl. Scans were repeated consecutively three times and merged to produce an averaged spectrum. Results were corrected using buffer baselines measured under the same conditions and normalized to the molar peptide bond concentration and path length as mean molar differential coefficient per residue. MUB40 Peptides were solubilized at a 60 μM final concentration in 20 mM sodium phosphate buffer (pH 7.4) in the presence of 50 mM NaCl.

Trypsin proteolysis. $MUB_{40}$ (SEQ ID NO: 3)-Cy5 and RI-$MUB_{40}$ (SEQ ID NO: 2)-Cy5 were dissolved in 50 mM ammonium bicarbonate, pH 8. Prior to digestion and owing to the propensity of maleimide derivatives to undergo ring-opening in a basic environment (Fontaine et al., 2015), we incubated both peptides at 37° C. overnight. Ring-opening completion was checked before trypsin addition. Doing so, we avoided overlapping of N-terminal digest fragments resulting from α-existing succinimidyl thioether and succinamic acid thioether peptides. Along this treatment, minor foot-peaks appeared besides the major peak, which was linked with the well-known side reaction of deamidation and concomitant isomerization, leading to aspartyl and isoaspartyl forms of the peptides (Yang et al., 2010). Lyophilized trypsin (Thermo scientific) was reconstituted using 50 mM acetic acid, diluted with 50 mM ammonium bicarbonate and added to the peptide solution so as to obtain a final peptide concentration of 0.25 mg/mL and a protease to protein ratio of 1:20 (w/w). Samples were directly incubated on the injection sampler thermostated at 37° c. HPLC and LC-MS analyses were performed as previously described above, applying a 15% to 40% linear gradient of acetonitrile in 10 mM ammonium acetate over 20 minutes. An *Aeris* Peptide 3.6μ XB-C18 column was employed for LC-MS analysis of the L-peptide digest fragments, which were identified in positive electrospray ionization mode (data not shown).

Cell Biology and Neutrophil Fractionation

Ethics. All participants gave written informed consent in accordance with the Declaration of Helsinki principles. Peripheral Human blood was collected from healthy patients at the ICAReB service of the Pasteur Institut (authorization DC No.2008-68). Hematopoietic Stem Cells were purified from cytapheresis products collected from healthy patients stimulated 5 days with G-CSF at the Gustave Roussy Cancer Campus (Villejuif, France). Human blood was collected from the antecubital vein into tubes containing sodium citrate (3.8% final) as anticoagulant molecules.

Polymorphonuclear neutrophils purification. Human polymorphonuclear neutrophils were purified as described previously (Monceaux et al. 2016). Briefly, plasma was removed by centrifugation (450×g, 15 min); blood cells were resuspended in 0.9% NaCl solution supplemented with 0.72% Dextran. After red blood cells sedimentation, white blood cells were pelleted and further separated on a two layer Percoll (GE Healthcare) (51%–42%) by centrifugation (at 240×g, 20 min). PBMC (top layer) were isolated from polymorphonuclear neutrophils (bottom layer). Red blood cells were removed from the latter fraction using CD235a (glycophorin) microbeads (negative selection) (Miltenyi Biotec). PBMCs and polymorphonuclear neutrophils were resuspended in the autologous plasma. Guinea pig and mouse polymorphonuclear neutrophils were purified with the same procedure.

Hematopoietic Stem cells (CD34+) purification, proliferation and differentiation. HSC were purified from cytapheresis products with a CD34 Microbead Kit Ultrapure, according to the manufacturer procedure (Miltenyi). Lin−/CD34+ HSC purity yield was >98%. CD34+ HSC were cultured in StemSpan SFEM II supplemented with SCF (100 ng/ml), IL-3 (10 ng/ml), and IL-6 (100 ng/ml) at 37° C. with 5% $CO_2$. Neutrophil differentiation was induced in StemSpan SFEM II containing G-CSF (10 ng/ml), SCF (100 ng/ml), and IL-3 (10 ng/ml) for 13 days at 37° C. with 5% $CO_2$.

Bacterial strains and growth conditions. *Shigella flexneri* 5a pGFP (M90T) strain was grown in GCTS broth or on TCS agar plates supplemented with 0.01% Congo Red (Sigma-Aldrich) and Ampicillin (100 lag/ml). *Shigella sonnei* was acquired from the Institut Pasteur strain collection (CIP 106347) and is a clinical isolate from a 1999 Paris infection. The strain was grown in GCTS supplemented with Ampicillin (100 µg/ml) to maintain the pMW211 plasmid.

Neutrophil infection. Human purified neutrophils were cultured in glass-bottom dishes (Mattek) for live fluorescent microscopy in a RMPI 1640 (Life Technologies) culture medium supplemented with 10% of heat inactivated Human Serum (Sigma-Aldrich). Neutrophils ($5.10^5$ cell/mL in 2 mL) were infected with exponentially-grown *Shigella flexneri* 5a pGFP at a Multiplicity Of Infection (MOI) 20 in RMPI 1640 (Life Technologies) culture medium supplemented with 10 mM Hepes (Life Technologies) at 37° C. Infected neutrophils were centrifuged at 2000 rpm for 10 min prior imaging.

Animal Models of Shigellosis

Guinea pig. The experimental protocol was approved by the french Ethic Committee Paris (n° 20140069, 2014). Young guinea pigs (Hartley, <150 g, Charles River) were anaesthetized and infected intrarectally with $10^9$ CFU exponentially grown *Shigella flexneri* 5a (M90T) pGFP as previously described (Shim et al. 2007) (Monceaux et al. 2016). Infection occurred during 8 hours before animals were sacrificed and infected colons collected and fixed in 4% Paraformaldehyde (PFA) for two hours. For immunohistochemical staining, infected guinea pig colon samples were washed in PBS and incubated at 4° C. in PBS containing 16% sucrose for 4 hours, followed by incubation in PBS with 30% sucrose overnight. Samples were frozen in OCT (VWR 361603E) on dry ice. Frozen blocks were stored at −80 until sectioning. 10 to 30 µm sections were obtained using a cryostat CM-3050S (Leica). Tissue slices were labeled in PBS+0.1% saponin (Sigma-Aldrich) with $MUB_{40}$-Cy5 or MUB40-Dylight (1 µg/ml) to localize recruited neutrophils. Slides were washed three time in PBS+0.1% saponin, three times in PBS, and three times in deionized $H_2O$ and mounted with prolong gold$^{tm}$ mounting media.

Mouse. The experimental protocol was approved by the french Ethic Committee Paris (number 20150042). Female 6 week-old BALB/cJRi mice from Charles River were orally gavaged with streptomycin (100 µL of 200 mg/ml solution) 24 hours prior to *Shigella sonnei* infection. Mice were orally gavaged with $10^{10}$ CFUs *S. sonnei* carrying pMW211 expressing DsRed and monitored for 24 hours. At the end of the experiment, animals were sacrificed and tissue sections from the colon were extracted. Colon sections were placed in 4% paraformaldehyde (PFA) solution for 2 hours. PFA fixed tissue sections were passaged for 16 hours in 16% sucrose followed by 4 hours in 30% sucrose solutions. Fixed colon slices were embedded in OCT (VWR 361603E) and flash frozen in dry ice chilled 2-methylbutane. Frozen blocks were stored at −80 until sectioning. A Leica CM3050S cryostat was used to cut 30 µM thick colon slices, which were absorbed to glass microscope slides. Tissue slices were prepared for fluorescence microscopy by incubation in 0.1% saponin for 1 hour followed by incubation with fluorescent markers specific for actin (phalloidin-FITC, Life Technology) and $MUB_{40}$-Cy5 at a final 1 µg/ml concentration. Slides were washed in deionized $H_2O$ and mounted with prolong gold$^{tm}$ mounting media.

Rabbit. The experimental protocol was approved by the french Ethic Committee Paris 1 (number 20070004, December 9th 2007). New Zealand White rabbits weighting 2.5-3 kg (Charles River) were used for experimental infections. For each animal, up to 12 intestinal ligated loops, each 5 cm in length, were prepared as described previously (Jones et al. 2007; Martinez et al. 1988; West et al. 2005) and infected with $10^5$ CFU *S. flexneri* pGFP per loop. After 16 h, animals were sacrificed and collected tissue were fixed in 4% Paraformaldehyde (PFA) for two hours. For immunohistochemical staining, infected rabbit ileum samples were washed in PBS, incubated at 4° C. PBS containing 12% sucrose for 90 min, then in PBS with 18% sucrose overnight, and frozen in OCT (Sakura) on dry ice. 7 µm sections were obtained using a cryostat CM-3050 (Leica). Fluorescent staining was performed in PBS+0.1% saponin using Phalloidin-RRX (1:1000 dilution) to stain Actin, $MUB_{40}$-Cy5 (1 µg/mL) and a mouse anti-lactoferrin primary monoclonal antibody (Hycult biotech, clone 265-1K1, 1:50 dilution) and an anti-mouse-FITC conjugated secondary antibody (1:1000) to stain infiltrated neutrophils. Slides were washed three time in PBS+0.1% saponin, three times in PBS, and three times in deionized $H_2O$ and mounted with prolong gold$^{tm}$ mounting media.

Mass Spectrometry Analyses

Digestion of proteins. Coomassie-stained bands detected on gel were cut and rinsed three times in a 50/50 mix of water/acetonitrile (ACN). Proteins were reduced (10 mM Dithiothreitol (DTT)) and further alkylated (50 mM Iodoacetamide) in-gel. In-gel tryptic digestion was performed by adding 400 ng sequencing grade modified trypsin (Promega France, Charbonnières, France) in 50 mM $NH_4HCO_3$ for 18 h at 37° C. Tryptic peptides were recovered by washing the gel pieces twice in 0.5% FA-50% ACN and once in 100% acetonitrile, and all supernatants were collected in the same tube and evaporated to almost dryness.

LC-MS/MS of tryptic digest. Digested peptides were analyzed by nano LC-MS/MS using an EASY-nLC 1000 (Thermo Fisher Scientific) coupled to an Orbitrap Q Exactive HF mass spectrometer (Thermo Fisher Scientific, Bremen). Half of each sample was loaded and separated at 250 nl·min$^{-1}$ on a home-made $C_{18}$ 30 cm capillary column picotip silica emitter tip (75 µm diameter filled with 1.9 µm Reprosil-Pur Basic $C_{18}$-HD resin, (Dr. Maisch GmbH, Ammerbuch-Entringen, Germany)) equilibrated in solvent A (0.1% FA). Peptides were eluted using a gradient of solvent B (ACN, 0.1% FA) from 2% to 5% in 5 min, 5% to 35% in 30 min, 30% to 50% in 5 min at 250 nL/min flow rate (total length of the chromatographic run was 50 min including high ACN level steps and column regeneration). Mass spectra were acquired in data-dependent acquisition mode with the XCalibur 2.2 software (Thermo Fisher Scientific, Bremen) with automatic switching between MS and MS/MS scans using a top-15 method. MS spectra were acquired at a resolution of 60000 with a target value of $3\times10^6$ ions. The scan range was limited from 300 to 1700 m/z. Peptide fragmentation was performed via higher-energy collision dissociation (HCD) with the energy set at 28 NCE. Intensity threshold for ions selection was set at $1\times10^5$ ions with charge exclusion of z=1 and z>6. The MS/MS spectra were acquired at a resolution of 17500 (at m/z 400). Isolation window was set at 2 Th. Dynamic exclusion was employed within 30 s.

Data were searched using MaxQuant[1] (version 1.5.3.8) (with the Andromeda search engine) against a human database (20202 entries, downloaded from Uniprot the 2016.05.26).

The following search parameters were applied: carbamidomethylation of cysteines was set as a fixed modification, and oxidation of methionine and protein N-terminal acetylation were set as variable modifications. The mass tolerances in MS and MS/MS were set to 5 ppm and 20 ppm, respectively. Maximum peptide charge was set to 7, and 5 amino acids were required as minimum peptide length. Results were filtered by a 0.01 false discovery rate at both protein and peptide levels.

Microscopy and Image Analysis

Confocal microscopy. Fixed cells (polymorphonuclear neutrophils, PBMC, haematopoietic stem cells), guinea pig colon and rabbit ileum infected with *S. flexneri* pGFP were imaged on a laser-scanning TCS SP5 confocal microscope (Leica). Z-stack images were taken with 1 μM step-size increments. Obtained Z-stack images were processed with Fiji software Spinning disk microscopy. Mouse colons infected with *S. sonnei* pDsRed were imaged on a Bruker Opterra fluorescence microscope using a Zeiss Plan-Apochromat 63×/1.40 oil immersion lense and Prairie View software version 5.3. Z-stack images were taken with 0.5 μM step-size increments. Obtained Z-stack images were stitched with Fiji software version 2.0.0-rc-30/1.49u and visualized using IMARIS software version 8.3.1.

Figure 16A:
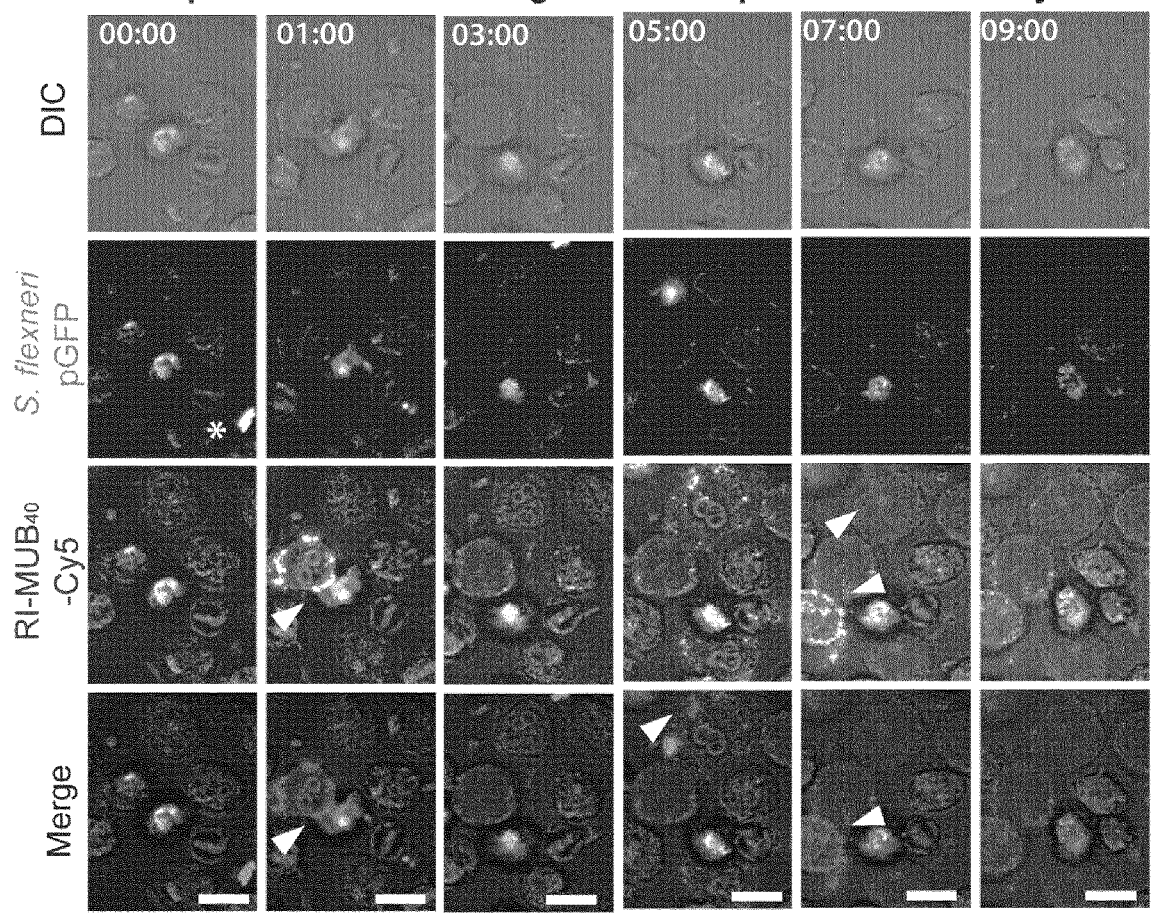
Figure 16B:
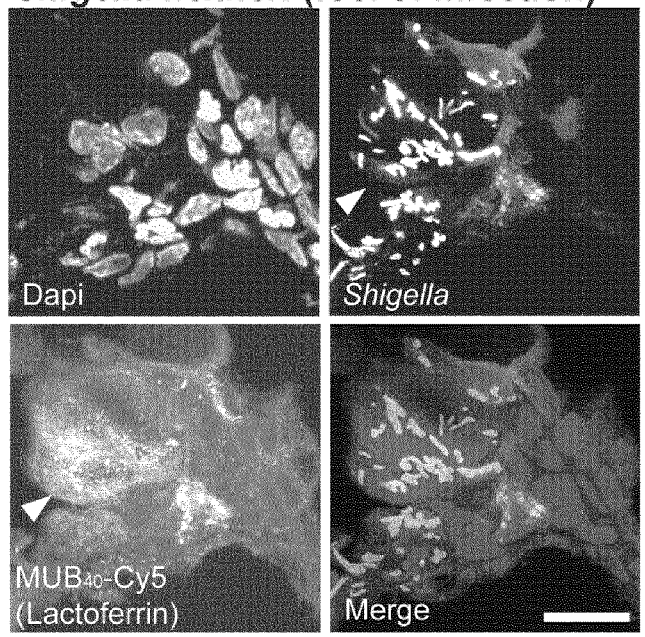

Live epifluorescence microscopy. Viable neutrophils infected with *S. flexneri* pGFP were imaged on a Definite focus live microscope (Zeiss) equipped with a temperature control chamber (37° C.) and a 63× oil immersion objective. Images were acquired every 60 s. Z-stack images were taken with 2 μM step-size increments. Obtained Z-stack images were processed with Fiji software to generate a Movie and the corresponding extracted images are shown in FIG. 16a.

Two-photons microscopy. Human colonic tissue segments infected with *S. flexneri* pGFP were imaged using a commercial laser-scanning microscope (LSM710, Meta, Zeiss, Germany) as described previously (Tyanova et al. 2016). $MUB_{40}$-Cy5 was detected using multiphoton excitation (MPE, magenta), Acquisitions were performed with Zen 2008 SP 1.1 software acquisition package developed by ZEISS. Imaris software (http://www.bitplane.com) was used to prepare final images.

B. Results $MUB_{40}$-Peptides Chemical Synthesis, Structure, and Binding Properties $MUB_{40}$ is a 40-amino acid peptide, derived from the $MUB_{70}$ marker, originally characterized for its ability to bind the human colonic mucus (Coïc et al., 2012). Four overlapping 40-amino acid peptides (named $MUB_{40}$#1 (SEQ ID NO: 3), $MUB_{40}$#2 (SEQ ID NO: 4), $MUB_{40}$#3 (SEQ ID NO: 5), and $MUB_{40}$#4) (SEQ ID NO: 6) covering the $MUB_{70}$ sequence were designed (FIG. 1A), chemically synthesized (see Methods), and conjugated to fluorophore or biotin via the N-ter added cysteine when required for further study (see Methods). The $MUB_{40}$ peptide synthesis strategy was set up based on $MUB_{70}$ synthesis (Coïc et al., 2012), incorporating secondary amino acid surrogates (Dmb and pseudoproline dipeptides (FIG. 2A). As a result, lowering of aggregation propensity and aspartimide formation produced the $MUB_{40}$ peptide with a satisfactory yield.

Figure 1B:
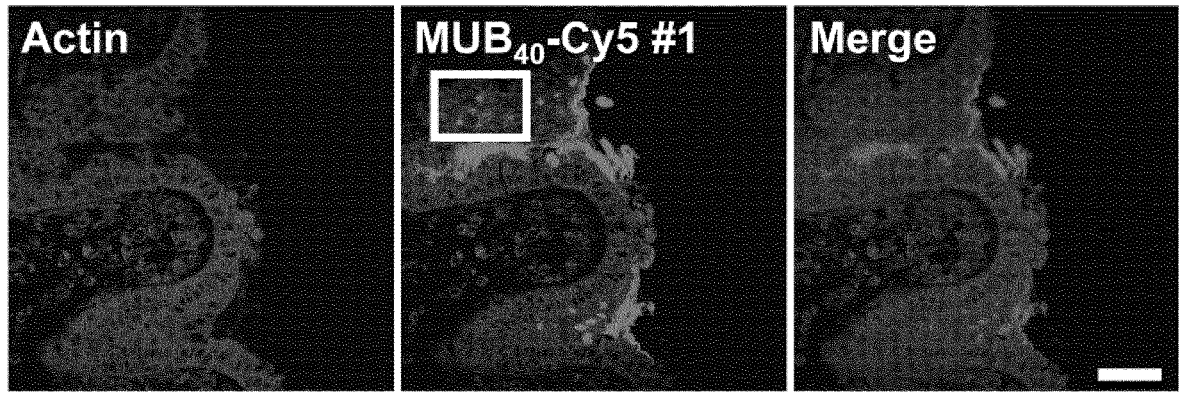
Figure 1C:
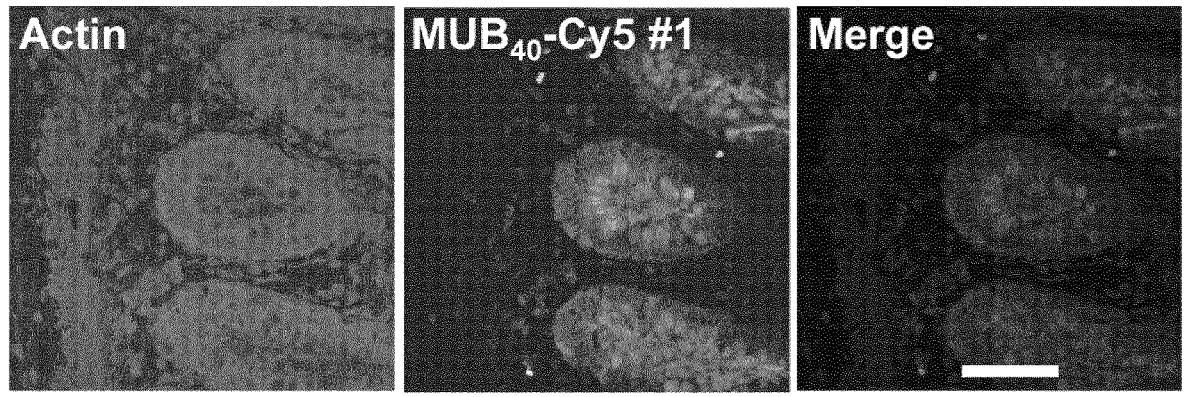
Figure 1D:
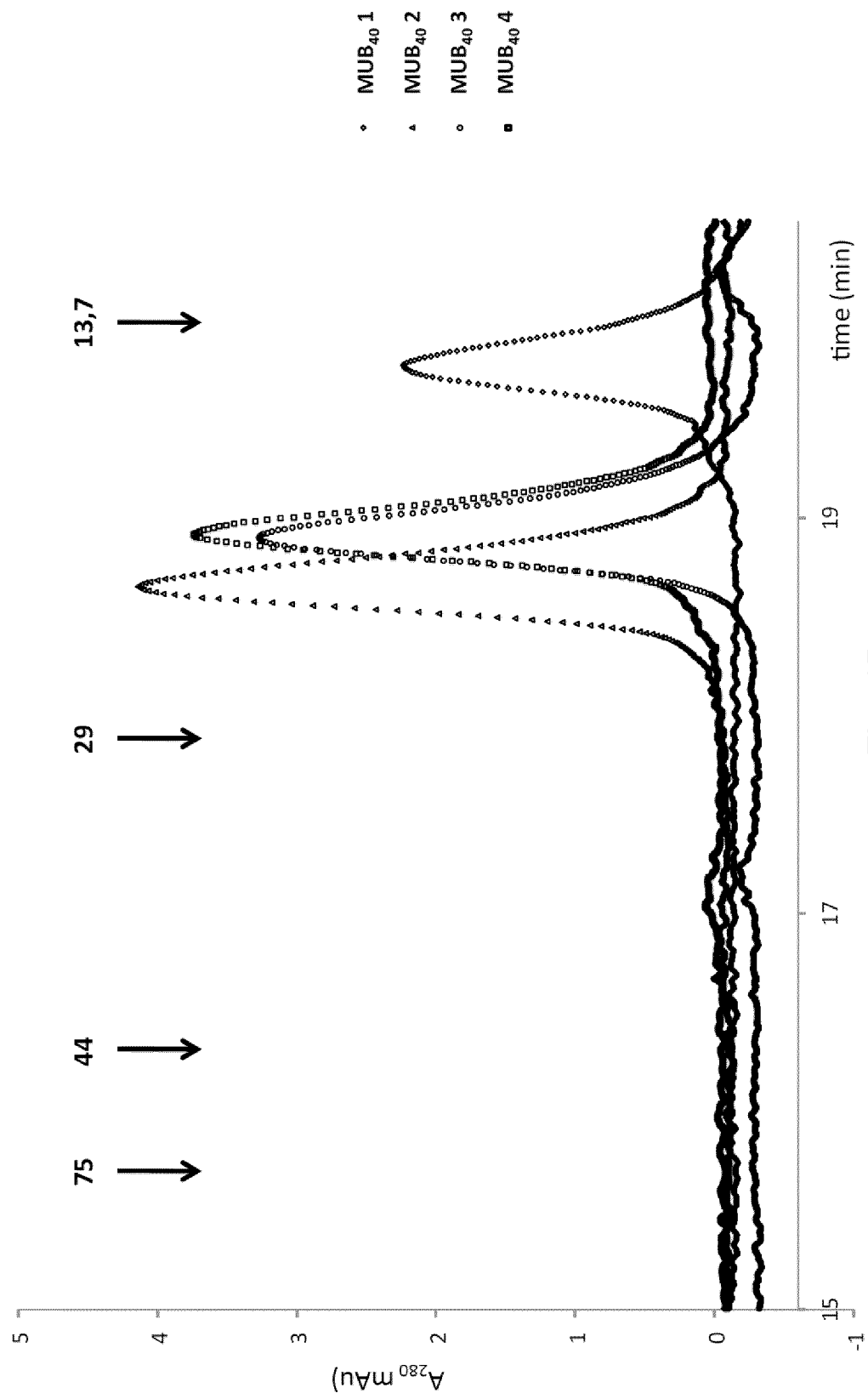
Figure 2B:
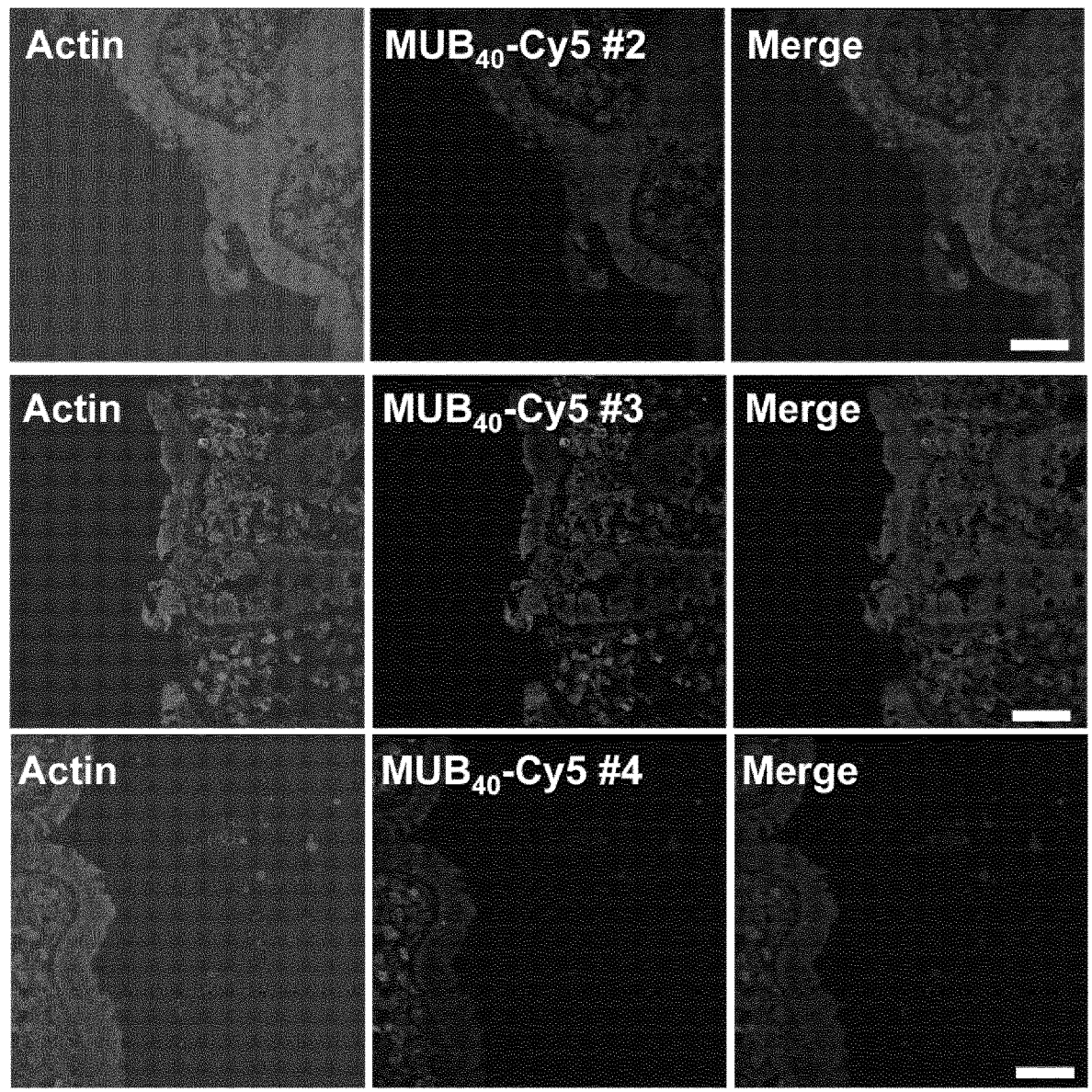

$MUB_{40}$#1 (SEQ ID NO: 3) (corresponding to $MUB_{70}$ C-terminal part), conjugated to Cy5 ($MUB_{40}$#1-Cy5) was the only peptide, which conserved the ability to bind to and fluorescently label the human colonic mucus (FIGS. 1B and 2B). In contrast with $MUB_{70}$-Cy5 (SEQ ID NO: 11), $MUB_{40}$#1 (SEQ ID NO: 3)-Cy5 allowed in addition the labelling of goblet cell granules on fixed slides, most likely due to its reduced size and the resulting improved accessibility to granule content (FIG. 1C). Similarly to $MUB_{70}$ (SEQ ID NO: 11) (Coïc et al., 2012), the inventors show here by Analytical Gel Filtration (see Methods) that $MUB_{40}$#1 (SEQ ID NO: 3) (theorical MW 4.9 kDa), combined as a trimer (experimental Mr 15.9 kDa), unlike the three others overlapping peptides which rather organized as tetramers ($MUB_{40}$#2 (SEQ ID NO: 4) theo MW 4.8 kDa; exp: Mr 22.0 kDa, $MUB_{40}$#3 (SEQ ID NO: 5) theo MW 4.9 kDa; exp Mr 20.5, and $MUB_{40}$#4 (SEQ ID NO: 6) theo MW 4.8 kDa; exp Mr 20.4 kDa) (FIG. 1D).

MUB70 (SEQ ID NO: 11) was also previously found to assemble as a trimer, as evidenced by analytical gel filtration (Coïc et al., 2012). Further, among the four 40-AAs MUB40 polypeptides disclosed in WO 2013/034749 A1 (SEQ ID NOS: 3-6), the inventors validated that one kept the mucus-binding property, i.e. probe MUB40 #1 (SEQ ID NO: 3)-Cy5. In fact, the inventors have previously shown that the C-terminal part of MUB70, i.e. the part covered by MUB40 #1 probe (SEQ ID NO: 3) in WO 2013/034749 A1, adopt a trimeric organization as compared to its theoretical molecular weight. On the contrary, MUB40 #2 (SEQ ID NO: 4), MUB40 #3 (SEQ ID NO: 5) and MUB40 #4 (SEQ ID NO: 6) probes have presently been shown to adopt a different multimeric status in phosphate buffer as shown in FIG. 1D. The inventors therefore surprisingly concluded that as a matter of fact, staining properties of MUB polypeptides derivatives correlates with their propensity to organize as a trimer.

Figure 1E:
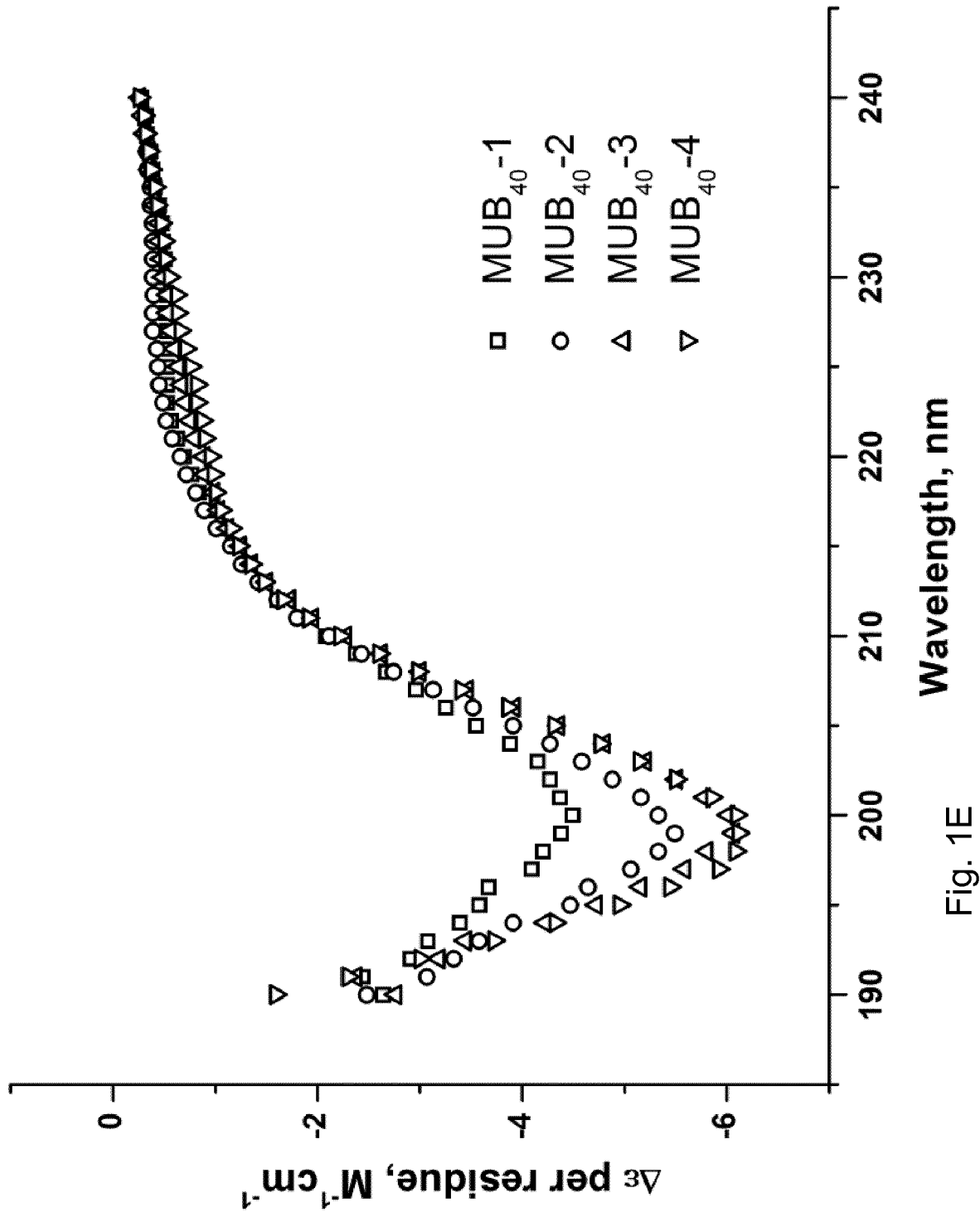
Figures 1F, 1G:
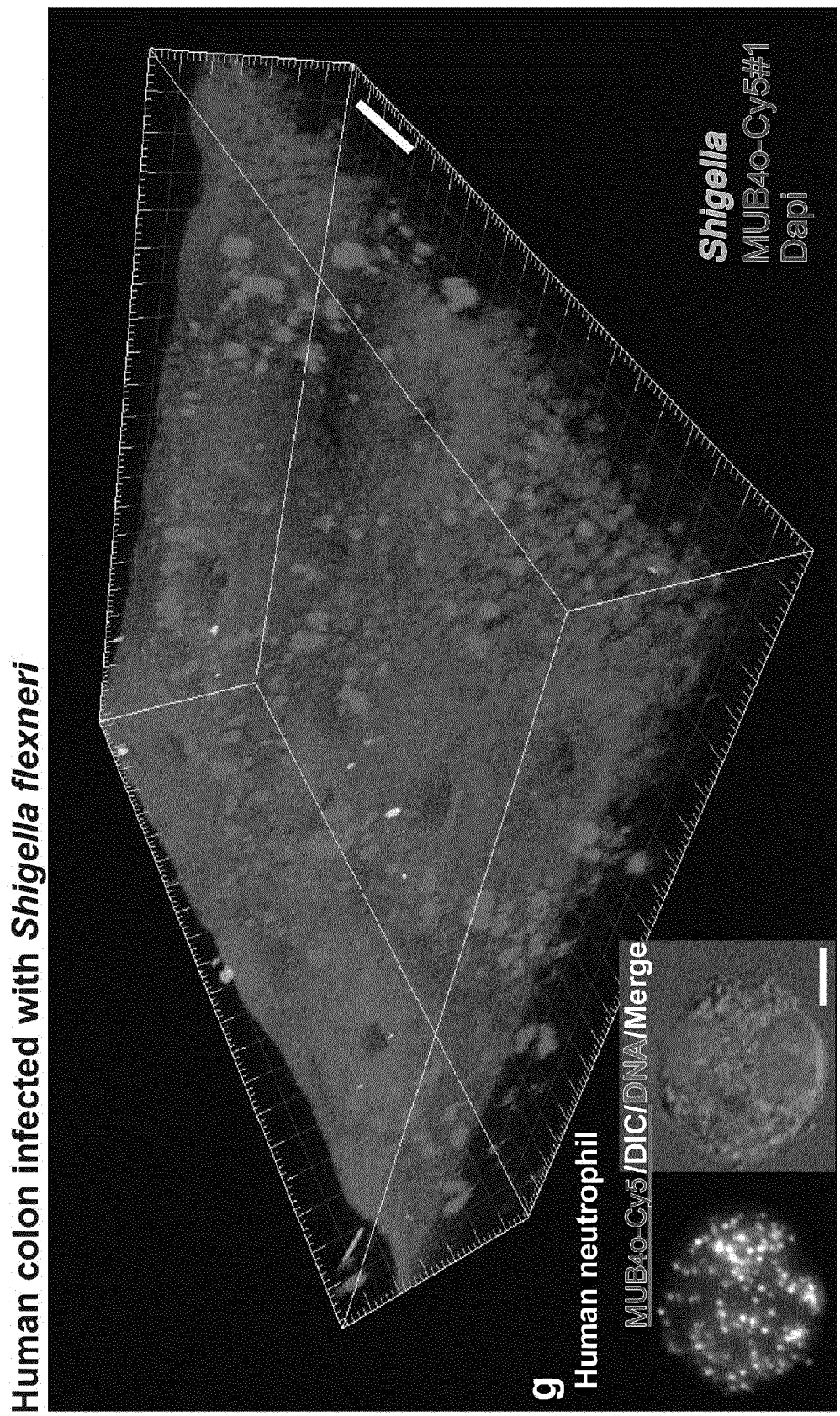

$MUB_{40}$ peptides were almost similarly shaped and could be assigned to unstructured peptide chains or polyproline II-like scaffolds (by Circular Dichroism, see Methods) (FIG. 1E). Nevertheless, slight differences were also observed between the CD spectra, mostly in the negative band within the 200 nm range: $MUB_{40}$#1 (SEQ ID NO: 3) showed a lower intensity signal, significantly 1 to 1.5 nm red-shifted, as compared to other $MUB_{40}$ peptides (#2, #3 and #4) (SEQ ID NOS: 4-6) minima: this singularity could reflect a specific feature of $MUB_{40}$#1. As a conclusion, $MUB_{40}$#1, hereafter-named $MUB_{40}$, highlighted a similar oligomerization state and mucus-binding properties compared to $MUB_{70}$ and was thus further characterized in this study.

Also, as reported before, inflammatory tissues can be associated with mucus pathological accumulation. The specific labelling of these inflammatory samples was assessed with MUB40 #1 (SEQ ID NO: 3). As an example, colonic mucinous carcinoma, which was demonstrated to be specifically labelled with the original MUB70 peptide (Coïc et al., 2012), was similarly labelled with MUB40 #1, together with an anti-Muc2 antibody. The accumulation of Muc2 in this pathology was additionally confirmed (FIG. 3).

The inventors also demonstrated in vitro that cystic fibrosis (CF) patients sputum was labeled with MUB40 #1 (SEQ ID NO: 3)-Cy5, together with anti-Muc2 and anti-Muc5ac monoclonal antibodies (FIG. 4).

$MUB_{40}$ Labels Human and Other Mammalian Granulocytes

In addition to its colonic mucus binding property, confirmed on fixed human colon explants infected with *Shigella flexneri* (*S. flexneri*) (FIG. 1F, see Methods), $MUB_{40}$ (SEQ ID NO: 3)-Cy5 labelled a specific cell population in the colonic mucosa, which were hypothesized to be polymorphonuclear neutrophils (neutrophils), the most abundant immune cell population recruited upon *Shigella* invasion (Sansonetti et al., 1999). To confirm this hypothesis, human neutrophils were purified from healthy volunteers (see Methods). When incubating fixed purified human neutrophils with $MUB_{40}$ (SEQ ID NO: 3)-Cy5, a fluorescent labelling was confirmed and appeared to be granular (FIG. 1G), suggesting that $MUB_{40}$ target was stored in neutrophil granules.

Figure 5A:
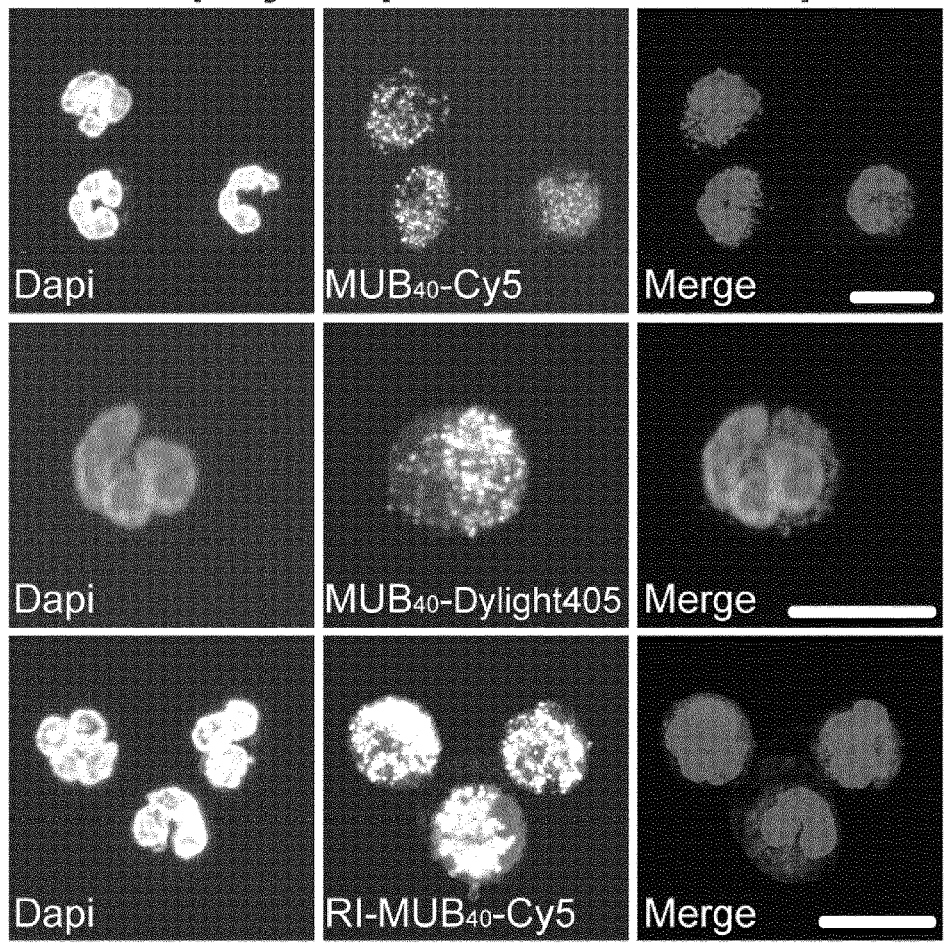
Figure 5B:
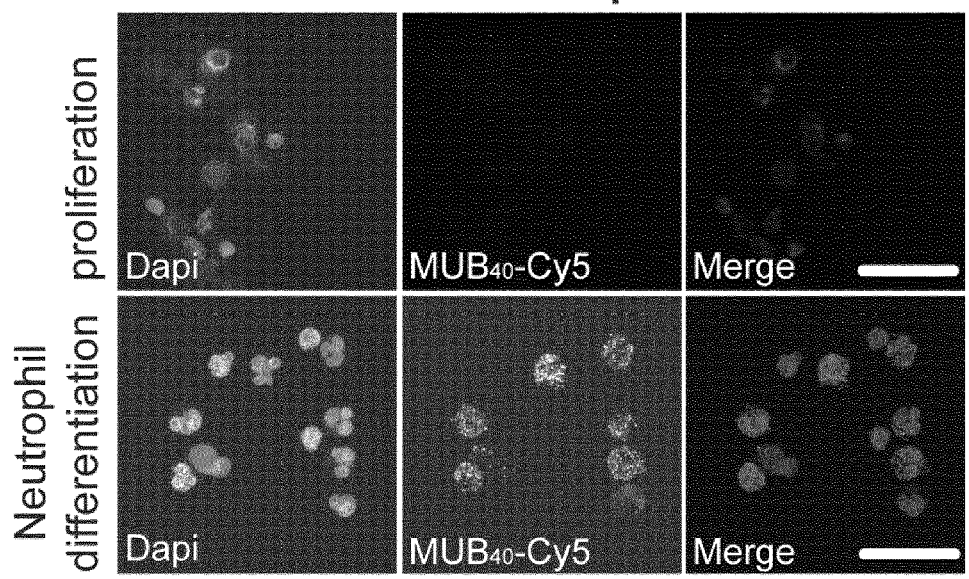

The inventors further confirmed that regardless of the fluorophore conjugated to $MUB_{40}$ ($MUB_{40}$ (SEQ ID NO: 3)-Cy5 or $MUB_{40}$ (SEQ ID NO: 3)-Dylight405, see Methods), human neutrophil granules were specifically labeled (FIG. 5A), but not peripheral blood mononuclear cells (PBMC), encompassing B lymphocytes (CD19), T lymphocytes (CD3), and monocytes/macrophages (CD14) (FIG. 6). Neutrophils differentiate from pluripotent haematopoietic stem cells (HSC, CD34+) in the bone marrow during granulopoiesis, characterized by the formation of promyelocytes, myelocytes, metamyelocytes, band cells, segmented neutrophilic cells, and mature neutrophils. To assess the specificity of mature neutrophil labelling with MUB40-Cy5, hematopoietic stem cells were purified from cytapheresis product and differentiated to neutrophils (see Methods). The inventors confirmed that MUB40-Cy5 did not label human hematopoietic stem cells until their differentiation into mature neutrophils in vitro (FIG. 5B).

Figure 7A:
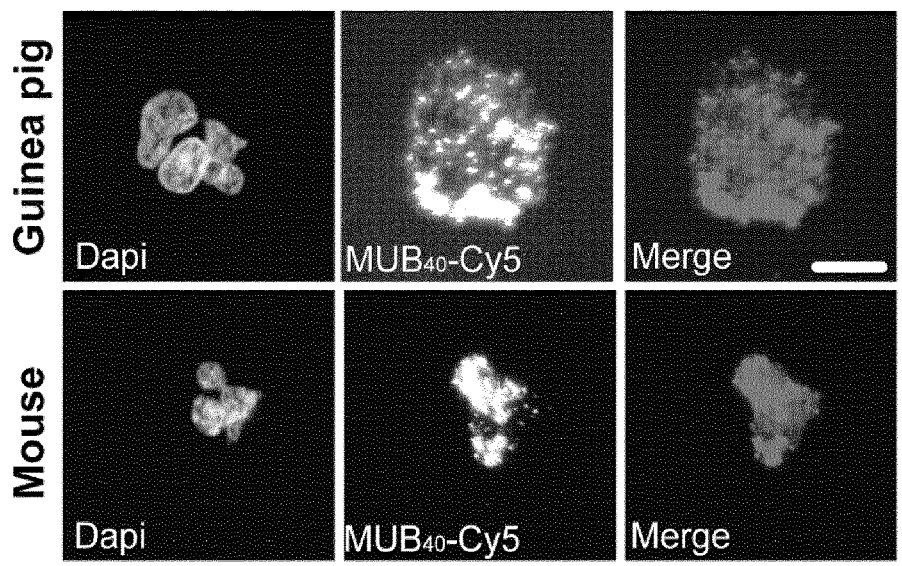
Figure 7B:
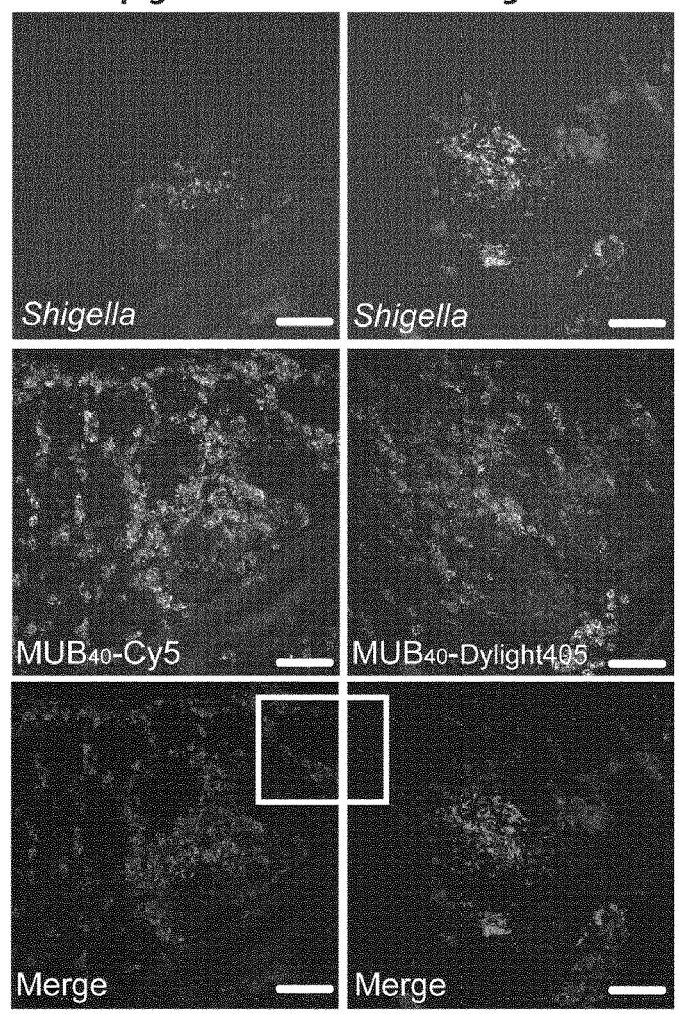
Figure 7C:
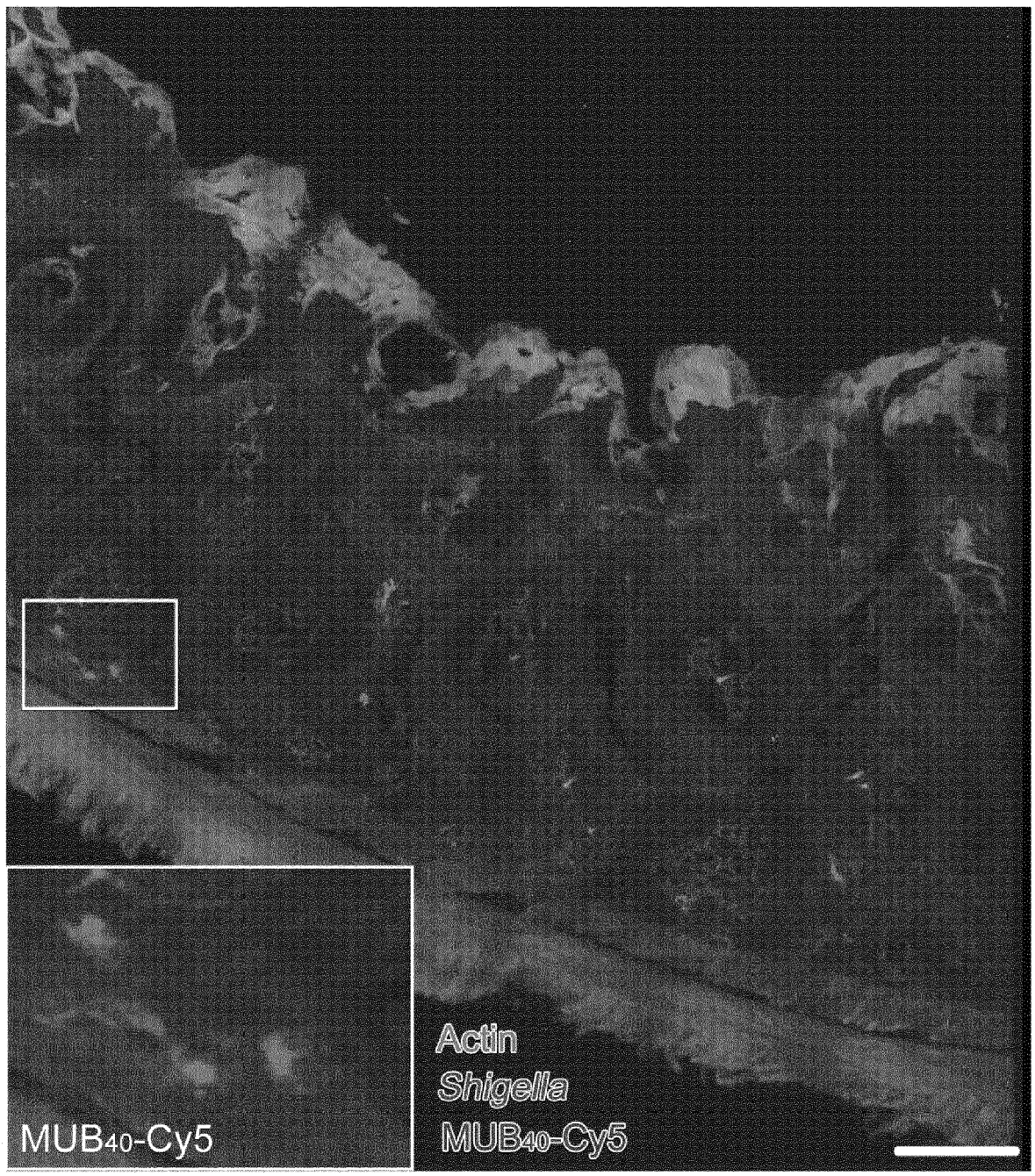

The inventors have here demonstrated that all mammalian neutrophils tested were efficiently labeled with $MUB_{40}$-(SEQ ID NO: 3) Cy5, as illustrated with mouse and guinea pig circulating neutrophils (FIG. 7A). In animal models of shigellosis (see Methods), neutrophils recruited to the intestinal mucosa infected with Shigella were specifically labeled with $MUB_{40}$ (SEQ ID NO: 3)-Cy5 or $MUB_{40}$ (SEQ ID NO: 3)-Dylight405, as illustrated in guinea pig colon (Shigella flexneri; $MUB_{40}$ (SEQ ID NO: 3)-Cy5 or $MUB_{40}$ (SEQ ID NO: 3)-Dylight405, FIG. 7B), mouse colon (Shigella sonnei, $MUB_{40}$ (SEQ ID NO: 3)-Cy5, FIG. 7C, described in (Anderson et al., 2017)), and rabbit ileum (Shigella flexneri, $MUB_{40}$ (SEQ ID NO: 3)-Dylight405, FIG. 8).

These results confirm the potential use of $MUB_{40}$ peptide as a specific neutrophil marker in physiological and pathophysiological conditions, in humans and in various animal models. The inventors next aimed at synthesizing the so-called RI-MUB40 polypeptide and identifying the specific $MUB_{40}$ (and RI-MUB40) target(s) in neutrophil granules.

Figure 5C:
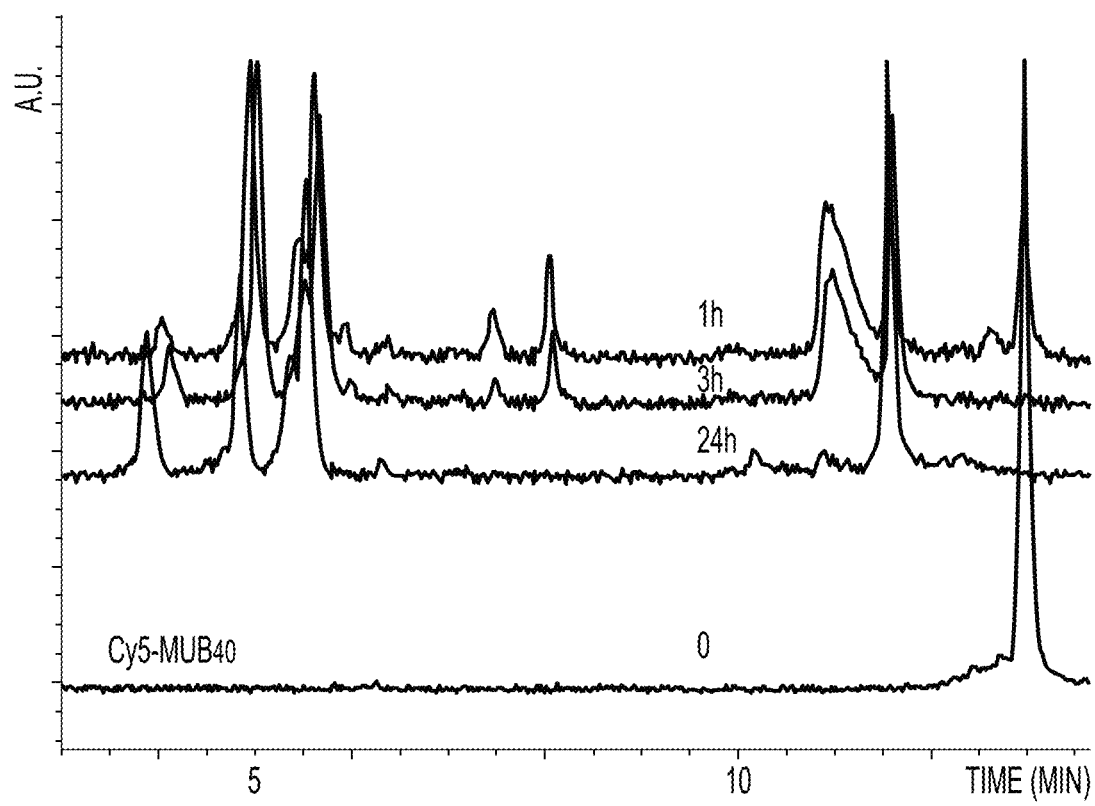
Figure 5C:
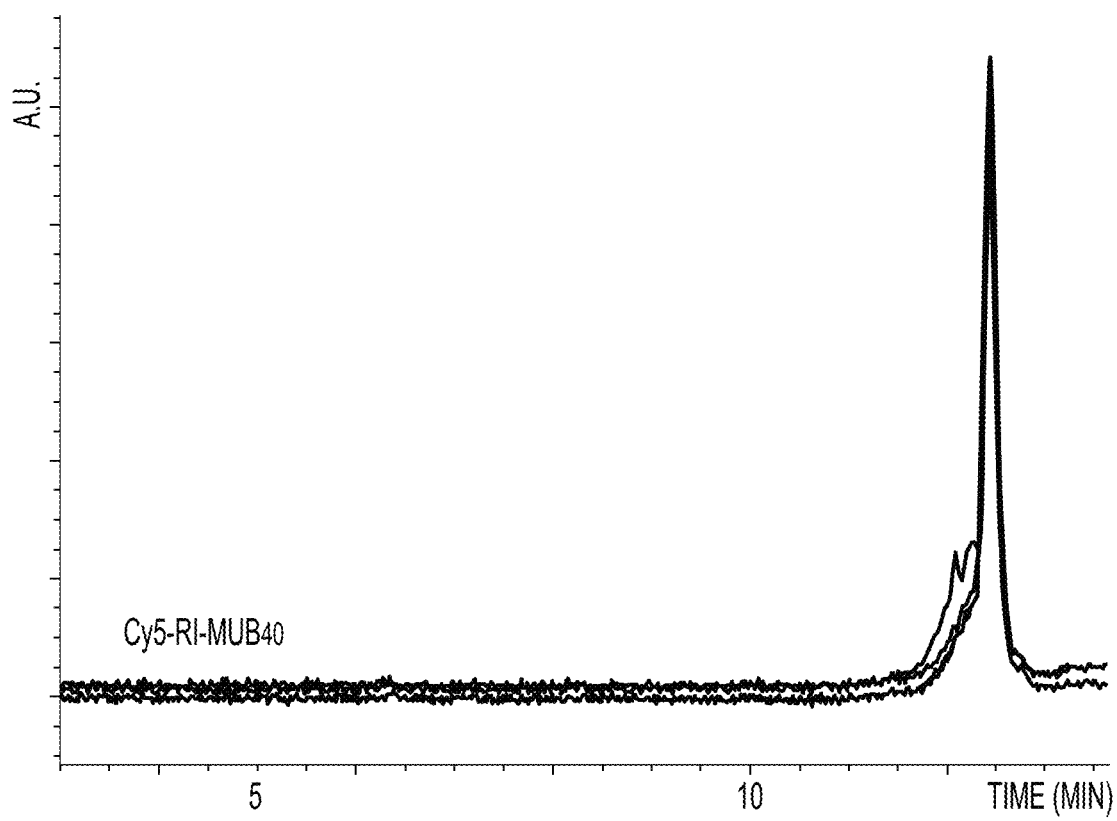
Figure 5D:
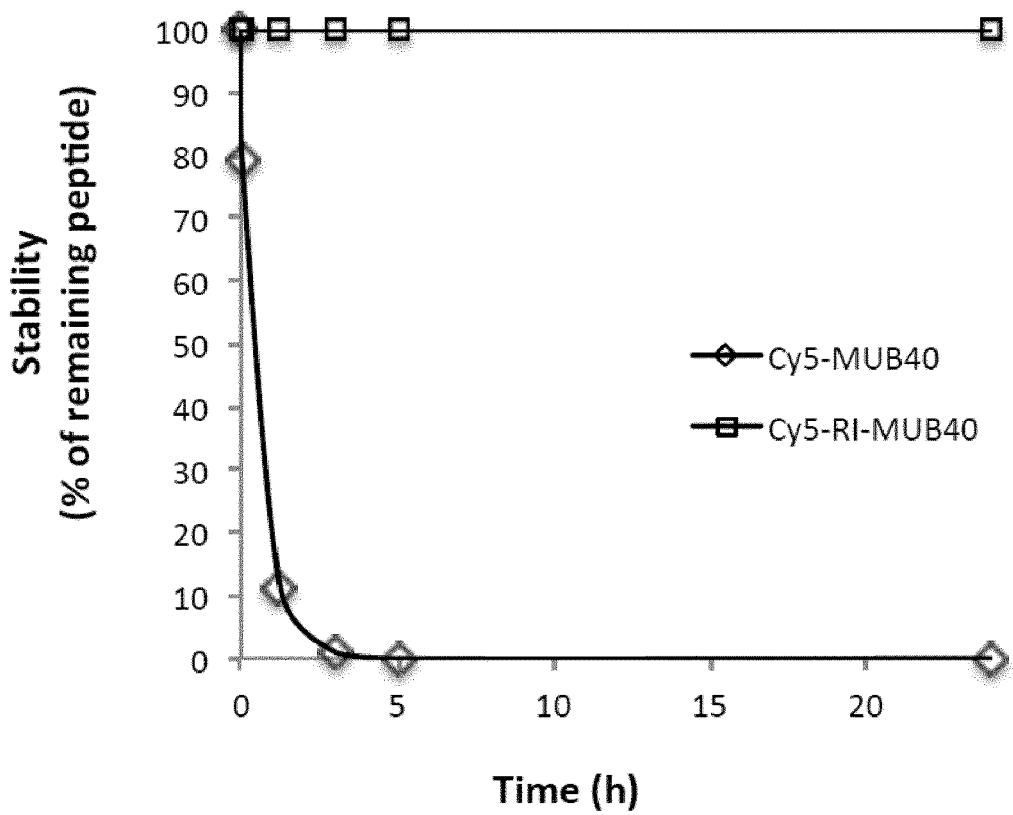

In fact, in order to anticipate its use in the presence of living cells, a non-cleavable retro-inverso version of $MUB_{40}$, named RI-$MUB_{40}$, was synthesized with non-natural D-amino acids. RI-$MUB_{40}$ was resistant to trypsin proteolysis, whereas $MUB_{40}$ was rapidly degraded (FIG. 5C-D). The neutrophil granule binding property of RI-$MUB_{40}$ conjugated to Cy5 (RI-MUB40-Cy5) was similar to $MUB_{40}$-Cy5 (FIG. 5A). RI-MUB40 synthesis is described hereafter.

Synthesis of RI-MUB40

Considering Solid Phase Peptide Synthesis (SPPS), most of the deprotection and coupling difficulties are related to inter or intra-molecular hydrogen bonds occurring over the synthesis. N-alkylated amino-acids such as Dmb/Hmb (Johnson et al., 1995) or pseudoproline (Mutter et al., 1995) (Coïc et al., 2010) have been developed to overcome the resulting aggregation propensity of the protected peptide chain anchored to the resin. Moreover, aspartimide (Asp) formation (Mergler et al., 2003) and subsequent base-catalyzed ring-opening during Fmoc-SPPS have been described to be one of the most prevalent side reaction occurring in Asp-containing peptides, Asp-Gly sequences being particularly prone to aspartimide formation. Therefore MUB70 was obtained by using a rational incorporation of both pseudo-proline and Asp(OtBu)-(Dmb)Gly-OH dipeptides (Coïc et al, 2012).

The synthesis strategy of RI-MUB40 was designed by taking into account the commercial availability of dipeptides surrogates in the D-AAs series. Along this line, Fmoc-D-Asp(OtBu)-(Hmb)Gly-OH was incorporated instead of Asp31 and Gly32 (as referred to the Retro-Inverso sequence of SEQ ID NO: 2, D-amino-acid residues in bold and underlined), in order to minimize aspartimide formation.

MUB40 retro-inverso sequence
(SEQ ID NO: 1)
FIVTYFQDNTDDNDFKEGAPFNDKFLEYGDGEFKKIGEAT Synthesized RI-MUB40 sequence
(SEQ ID NO: 2)
acetyl-CFIVTYFQDNTDDNDFKEGAPFNDKFLEYGDGE
FKKIGEAT-amide RI-MUB40 was finally obtained with an overall isolated yield of 9%, mainly due to a major side-product corresponding to the Asp-Gly deletion peptide, suggesting a poor Hmb dipeptide coupling yield. Careful LC-MS analysis of the RI-MUB40 crude mixture allowed the inventors to clearly identify a poor Hmb-Asp-Gly dipeptide coupling step (FIG. 9) explaining the low synthesis yield obtained.

First Experimental Validation of RI-MUB40

RI-MUB40 synthesis allowed the inventors to validate conservation of mucus and neutrophil granules binding properties of retro-inverso MUB-type polypeptides.

RI-MUB40 mucus-binding properties were validated on human colonic mucus samples. The inventors confirmed that MUB40 #1-Cy5 labeled neutrophil granules, as anticipated, and demonstrated that RI-MUB40-Cy5 has similar properties (FIG. 5A). Of note, MUB40 #1 (SEQ ID NO: 3)-Cy5 also has goblet cells binding properties. In conclusion, Cy5-RI-MUB40 peptide (SEQ ID NO: 2) has been validated subsequently for its binding properties for colonic mucus (human), mucus produced by human cell lines (L174T) or neutrophil granules. For analytical studies to identify MUB40 biological targets in human colonic mucus the biotinylated RI-MUB40 peptide was also synthesized (see Material and Methods), as described hereafter.

Resistance of MUB-40 and RI-MUB40 to Enzymatic Degradation

The resistance improvement of the MUB40 retro-inverso analogue to protease degradation was evaluated through a trypsin digestion performed on the Cy5 labeled peptides (0.25 mg/mL) with a final protease to peptide ratio of 1:20 (w/w). Hydrolysis experiments were done in solution at 37° c., pH8 and monitored by HPLC by measuring the peak area of the remaining intact peptides. Unlike the L-peptide, which was almost completely degraded within 3 h, no degradation was observed for the D-peptide until 24 h, demonstrating the enhanced stability of the retro-inverso peptide (FIG. 5D and Table 1).

TABLE 1

| Time (hours) | Cy5-MUB40#1 % (SEQ ID NO: 3) of remaining peptide | Cy5-RI-MUB40 % of (SEQ ID NO: 2) remaining peptide |
|---|---|---|
| 0.033 | 90 | 100 |
| 1.25 | 13 | 100 |
| 3 | 3 | 100 |

TABLE 1-continued

| Time (hours) | Cy5-MUB40#1 % (SEQ ID NO: 3) of remaining peptide | Cy5-RI-MUB40 % of (SEQ ID NO: 2) remaining peptide |
|---|---|---|
| 5 | 0.5 | 100 |
| 24 | 0 | 100 |

MUB$_{40}$ Binds to Lactoferrin Stored in Specific and Tertiary Granules

Figure 14A:
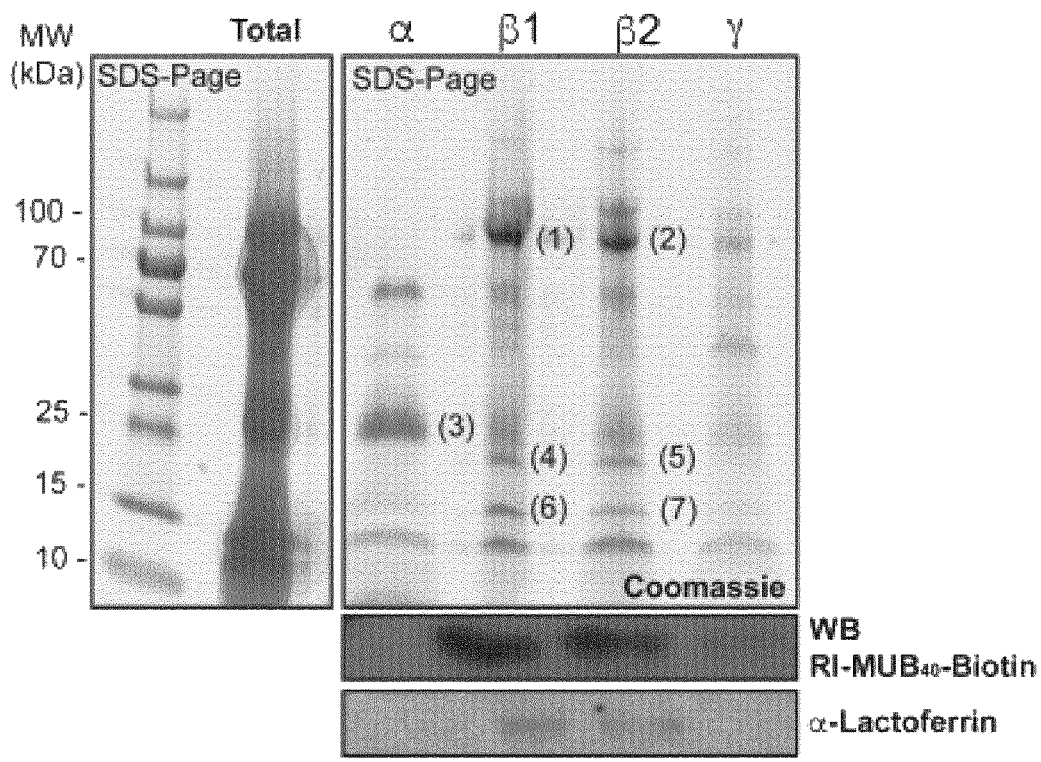

The four classes of neutrophil granules ($\alpha$, $\beta$1, $\beta$2, and $\gamma$) were fractionated on a three-layer Percoll gradient (see Methods), as previously described (Kjeldsen et al., 1999). To confirm the appropriateness of the approach the inventors subjected the different fractions to mass spectrometry and could identify the most abundant proteins stored in each granule population (see Methods): cathepsin G, neutrophil elastase, and myeloblastin in azurophil granules; lactoferrin, NGAL, cathelicidin C, and lysozyme C in specific granules; and lactoferrin, MMP-9, NGAL, cathelicidin C, and protein S100-A9 in tertiary granules, as previously reported (FIGS. 14A, 15).

Figure 14B:
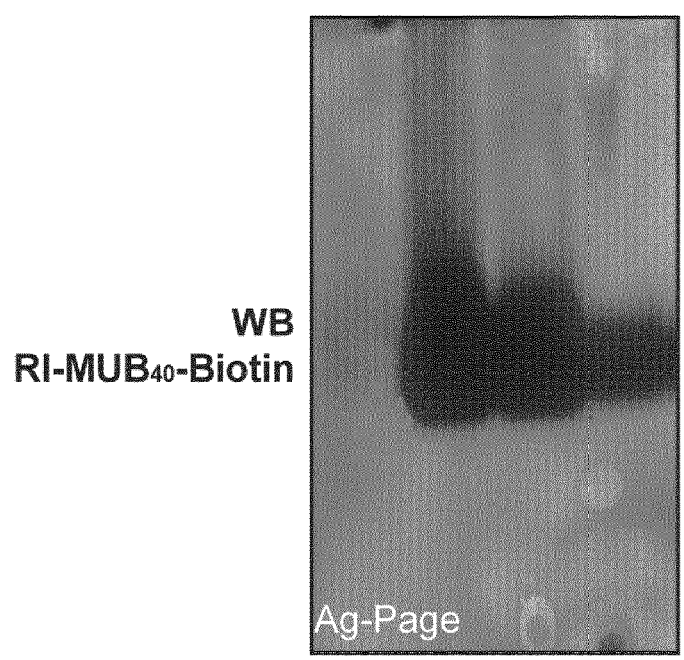

The MUB$_{40}$ target was mainly stored in specific ($\beta$1) and tertiary ($\beta$2) granules, as revealed by western blot using a biotinylated version of RI-MUB$_{40}$ (RI-MUB$_{40}$-biotin) (see Methods) when granule contents were analyzed on SDS Page gel (FIG. 14A) or on Ag-Page gel (allowing the separation of high molecular-weight complexes, see Methods) (FIG. 14B). Both approaches allowed the detection of a signal in $\beta$1/$\beta$2 fractions with RI-MUB$_{40}$-Biotin suggested that MUB$_{40}$ target were present in these samples. A stronger signal was observed when separating samples on Ag-Page, suggesting that MUB$_{40}$ target may form or be associated with high molecular complexes or aggregates. The detection of a signal on Ag-Page in the $\gamma$ fraction with RI-MUB$_{40}$-Biotin might be due to an incomplete fractionation of the complexes with this standard procedure (FIG. 14B). The propensity of lactoferrin, specifically stored in $\beta$1/$\beta$2 fractions, to polymerize in the presence of cations such as Ca$^{2+}$ or Fe$^{3+}$ (Bennett et al., 1981), (Mantel et al., 1994) is hypothesized to be responsible of this phenomenon. The granule fractionation stringency was assessed by immuno-detecting lactoferrin exclusively in specific ($\beta$1) and tertiary ($\beta$2) granules (FIG. 14A).

Figure 14C:
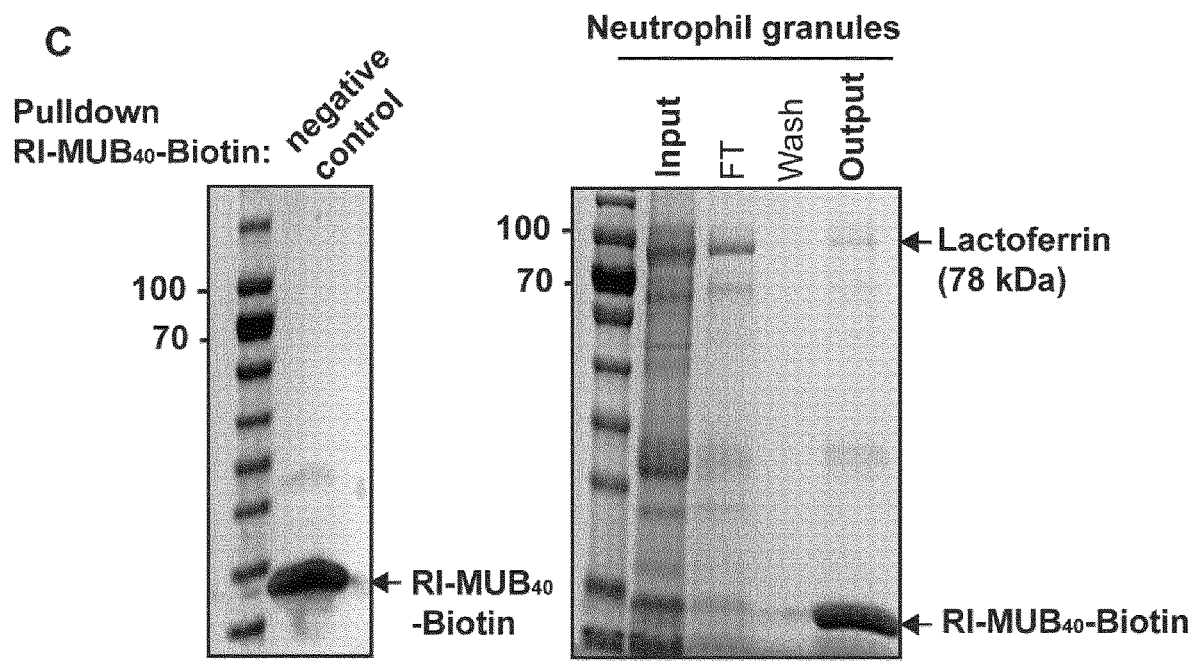
Figure 14D:
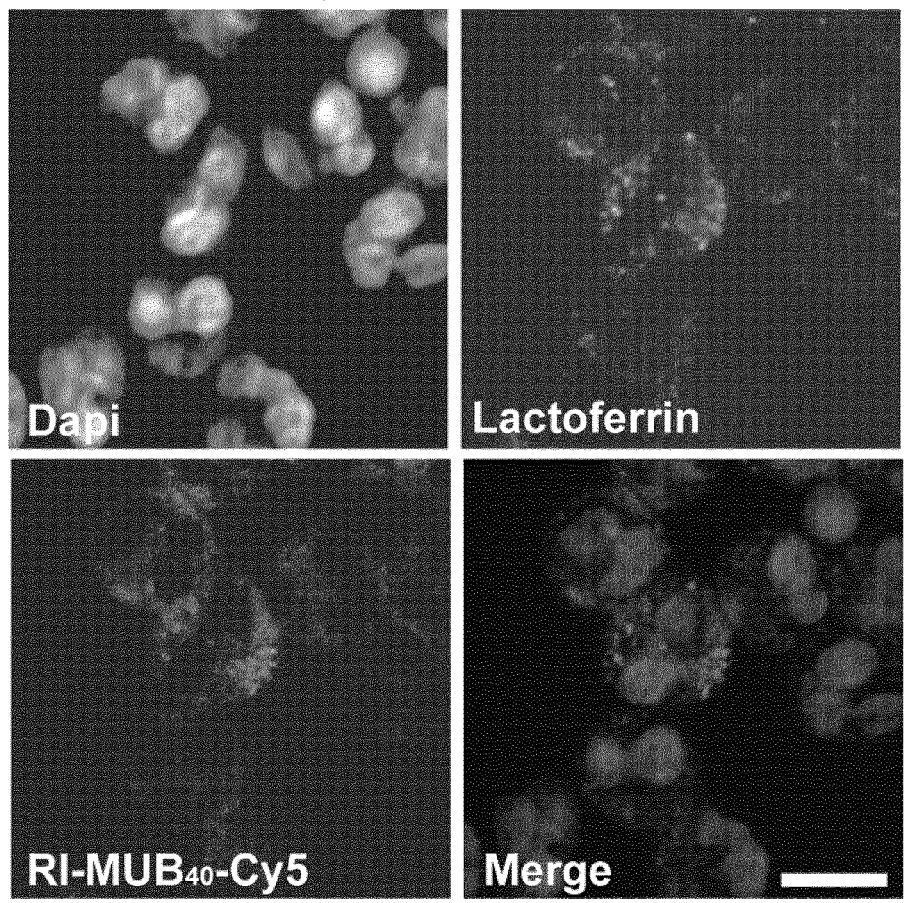
Figure 14E:
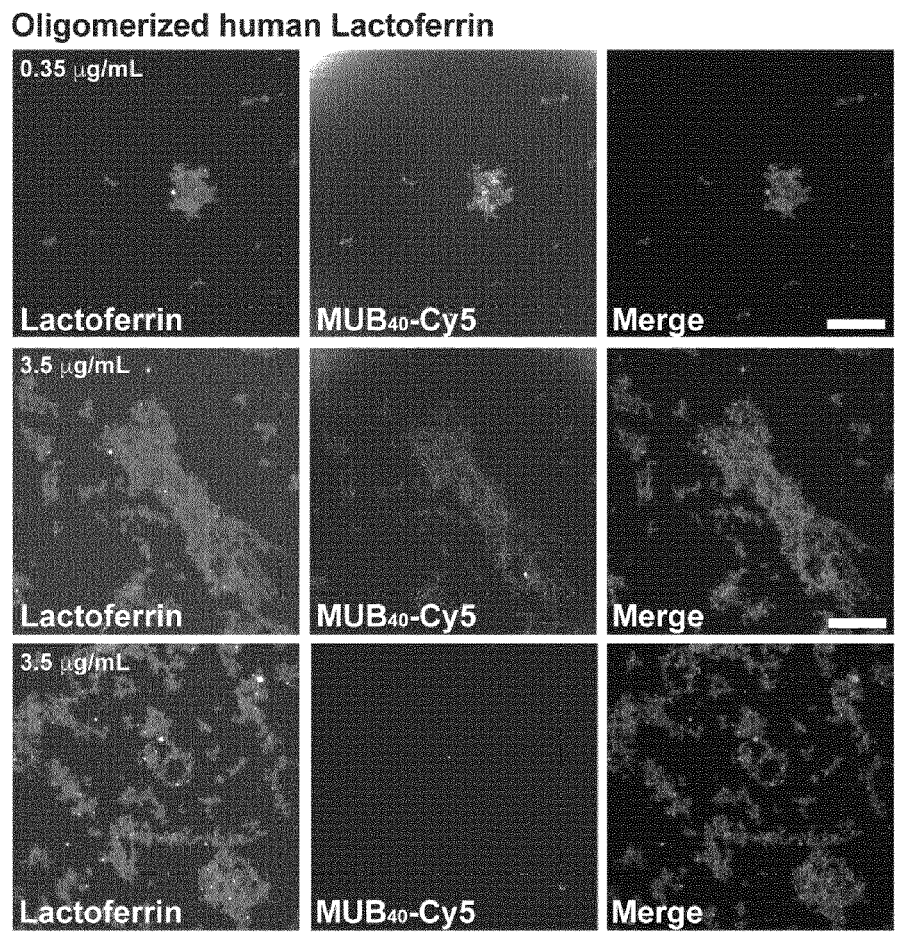
Figure 14F:
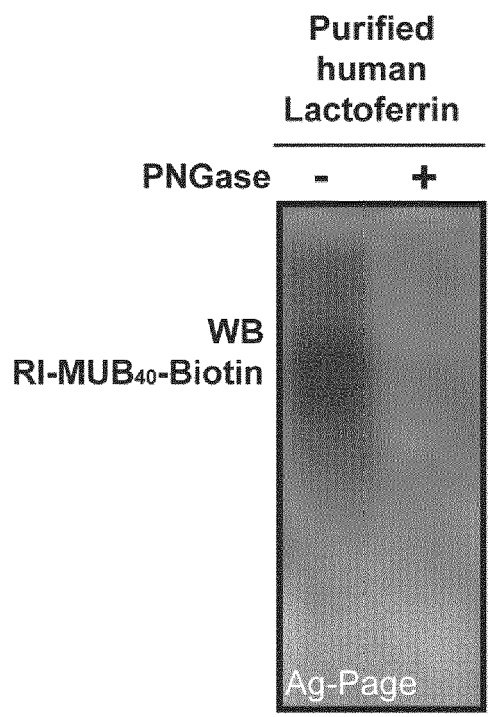

Lactoferrin was identified as a target of MUB$_{40}$ in neutrophil granules, by a pulldown assay with RI-MUB$_{40}$-Biotin (FIG. 14C). This result was confirmed by immunofluorescence experiments on fixed human neutrophils, showing a similar localization of the RI-MUB$_{40}$ (SEQ ID NO: 2)-Cy5 and $\alpha$-lactoferrin fluorescent signals (FIG. 14D). The MUB$_{40}$ lactoferrin-binding property was finally demonstrated with human purified lactoferrin incubated in a RMPI 1640 medium supplemented with 10 mM Hepes and 3 mM glucose, which allowed the formation of lactoferrin oligomers, as previously performed in other medium (Bennett et al., 1981), (Mantel et al., 1994). Again, in this experimental model, a similar localization of the RI-MUB$_{40}$ (SEQ ID NO: 2)-Cy5 and $\alpha$-lactoferrin fluorescent signals was observed (FIG. 14E). N-deglycosylation of lactoferrin with PNGase abolished MUB$_{40}$ (SEQ ID NO: 3)-Cy5 labeling, suggesting that lactoferrin glycosylation moiety was essential for MUB$_{40}$ binding to lactoferrin (FIG. 14E-F).

As a conclusion, MUB$_{40}$ (SEQ ID NO: 3) is a marker of lactoferrin, which is the most abundant protein stored in neutrophil specific and tertiary granules. The potential use of MUB$_{40}$ (SEQ ID NO: 3)-Cy5 as a marker of lactoferrin secretion was further assessed during Shigella flexneri infection in vitro and in in vivo models of inflammation.

Detection of Lactoferrin Degranulation with MUB$_{40}$-Cy5 In Vitro and In Vivo

Neutrophil granule inducible exocytosis (or degranulation) occurs in the presence of an inflammatory stimulus, such as bacterial infection. Here, for the first time, the degranulation process could be assessed in vitro on living neutrophils infected with Shigella flexneri by live fluorescence microscopy in the presence of RI-MUB$_{40}$-Cy5: transient, dot-shaped fluorescent signals were detected on the cells' surface (FIG. 16A), strongly suggesting that exocytosed lactoferrin was bound extracellularly to RI-MUB$_{40}$-Cy5. Since RI-MUB$_{40}$-Cy5 was not degraded by proteases (FIG. 5C-D), the fact that transient lactoferrin labeling might be due to its solubilization in the culture medium leading to the dilution of the fluorescent signal. Lactoferrin detection with RI-MUB$_{40}$ (SEQ ID NO: 2)-Cy5 was strictly extracellular, confirming that this marker does not cross plasma membrane of live cells, similarly to MUB$_{70}$ (SEQ ID NO: 11) (Coïc et al., 2012). In vivo, neutrophil lactoferrin secretion was successfully revealed on fixed tissues with MUB$_{40}$-Cy5 in the guinea pig colonic mucosa infected by Shigella flexneri; revealing lactoferrin accumulation within the bacteria foci vicinity (FIG. 16B), consistent with previous studies (Masson et al., 1969). The assessment of neutrophil recruitment during Shigella flexneri invasion could not be investigated in the guinea pig model of shigellosis, since the targeted organ deep localization is not compatible with the fluorescence imaging techniques on living animals at the disposal of the inventors.

Further validation of RI-MUB$_{40}$ in living animals suffering of shigellosis was not possible due to the localization of the infected organ, the colon, deep into the abdomen, making the assessment of fluorescent signals difficult given the current state of technology or possibilities offered to the inventors. Alternatively, the capacity of RI-MUB$_{40}$ to specifically label inflammatory tissues was evaluated in an arthritis mouse model (sterile inflammation), using the K/BxN serum transfer model (Bruhns et al., 2003). Indeed, following systemic administration (i.v. injection) of RI-MUB40-Cy5 into arthritic mice, but not their naïve controls, a fluorescent signal accumulated at inflammatory sites, localized in joints, which are known to contain a large population of activated neutrophils (FIG. 16C). The inflammation in articulations was confirmed by the detection of luminol (a MPO substrate, i.v. injection) bioluminescence (FIG. 16C). Notably, epifluorescent (RI-MUB$_{40}$ (SEQ ID NO: 2)-Cy5) and bioluminescent (luminol) signals were significantly higher in arthritic mice compared to controls (FIG. 16C, p$\leq$0.0001, T-test) and correlated (FIG. 16D, p$\leq$0.0001, T-test).

In conclusion, we demonstrated here that MUB$_{40}$ and RI-MUB$_{40}$ peptides allowed the assessment of neutrophil lactoferrin detection in vitro or in vivo. Therefore, the potential use of RI-MUB$_{40}$ as an inflammatory events investigation tool or marker, associated with neutrophil recruitment and activation, was further evaluated on human inflamed tissues.

Neutrophil Labeling with MUB$_{40}$ on Human Inflamed Tissues

Figure 17A:
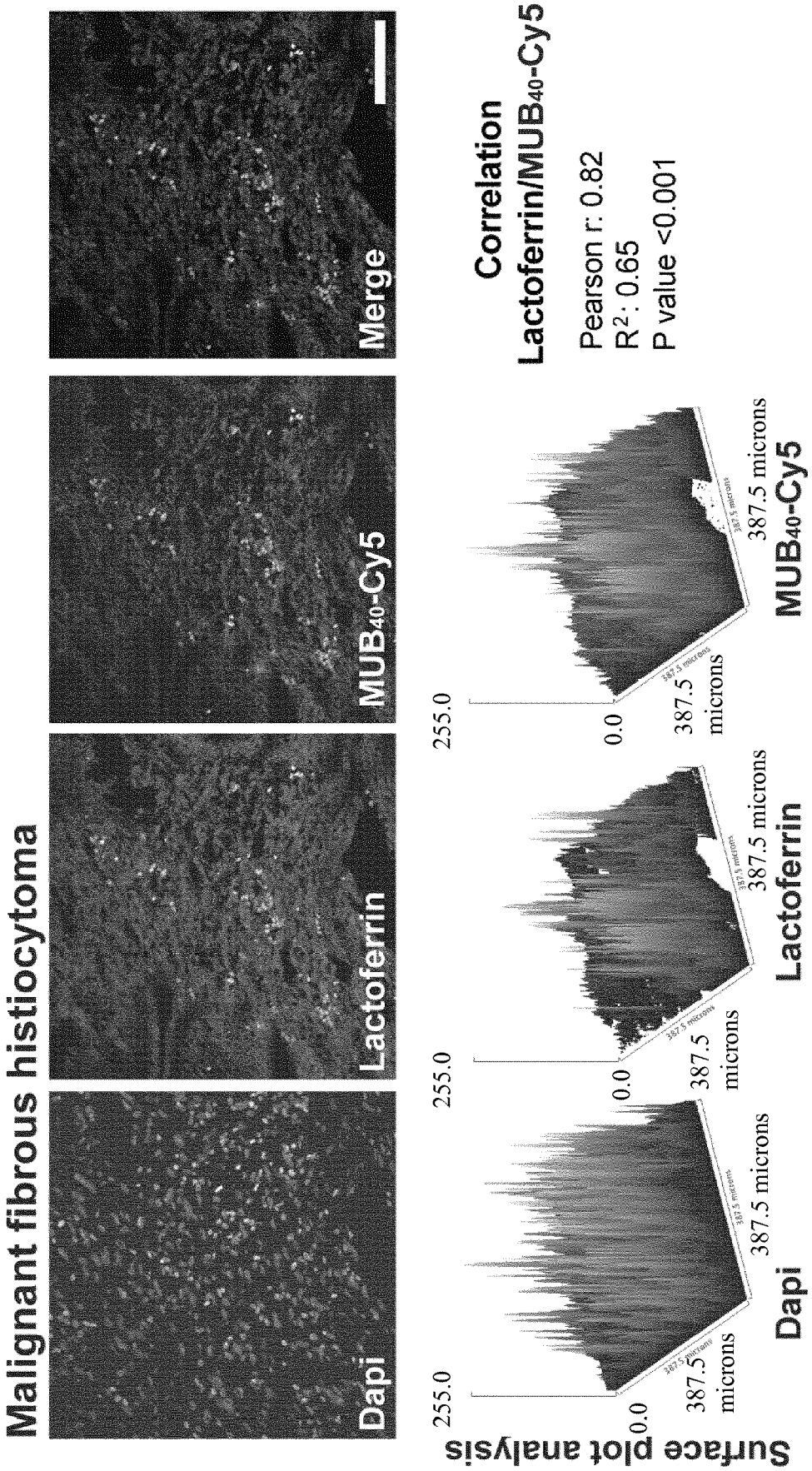
Figure 17B:
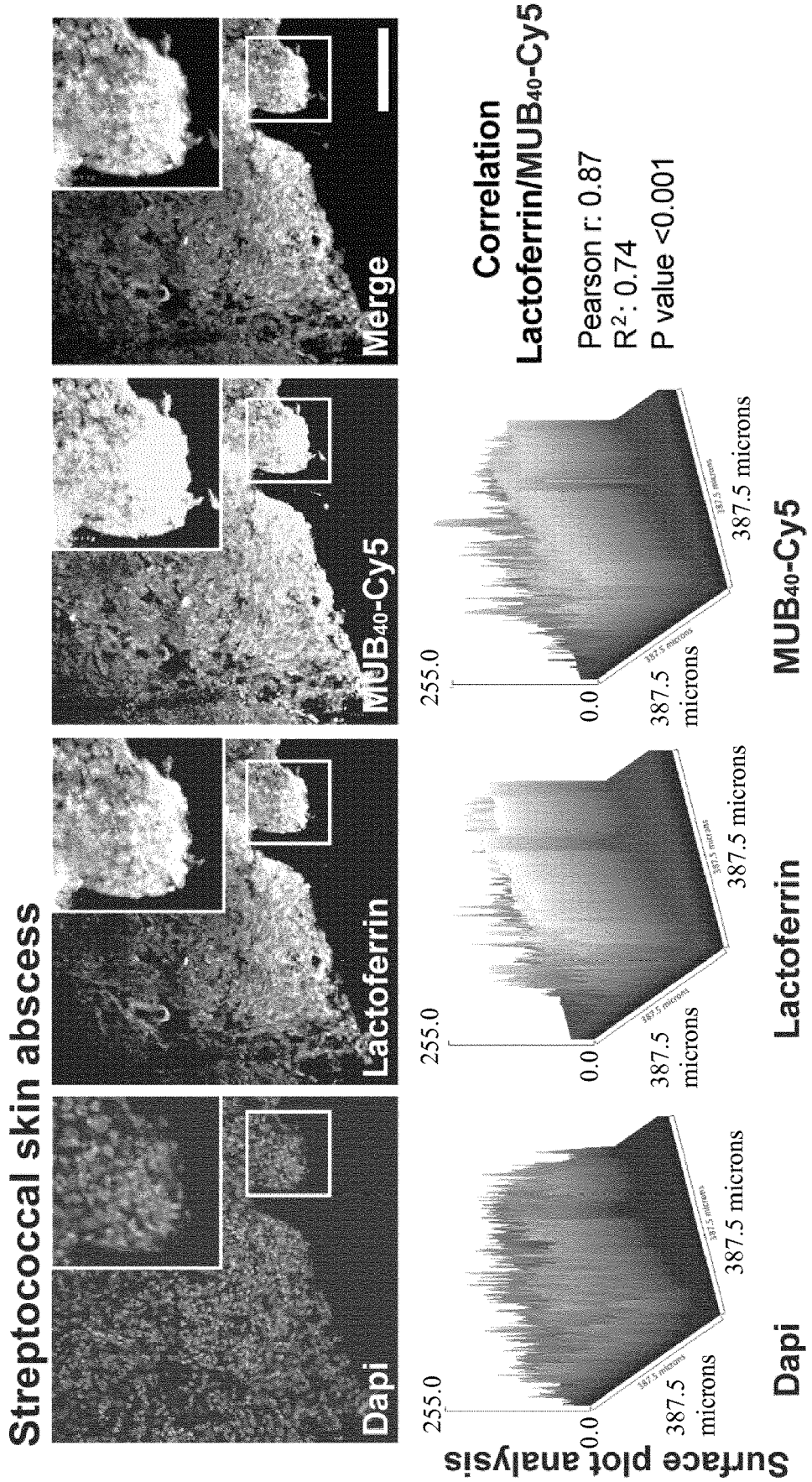

Results reported herein indicated that neutrophil lactoferrin could be labeled with MUB$_{40}$ or RI-MUB$_{40}$ peptides intracellularly on fixed samples (cells and tissues) or extracellularly upon its secretion by living neutrophils upon activation. Neutrophil recruitment and activation was further successfully assessed on various human biopsies from patients diagnosed with sterile or infectious inflammatory diseases with MUB$_{40}$ and illustrated here with a malignant fibrous histiocytoma (FIG. 17A) and a streptococcal skin abscess (FIG. 17B), respectively. In both cases, recruited neutrophils and secreted lactoferrin were labeled with MUB$_{40}$-Cy5 and a α-lactoferrin antibody: corresponding fluorescent signals were α-localized (FIG. 17A-B, p≤0.001, T-test).

In conclusion the inventors demonstrated that so-called MUB$_{40}$ peptides, including retro-inverso ones, allow detection of human lactoferrin and therefore offers a new tool for the assessment of neutrophil recruitment and activation in human inflammatory tissues.

C. Discussion

Using maleimide-biotin and maleimide-Cy5 derivatives, the inventors showed that RI-MUB40 has similar binding properties as MUB40 for colonic mucus (human), mucus produced by human cell lines (L174T) or neutrophil granules. Therefore, RI-MUB40 promises to be a more valuable tool as it is designed to resist to protease degradation, especially as a novel inflammatory marker in particular within mucinous inflammatory tissues, or in the context of bio-conjugates targeting overproducing mucus pathologies (i.e. Cystic fibrosis) for drug delivery, in particular as a vehicle when conjugated with mucolytic molecules.

In addition, the peptidomimetics described herein promise to be interesting tools for innovative therapeutical applications, combining for example such peptidomimetics with mucolytic molecules (acetylcysteine, bromalaine, human DNase I or bacterial mucinases) in order to improve mucus clearance in various pathologies such as Cystic fibrosis, arthritis or inflammatory cancers in order to either improve patients state or existing treatments efficiently promoting the access of therapeutical molecules to inflammatory sites.

As disclosed herein, the inventors designed, synthesized and further validated MUB$_{40}$ and RI-MUB$_{40}$ peptides as novel markers of neutrophil lactoferrin, which may be considered as universal markers of mammalian neutrophils and will facilitate neutrophil detection and study in animal models of inflammation, including mouse, rabbit, or guinea pig (FIGS. 7 and 8), as illustrated by another recent report in guinea pigs (Arena et al., 2016).

As a novel lactoferrin marker, MUB$_{40}$ type probes and/or RI-MUB$_{40}$ type probes will contribute to a better understanding of lactoferrin modulatory and antimicrobial functions in vitro and in vivo. To date, most studies have focused on the importance of mucus lactoferrin in the protection of the respiratory tract from inflammation or infection in vivo (Valenti et al., 2011), (Sagel et al., 2009), (Dubin et al., 2004) or in lung epithelial cell culture models (Calu3 (Babu et al., 2004)). Lactoferrin abundance and function in the intestinal tract has been less investigated, although confirmed in humans (Peen et al., 1996); its protective role was confirmed in a mouse model of colitis (Ye et al., 2014). The resistance of lactoferrin to bacteria secreted serine proteases (SPATE) proteolysis strongly support its importance in preserving the epithelial lineage from bacterial aggression (Gutierrez-Jimenez et al., 2008). The use of MUB$_{40}$ type probes and/or RI-MUB$_{40}$ type probes will promote lactoferrin studies in intestinal inflammation and infection.

The inventors previously characterized MUB$_{70}$ colonic mucus-binding property mediated by its ability to interact with a Mucin 2 glycosylation moiety (Coïc et al., 2012). Here the inventors have confirmed that its shorter derivative, MUB$_{40}$-Cy5, similarly labeled colonic mucus and goblet cells' granules (FIGS. 1B, C and F). The inventors demonstrated that MUB$_{70}$ (data not shown) and MUB$_{40}$ peptides labeled neutrophil granules (FIGS. 1F and 5A) by interacting with a lactoferrin glycosylation moiety (FIG. 14E-F). Taken together, these results raised the question of the specificity of MUB$_{70}$ and MUB$_{40}$ targets in mucus samples and in neutrophil granules. Muc2 and lactoferrin are both present in the colonic mucus, and both play a key role in the protection of the colonic mucosa from colitis (Ye et al., 2014) (Faure et al., 2004). For technical reasons, the inventors could not isolate and purify either Muc2 or lactoferrin from the mucus matrix, which is a complex and dense hydrogel. Considering that mucins are not expressed by neutrophils, lactoferrin can be considered a specific target of MUB$_{40}$ type probes and/or RI-MUB$_{40}$ type probes in neutrophil granules. This assumption is supported here by the demonstration of the interaction between purified human lactoferrin and MUB$_{40}$ (FIGS. 14C and F). However, we cannot rule out the possibility that MUB$_{40}$ may label lactoferrin present in colonic mucus together with Muc2. Although difficult, further investigations will be required to address the MUB$_{40}$ target specificity in colonic mucus.

Using RI-MUB$_{40}$-Cy5, the inventors could reveal neutrophil degranulation for the first time in inflammatory tissues in vivo with a non-invasive method (FIG. 16C-D). Notably the intensity of fluorescent signal correlated with disease severity, suggesting that RI-MUB$_{40}$-Cy5 is not only a marker for inflammation in vivo, but also allows the appreciation of inflammation intensity.

The inventors demonstrated that MUB$_{40}$ is a specific neutrophil marker, which may be used, in a broad range of in vitro assays. Further investigations will be required to validate RI-MUB$_{40}$ as a potentially new inflammation marker in vivo, including a pre-clinical study for evaluating toxicity, bioavailability, specificity and sensitivity of its lactoferrin-binding property. Labeling RI-MUB$_{40}$ with radioactive elements can be envisaged for inflammation site localization with non-invasive inflammation-imaging methods such as scintigraphy, PET or SPECT (Wu et al., 2013) (Zhang et al., 2010) (Zhang et al., 2007), (Locke et al., 2009).

Significance

Neutrophils are major players of the innate immune response during inflammation and infection, although their detection remains difficult in animal models and humans. Here the inventors have described MUB$_{40}$ type probes and/or RI-MUB$_{40}$ type probes as specific markers of neutrophils, binding to lactoferrin, stored in specific and tertiary granules or released upon neutrophil activation. MUB$_{40}$ and its retro-inverso derivative RI-MUB$_{40}$ allow the imaging of neutrophils in vitro and in vivo in inflammation animal models; these markers will open new doors in neutrophil study, non-invasive live imaging of inflammation and diagnostic of inflammatory diseases.

BIBLIOGRAPHY

Anderson, M. C., Vonaesch, P., Saffarian, A., Marteyn, B. S., and Sansonetti, P. J. (2017). Shigella sonnei Encodes a Functional T6SS Used for Interbacterial Competition and Niche Occupancy. Cell Host Microbe 21, 769-776.e3.

Arena, E. T., Tinevez, J.-Y., Nigro, G., Sansonetti, P. J., and Marteyn, B. S. (2016). The infectious hypoxia: Occurrence and causes during Shigella infection. Microbes Infect.

Babu, P. B. R., Chidekel, A., and Shaffer, T. H. (2004). Protein composition of apical surface fluid from the human airway cell line Calu-3: effect of ion transport mediators. Clin. Chim. Acta 347, 81-88.

Bennett, R. M., Bagby, G. C., and Davis, J. (1981). Calcium-dependent polymerization of lactoferrin. Biochem. Biophys. Res. Commun. 101, 88-95.

Borregaard, N., Sørensen, O. E., and Theilgaard-Mönch, K. (2007). Neutrophil granules: a library of innate immunity proteins. Trends Immunol. 28, 340-345.

Bruhns, P., Samuelsson, A., Pollard, J. W., and Ravetch, J. V. (2003). Colony-stimulating factor-1-dependent macrophages are responsible for IVIG protection in antibody-induced autoimmune disease. Immunity 18, 573-581.

Chorev, M., and Goodman, M. A *Dozen Years of Retro-Inverso Peptidomimetics* (1993) Accounts Chem Res, 5266-273

Chorev, M., and Goodman, M. *Recent Developments in Retro Peptides and Proteins—an Ongoing Topochemical Exploration* (1995) Trends Biotechnol, 10438-445

Coïc, Y.-M., Baleux, F., Poyraz, Ö., Thibeaux, R., Labruyere, E., Chretien, F., Sobhani, I., Lazure, T., Wyplosz, B., Schneider, G., et al. (2012). Design of a specific colonic mucus marker using a human commensal bacterium cell surface domain. J. Biol. Chem. 287, 15916-15922.

Coïc, Y. M., Lan, C. L., Neumann, J. M., Jamin, N., and Baleux, F. *Slightly modifying pseudoproline dipeptides incorporation strategy enables solid phase synthesis of a 54 AA fragment of caveolin-1 encompassing the intramembrane domain* (2010) Journal of peptide science: an official publication of the European Peptide Society, 298-104

Coron, E., Flamant, M., Aubert, P., Wedel, T., Pedron, T., Letessier, E., Galmiche, J. P., Sansonetti, P. J., and Neunlist, M. (2009). Characterisation of early mucosal and neuronal lesions following *Shigella flexneri* infection in human colon. PLoS ONE 4, e4713.

Cowland, J. B., and Borregaard, N. (2016). Granulopoiesis and granules of human neutrophils. Immunol. Rev. 273, 11-28.

Däbritz, J., Musci, J., and Foell, D. (2014). Diagnostic utility of faecal biomarkers in patients with irritable bowel syndrome. World J. Gastroenterol. 20, 363-375.

Dubin, R. F., Robinson, S. K., and Widdicombe, J. H. (2004). Secretion of lactoferrin and lysozyme by cultures of human airway epithelium. Am. J. Physiol. Lung Cell Mol. Physiol. 286, L750-L755.

Faure, M., Moennoz, D., Mettraux, C., Montigon, F., Schiffrin, E. J., Obled, C., Breuille, D., and Boza, J. (2004). The chronic colitis developed by HLA-B27 transgenic rats is associated with altered in vivo mucin synthesis. Dig Dis Sci 49, 339-346.

Faurschou, M., and Borregaard, N. (2003). Neutrophil granules and secretory vesicles in inflammation. Microbes Infect. 5, 1317-β27.

Fontaine, S. D., Reid, R., Robinson, L., Ashley, G. W., and Santi, D. V. *Long-term stabilization of maleimide-thiol conjugates* (2015) Bioconjugate chemistry, 1145-152.

Fuente-Nunez et al., 2015, Chemistry & Biology 22, 196-205, "D-Enantiomeric Peptides that Eradicate Wild-Type and Multidrug-Resistant Biofilms and Protect against Lethal *Pseudomonas aeruginosa* Infections" Gouni-Berthold, I., Baumeister, B., Wegel, E., Berthold, H. K., Vetter, H., and Schmidt, C. (1999). Neutrophil-elastase in chronic inflammatory bowel disease: a marker of disease activity? Hepatogastroenterology 46, 2315-2320. Gutierrez-Jimenez, J., Arciniega, I., and Navarro-Garcia, F. (2008). The serine protease motif of Pic mediates a dose-dependent mucolytic activity after binding to sugar constituents of the mucin substrate. Microb. Pathog. 45, 115-123.

Ho, A.-S., Chen, C.-H., Cheng, C.-C., Wang, C.-C., Lin, H.-C., Luo, T.-Y., Lien, G.-S., and Chang, J. (2014). Neutrophil elastase as a diagnostic marker and therapeutic target in colorectal cancers. Oncotarget 5, 473-480. Iorns, E., Gunn, W., Erath, J., Rodriguez, A., Zhou, J., Benzinou, M., and Reproducibility, I. *Replication attempt: "Effect of BMAP-28 antimicrobial peptides on Leishmania major promastigote and amastigote growth: role of leishmanolysin in parasite survival"* (2014) PloS one, 12e114614

Iwai et al., in Peptides 22 (2001) 853-860

Johnson, T., Quibell, M., and Sheppard, R. *C.N,O-bisFmoc derivatives of N-(2-hydroxy-4-methoxybenzyl)-amino acids: useful intermediates in peptide synthesis* (1995) Journal of peptide science: an official publication of the European Peptide Society, 111-25

Jones, S. A. et al., 2007. Respiration of *Escherichia coli* in the mouse intestine. Infect Immun, 75(10), pp. 4891-4899.

Kjeldsen, L., Sengelov, H., and Borregaard, N. (1999). Subcellular fractionation of human neutrophils on Percoll density gradients. J. Immunol. Methods 232, 131-143.

Lehmann, F. S., Burri, E., and Beglinger, C. (2015). The role and utility of faecal markers in inflammatory bowel disease. Therap Adv Gastroenterol 8, 23-36.

Locke, L. W., Chordia, M. D., Zhang, Y., Kundu, B., Kennedy, D., Landseadel, J., Xiao, L., Fairchild, K. D., Berr, S. S., Linden, J., et al. (2009). A novel neutrophil-specific PET imaging agent: cFLFLFK-PEG-64Cu. J. Nucl. Med. 50, 790-797.

Mantel, C., Miyazawa, K., and Broxmeyer, H. E. (1994). Physical characteristics and polymerization during iron saturation of lactoferrin, a myelopoietic regulatory molecule with suppressor activity. Adv. Exp. Med. Biol. 357, 121-132.

Martinez, E., Bartolomé, B. & la Cruz, de, F., 1988. pACYC184-derived cloning vectors containing the multiple cloning site and lacZ alpha reporter gene of pUC8/9 and pUC18/19 plasmids. Gene, 68(1), pp. 159-162.

Martins, C. A., Fonteles, M. G., Barrett, L. J., and Guerrant, R. L. (1995). Correlation of lactoferrin with neutrophilic inflammation in body fluids. Clin. Diagn. Lab. Immunol. 2, 763-765.

Masson, P. L., Heremans, J. F., and Schonne, E. (1969). Lactoferrin, an iron-binding protein in neutrophilic leukocytes. J. Exp. Med. 130, 643-658.

Mergler, M., Dick, F., Sax, B., Weiler, P., and Vorherr, T. *The aspartimide problem in Fmoc-based SPPS. Part I* (2003) Journal of peptide science: an official publication of the European Peptide Society, 136-46

Monceaux, V. et al., 2016. Anoxia and glucose supplementation preserve neutrophil viability and function. Blood, 128(7), pp. 993-1002.

Mutter, M., Nefzi, A., Sato, T., Sun, X., Wahl, F., and Wohr, T. *Pseudo-prolines (psi Pro) for accessing "inaccessible" peptides* (1995) Peptide research, 3145-153

Nothelfer, K., Arena, E. T., Pinaud, L., Neunlist, M., Mozeleski, B., Belotserkovsky, I., Parsot, C., Dinadayala, P., Burger-Kentischer, A., Raqib, R., et al. (2014). B lymphocytes undergo TLR2-dependent apoptosis upon *Shigella* infection. J. Exp. Med. 211, 1215-1229.

Orsi, N. (2004). The antimicrobial activity of lactoferrin: current status and perspectives. Biometals 17, 189-196.

Peen, E., Eneström, S., and Skogh, T. (1996). Distribution of lactoferrin and 60/65 kDa heat shock protein in normal and inflamed human intestine and liver. Gut 38, 135-140.

Sagel, S. D., Sontag, M. K., and Accurso, F. J. (2009). Relationship between antimicrobial proteins and airway inflammation and infection in cystic fibrosis. Pediatr. Pulmonol. 44, 402-409.

Sagel, S. D., Wagner, B. D., Anthony, M. M., Emmett, P., and Zemanick, E. T. (2012). Sputum biomarkers of inflammation and lung function decline in children with cystic fibrosis. Am. J. Respir. Crit. Care Med. 186, 857-865. Sansonetti, P. J., Arondel, J., Huerre, M., Harada, A., and Matsushima, K. (1999). Interleukin-8 controls bacterial transepithelial translocation at the cost of epithelial destruction in experimental shigellosis. Infect. Immun. 67, 1471-1480.

Sengelov, H., Follin, P., Kjeldsen, L., Lollike, K., Dahlgren, C., and Borregaard, N. (1995). Mobilization of granules and secretory vesicles during in vivo exudation of human neutrophils. J. Immunol. 154, 4157-4165.

Shim, D. H. et al., 2007. New animal model of shigellosis in the Guinea pig: its usefulness for protective efficacy studies. *J Immunol*, 178(4), pp. 2476-2482.

Sipponen, T. (2013). Diagnostics and prognostics of inflammatory bowel disease with fecal neutrophil-derived biomarkers calprotectin and lactoferrin. Dig Dis 31, 336-344.

Snippert, H. J., Schepers, A. G., Delconte, G., Siersema, P. D., and Clevers, H. (2011). Slide preparation for single-cell-resolution imaging of fluorescent proteins in their three-dimensional near-native environment. Nat Protoc 6, 1221-1228.

Soehnlein, O., Weber, C., and Lindbom, L. (2009). Neutrophil granule proteins tune monocytic cell function. Trends Immunol. 30, 538-546.

Stragier, E., and Van Assche, G. (2013). The use of fecal calprotectin and lactoferrin in patients with IBD. Review. Acta Gastroenterol. Belg. 76, 322-328.

Sugi, K., Saitoh, O., Hirata, I., and Katsu, K. (1996). Fecal lactoferrin as a marker for disease activity in inflammatory bowel disease: comparison with other neutrophil-derived proteins. Am. J. Gastroenterol. 91, 927-934.

Tyanova, S., Temu, T. & Cox, J., 2016. The MaxQuant computational platform for mass spectrometry-based shotgun proteomics. *Nat Protoc*, 11(12), pp. 2301-2319.

Valenti, P., Catizone, A., Pantanella, F., Frioni, A., Natalizi, T., Tendini, M., and Berlutti, F. (2011). Lactoferrin decreases inflammatory response by cystic fibrosis bronchial cells invaded with Burkholderia cenocepacia iron-modulated biofilm. Int J Immunopathol Pharmacol 24, 1057-1068.

Wang, J., Lei, Y., Xie, C., Lu, W., Wagner, E., Xie, Z., Gao, J., Zhang, X., Yan, Z., and Liu, M. *Retro-inverso CendR peptide-mediated polyethyleneimine for intracranial glioblastoma-targeting gene therapy* (2014) Bioconjugate chemistry, 2414-423

Wei, X., Zhan, C., Shen, Q., Fu, W., Xie, C., Gao, J., Peng, C., Zheng, P., and Lu, W. *A D-peptide ligand of nicotine acetylcholine receptors for brain-targeted drug delivery* (2015) Angewandte Chemie, 103023-3027

West, N. P. et al., 2005. Optimization of virulence functions through glucosylation of Shigella LPS. *Science*, 307 (5713), pp. 1313-1317.

Wu, C., Li, F., Niu, G., and Chen, X. (2013). PET imaging of inflammation biomarkers. Theranostics 3, 448-466.

Yang, H. Q., and Zubarev, R. A. *Mass spectrometric analysis of asparagine deamidation and aspartate isomerization in polypeptides* (2010) Electrophoresis, 111764-1772

Ye, Q., Zheng, Y., Fan, S., Qin, Z., Li, N., Tang, A., Ai, F., Zhang, X., Bian, Y., Dang, W., et al. (2014). Lactoferrin deficiency promotes colitis-associated colorectal dysplasia in mice. PLoS ONE 9, e103298.

Zhang, Y., Kundu, B., Fairchild, K. D., Locke, L., Berr, S. S., Linden, J., and Pan, D. (2007). Synthesis of novel neutrophil-specific imaging agents for Positron Emission Tomography (PET) imaging. Bioorg. Med. Chem. Lett. 17, 6876-6878.

Zhang, Y., Xiao, L., Chordia, M. D., Locke, L. W., Williams, M. B., Berr, S. S., and Pan, D. (2010). Neutrophil targeting heterobivalent SPECT imaging probe: cFLFLF-PEG-TKPPR-99mTc. Bioconjug. Chem. 21, 1788-1793.

The invention claimed is:

1. A method of detecting lactoferrin, comprising:
   a) contacting lactoferrin with a D amino-acid peptidomimetic, wherein the D amino-acid peptidomimetic comprises the amino acid sequence of SEQ ID NO: 1; and
   b) detecting the D amino-acid peptidomimetic bound to the lactoferrin.

2. The method of claim 1, wherein the D amino-acid peptidomimetic comprises the amino acid sequence of SEQ ID NO: 2.

3. The method of claim 2, wherein the D amino-acid peptidomimetic consists of the amino acid sequence of SEQ ID NO: 2.

4. The method of claim 1, wherein the D amino-acid peptidomimetic further comprises a label and/or a reporter or a carrier entity, and/or is associated with an active molecule.

5. The method of claim 4, wherein the D amino-acid peptidomimetic is labelled by coupling with a fluorophore or a biotin.

6. The method of claim 1, wherein the D amino-acid peptidomimetic has the capacity to adopt a multimeric organization and/or is a trimer.

7. The method of claim 1, wherein the D amino-acid peptidomimetic has a D-Cysteine residue at its extremity-terminus.

8. The method of claim 1, wherein the D amino-acid peptidomimetic has an amide group at its C-terminus and/or an acetyl group at its N-terminus.

9. The method of claim 1, wherein the lactoferrin is present in a patient sample or in a patient (in vivo).

10. The method of claim 9, wherein lactoferrin associated with neutrophils is detected.

11. The method of claim 9, wherein lactoferrin associated with neutrophil granules is detected.

12. The method of claim 9, wherein lactoferrin associated with mucus is detected.

13. The method of claim 9, wherein lactoferrin secreted by neutrophils that is detected.

14. The method of claim 9, wherein the presence of detected lactoferrin indicates neutrophilic inflammation.

15. The method of claim 9, wherein the method comprises administering the D amino-acid peptidomimetic to the patient.

16. The method of claim 9, wherein the patient has or is suspected to have a pathogen infection.

17. The method of claim 16, wherein the pathogen infection is a bacterial infection.

18. The method of claim 9, wherein the patient has or is suspected to have a neoplastic disease.

19. The method of claim 18, wherein the neoplastic disease is selected from mucinous carcinoma, gastric cancer and colorectal cancer.

20. The method of claim 9, wherein the patient has or is suspected to have cystic fibrosis.

21. The method of claim 9, wherein the patient has or is suspected to have an intestine inflammatory disease.

22. The method of claim 9, wherein the sample comprises living cells.

23. The method of claim 1, wherein the lactoferrin is glycosylated.

24. The method of claim 1, wherein the lactoferrin is one or more of glycosylated lactoferrin, neutrophil lactoferrin stored in neutrophil specific granules (β1), neutrophil lactoferrin stored in tertiary granules (β2), and lactoferrin secreted by neutrophils.

\* \* \* \* \*